(12) United States Patent
Levy et al.

(10) Patent No.: US 11,633,473 B2
(45) Date of Patent: Apr. 25, 2023

(54) STIMULATOR OF INTERFERON GENES (STING) LIGANDS AND USES THEREOF

(71) Applicant: Children's Medical Center Corporation, Boston, MA (US)

(72) Inventors: Ofer Levy, Cambridge, MA (US); David J. Dowling, Brighton, MA (US); Francesco Borriello, Jamaica Plain, MA (US); Carlo Pietrasanta, Boston, MA (US)

(73) Assignee: Children's Medical Center Corporation, Boston, MA (US)

( * ) Notice: Subject to any disclaimer, the term of this patent is extended or adjusted under 35 U.S.C. 154(b) by 0 days.

(21) Appl. No.: 16/766,902

(22) PCT Filed: Nov. 27, 2018

(86) PCT No.: PCT/US2018/062674
§ 371 (c)(1),
(2) Date: May 26, 2020

(87) PCT Pub. No.: WO2019/104353
PCT Pub. Date: May 31, 2019

(65) Prior Publication Data
US 2021/0299250 A1    Sep. 30, 2021

Related U.S. Application Data

(60) Provisional application No. 62/597,604, filed on Dec. 12, 2017, provisional application No. 62/591,175, filed on Nov. 27, 2017.

(51) Int. Cl.
A61K 39/39 (2006.01)
A61P 31/16 (2006.01)
A61K 39/145 (2006.01)
A61K 39/00 (2006.01)

(52) U.S. Cl.
CPC .......... *A61K 39/39* (2013.01); *A61K 39/145* (2013.01); *A61P 31/16* (2018.01); *A61K 2039/545* (2013.01); *A61K 2039/55* (2013.01); *A61K 2039/55505* (2013.01); *A61K 2039/55561* (2013.01); *C12N 2760/16134* (2013.01)

(58) Field of Classification Search
None
See application file for complete search history.

(56) References Cited

U.S. PATENT DOCUMENTS

2016/0074507 A1   3/2016   Manel et al.
2017/0333552 A1   11/2017  Dubensky et al.

OTHER PUBLICATIONS

PCT/US2018/062074, Feb. 14, 2019, International Search Report and Written Opinion.
PCT/US2018/062074, Jun. 11, 2020, International Preliminary Report on Patentability.

*Primary Examiner* — Michelle S Horning
(74) *Attorney, Agent, or Firm* — Wolf, Greenfield & Sacks, P.C.

(57) ABSTRACT

Provided herein are Stimulator of Interferon Genes (STING) ligand for use in enhancing immune response and/or as adjuvants in vaccines. In some embodiments, STING ligand is used alone or in combination with Alum in an adjuventation system for early life immunization.

17 Claims, 23 Drawing Sheets

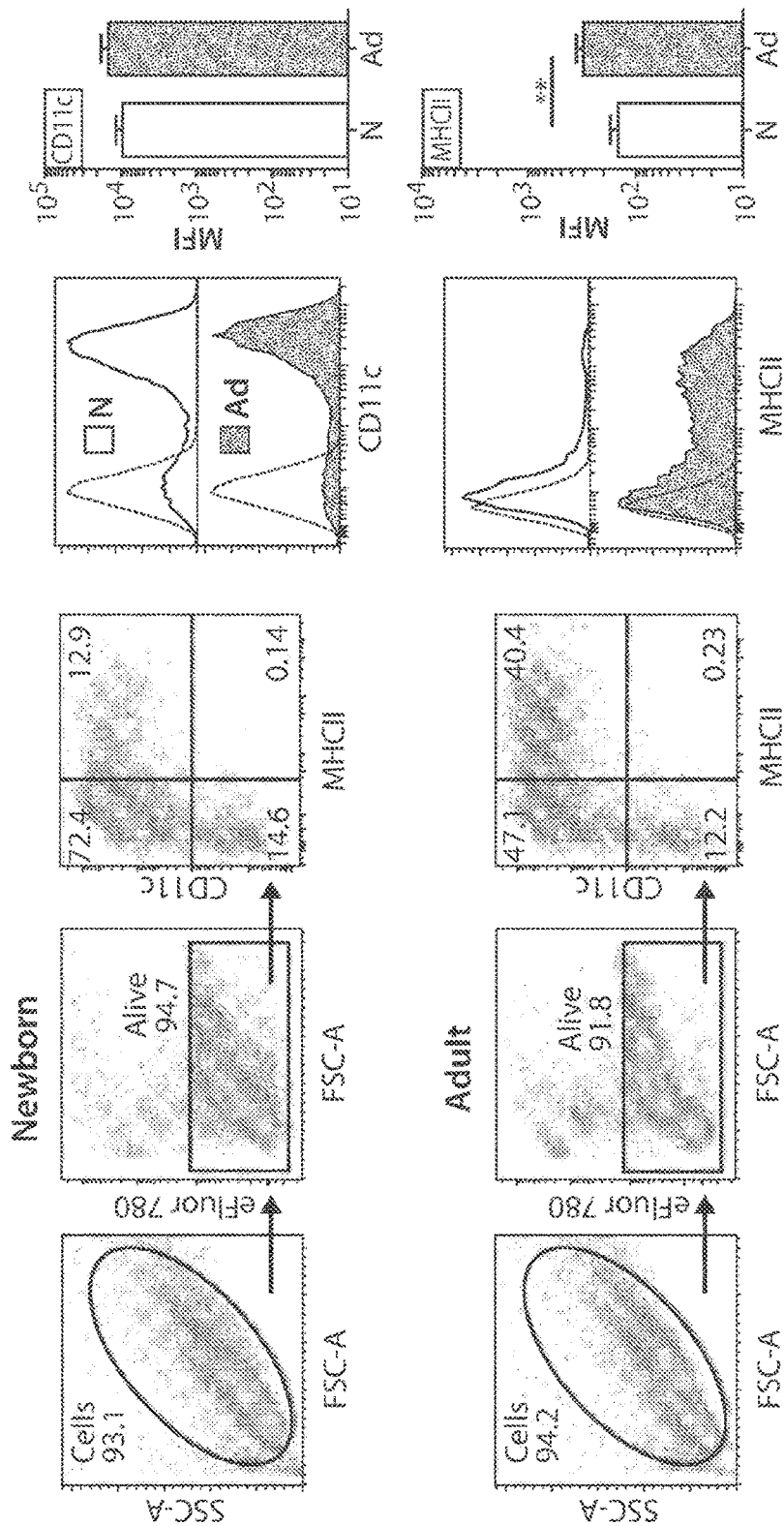

STIMULATOR OF INTERFERON GENES (STING) LIGANDS AND USES THEREOF

RELATED APPLICATIONS

This application is a National Stage Filing under 35 U.S.C. § 371 of International Application No. PCT/US2018/062674, filed Nov. 27, 2018, which claims the benefit under 35 U.S.C. § 119(e) to U.S. Provisional Application No. 62/591,175, filed Nov. 27, 2017, entitled "IDENTIFICATION AND CHARACTERIZATION OF STING AS ADJUVANT TARGET FOR EARLY LIFE IMMUNIZATION", and U.S. Provisional Application No. 62/597,604, filed Dec. 12, 2017, entitled "IDENTIFICATION AND CHARACTERIZATION OF STING AS ADJUVANT TARGET FOR EARLY LIFE IMMUNIZATION", the entire contents of all of which are incorporated herein by reference.

GOVERNMENT LICENSE RIGHTS

This invention was made with government support under Grant Nos. AI100135, AI067353, AI124284 and contract no. HHSN272201400052C awarded by the National Institutes of Health. The government has certain rights in the invention.

BACKGROUND

Infectious diseases represent a major cause of morbidity and mortality in neonates and young infants. For example, each year in the US ~20,000 children <5 years old are hospitalized due to influenza complications and flu-related death may occur, especially among those with underlying chronic illness. Immunization strategies are fundamental to prevent infectious diseases. However, due to age-specific immunity, vaccines often demonstrate reduced efficacy in newborns and young infants compared to adults.

SUMMARY

Provided herein, in some aspects, are the identification of adjuvant candidates for early life immunization. It was demonstrated herein that the Stimulator of Interferon Genes (STING) ligand 2'3'-cGAMP (hereafter cGAMP) induces a comparable expression of surface maturation markers in newborn and adult BMDCs. It was further demonstrated herein that, surprisingly, as compared to alum or cGAMP alone, immunization with cGAMP formulated with alum significantly enhanced antigen-specific antibody production in newborn mice. Accordingly, compositions and methods of using cGAMP in as adjuvantation system are provided herein. In some embodiments, cGAMP formulated with alum can be used as an effective adjuvantation system for early life immunization.

Some aspects of the present disclosure provide methods of inducing an immune response to an antigen in a subject in need thereof, the method comprising administering to the subject an effective amount of an antigen and an effective amount of an adjuvantation system comprising a Stimulator of Interferon Genes (STING) ligand, wherein the subject is a newborn.

In some embodiments, the STING ligand comprises 2'3'-cGAMP. In some embodiments, the adjuvantation system further comprises alum. In some embodiments, the STING ligand is adsorbed into the alum.

In some embodiments, the subject is human. In some embodiments, the subject is a human neonate. In some embodiments, the subject is less than 28 days of age at the time of administration. In some embodiments, the subject is less than 24 hours of age at the time of administration. In some embodiments, the administration occurs at birth of the subject. In some embodiments, a second administration occurs when the subject is less than or equal to 28 days of age. In some embodiments, a second administration occurs when the subject is no more than 6 months of age. In some embodiments, the second administration occurs when the subject is 2 months, 4 months, and 6 months of age. In some embodiments, the subject is born prematurely or has low birth weight. In some embodiments, the subject is a companion animal or a research animal. In some embodiments, the subject is immune-compromised.

In some embodiments, the antigen comprises a protein or polypeptide. In some embodiments, the antigen comprises a nucleic acid encoding a protein or a polypeptide. In some embodiments, the nucleic acid is DNA or RNA. In some embodiments, the antigen is from a microbial pathogen. In some embodiments, the microbial pathogen is a mycobacterium, bacterium, fungus, virus, parasite, or prion. In some embodiments, the bacterium is *Bacillus anthracis, Bordetella pertussis, Corynebacterium diphtheria, Clostridium tetani, Haemophilus* influenza type b, pneumococcus, Staphylococci spp., *Mycobacterium tuberculosis, Neiserria meningitides, Salmonella typhi, Vibrio cholerae,* or *Yersinia pestis.* In some embodiments, the virus is adenovirus, enterovirus such as poliomyelitis, Ebola virus, herpes viruses such as herpes simplex virus, cytomegalovirus and varicella-zoster, measles, mumps, rubella, hepatitis A virus, hepatitis B virus, hepatitis C virus, human papilloma virus, Influenza virus, rabies, Japanese encephalitis, rotavirus, human immunodeficiency virus (HIV), respiratory syncytial virus (RSV), smallpox, yellow fever, or Zika Virus. In some embodiments, the parasite is malaria, *Leishmania,* another protozoan or a helminth. In some embodiments, the fungus is *Candida* spp., *Aspergillus* spp., *Cryptococcus* spp., Mucormycete, *Blastomyces dermatitidis, Histoplasma capsulatum,* or *Sporothrix schenckii.*

In some embodiments, the antigen is a cancer-specific antigen. In some embodiments, the antigen is a heteroclitic epitope or a cryptic epitope derived from the cancer-specific antigen. In some embodiments, the cancer-specific antigen is a neoantigen.

In some embodiments, the antigen comprises a lipopolysaccharide (LPS).

In some embodiments, the antigen and the adjuvatation system are administered simultaneously. In some embodiments, the antigen and the adjuvantation system are administered separately. In some embodiments, the adjuvantation system enhances B cell immunity. In some embodiments, the adjuvantation system enhances the production of antigen-specific antibodies, compared to when the antigen is administered alone. In some embodiments, the adjuvantation system enhances the cytokine production of antigen-specific T cells, compared to when the antigen is administered alone. In some embodiments, the cytokine is IFNγ$^+$. In some embodiments, the adjuvantation system polarizes the innate immune response toward T follicular helper (Tfh) cell immunity. In some embodiments, the adjuvantation system polarizes the innate immune response toward T helper 1 (Th1) cell immunity. In some embodiments, the adjuvantation system prolongs a protective effect in the subject against the antigen, compared to when the antigen is administered alone. In some embodiments, the adjuvantation system increases rate of an immune response, compared to when the antigen is administered alone. In some embodiments, the antigen produces a same level of immune response against the antigen at a lower dose in the presence of the adjuvantation system, compared to when the antigen is administered alone.

In some embodiments, the subject has or is at risk of developing an infectious disease. In some embodiments, the infectious disease is caused a bacterium, a *mycobacterium*, a fungus, a virus, a parasite or a prion. In some embodiments, the infectious disease is sepsis. In some embodiments, the subject has or is at risk of developing cancer. In some embodiments, the cancer is metastatic cancer. In some embodiments, the cancer is melanoma. In some embodiments, the subject has or is at risk of developing allergy.

In some embodiments, the administering is done systemically or locally. In some embodiments, the administering is done intramuscularly, intradermally, orally, intravenously, topically, intranasally, intravaginally, or sublingually. In some embodiments, the administration is prophylactic.

Other aspects of the present disclosure provide methods of inducing an immune response to an antigen in a subject in need thereof, the method comprising administering to the subject an effective amount of an antigen and an effective amount of an adjuvantation system comprising a Stimulator of Interferon Genes (STING) ligand and alum. In some embodiments, the STING ligand comprises 2'3'-cGAMP. In some embodiments, the STING ligand is adsorbed into the alum.

In some embodiments, the subject is a human neonate, an infant, an adult, or an elderly. In some embodiments, the subject is a human neonate. In some embodiments, the subject is less than 28 days of age at the time of administration. In some embodiments, the subject is less than 24 hours of age at the time of administration. In some embodiments, the administration occurs at birth of the subject. In some embodiments, a second administration occurs when the subject is less than or equal to 28 days of age. In some embodiments, a second administration occurs when the subject is no more than 6 months of age. In some embodiments, the administration occurs when the subject is 2 months, 4 months, and 6 months of age. In some embodiments, the subject is born prematurely or has low birth weight. In some embodiments, the subject is a human adult. In some embodiments, the subject is an elderly. In some embodiments, the administration occurs when the subject is more than 65 years of age. In some embodiments, the subject is a companion animal or a research animal. In some embodiments, the subject is immune-compromised.

In some embodiments, the antigen comprises a protein or polypeptide. In some embodiments, the antigen comprises a nucleic acid encoding a protein or a polypeptide. In some embodiments, the nucleic acid is DNA or RNA. In some embodiments, the antigen is from a microbial pathogen. In some embodiments, the microbial pathogen is a *mycobacterium*, bacterium, fungus, virus, parasite, or prion. In some embodiments, the bacterium is *Bacillus anthracis*, *Bordetella pertussis*, *Corynebacterium diphtheria*, *Clostridium tetani*, *Haemophilus* influenza type b, pneumococcus, Staphylococci spp., *Mycobacterium tuberculosis*, *Neiserria meningitides*, *Salmonella typhi*, *Vibrio cholerae*, or *Yersinia pestis*. In some embodiments, the virus is adenovirus, enterovirus such as poliomyelitis, Ebola virus, herpes viruses such as herpes simplex virus, cytomegalovirus and varicella-zoster, measles, mumps, rubella, hepatitis A virus, hepatitis B virus, hepatitis C virus, human papilloma virus, Influenza virus, rabies, Japanese encephalitis, rotavirus, human immunodeficiency virus (HIV), respiratory syncytial virus (RSV), smallpox, yellow fever, or Zika Virus. In some embodiments, the parasite is malaria, *Leishmania*, another protozoan or a helminth. In some embodiments, the fungus is *Candida* spp., *Aspergillus* spp., *Cryptococcus* spp., Mucormycete, *Blastomyces dermatitidis*, *Histoplasma capsulatum*, or *Sporothrix schenckii*.

In some embodiments, the antigen is a cancer-specific antigen. In some embodiments, the antigen is a heteroclitic epitope or a cryptic epitope derived from the cancer-specific antigen. In some embodiments, the cancer-specific antigen is a neoantigen.

In some embodiments, the antigen comprises a lipopolysaccharide (LPS).

In some embodiments, the antigen and the adjuvatation system are administered simultaneously. In some embodiments, the antigen and the adjuvantation system are administered separately. In some embodiments, the adjuvantation system enhances B cell immunity. In some embodiments, the adjuvantation system enhances the production of antigen-specific antibodies, compared to when the antigen is administered alone. In some embodiments, the adjuvantation system enhances the cytokine production of antigen-specific T cells, compared to when the antigen is administered alone. In some embodiments, the cytokine is IFNγ$^+$. In some embodiments, the adjuvantation system polarizes the innate immune response toward T follicular helper (Tfh) cell immunity. In some embodiments, the adjuvantation system polarizes the innate immune response toward T helper 1 (Th1) cell immunity. In some embodiments, the adjuvantation system prolongs a protective effect in the subject against the antigen, compared to when the antigen is administered alone. In some embodiments, the adjuvantation system increases rate of an immune response, compared to when the antigen is administered alone. In some embodiments, the antigen produces a same level of immune response against the antigen at a lower dose in the presence of the adjuvantation system, compared to when the antigen is administered alone. In some embodiments, the subject has or is at risk of developing an infectious disease. In some embodiments, the infectious disease is caused a bacterium, a *mycobacterium*, a fungus, a virus, a parasite or a prion. In some embodiments, the infectious disease is sepsis.

In some embodiments, the subject has or is at risk of developing cancer. In some embodiments, the cancer is metastatic cancer. In some embodiments, the cancer is melanoma.

In some embodiments, the subject has or is at risk of developing allergy.

In some embodiments, the administering is done systemically or locally. In some embodiments, the administering is done intramuscularly, intradermally, orally, intravenously, topically, intranasally, intravaginally, or sublingually. In some embodiments, the administration is prophylactic.

Other aspects of the present disclosure provide adjuvantation systems comprising a Stimulator of Interferon Genes (STING) ligand for use in inducing an immune response to an antigen in a subject in need thereof, wherein the subject is a newborn. In some embodiments, the STING ligand is cGAMP (e.g., 2'3'-cGAMP).

Other aspects of the present disclosure provide adjuvantation systems comprising a Stimulator of Interferon Genes (STING) ligand and alum for use in inducing an immune response to an antigen in a subject in need thereof. In some embodiments, the STING ligand is cGAMP (e.g., 2'3'-cGAMP).

Further provided herein are vaccines comprising an antigen and an adjuvantation system comprising a Stimulator of Interferon Genes (STING) ligand and alum. In some embodiments, the vaccine is for use in immunizing a newborn subject. In some embodiments, the STING ligand is cGAMP (e.g., 2'3'-cGAMP).

BRIEF DESCRIPTION OF DRAWINGS

The accompanying drawings are not intended to be drawn to scale. In the drawings, each identical or nearly identical component that is illustrated in various Figures. is represented by a like numeral. For purposes of clarity, not every component may be labeled in every drawing. In the drawings.

DETAILED DESCRIPTION OF CERTAIN EMBODIMENTS

Figures 1A, 1B:
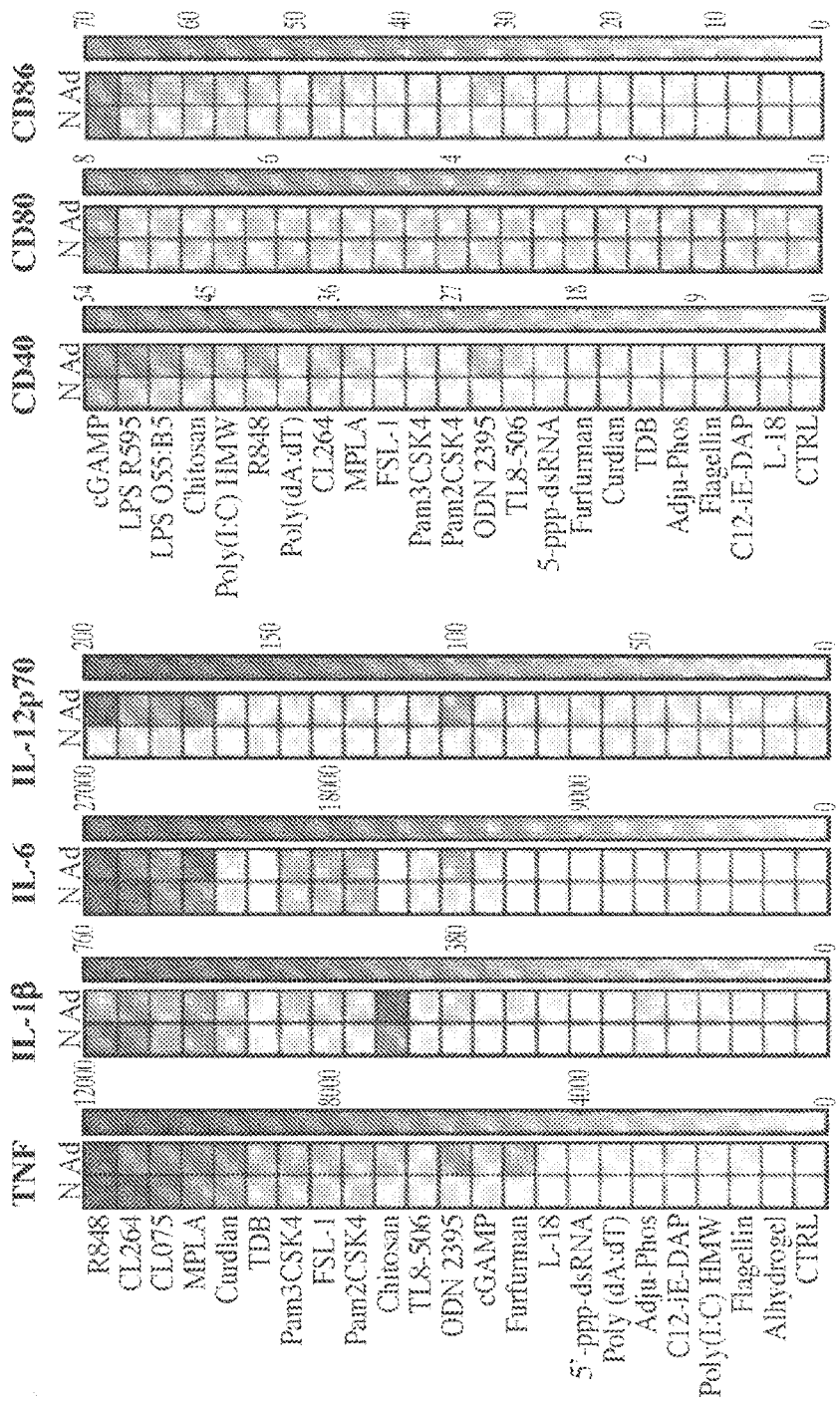
FIG. 1. Screening of PRR agonists on neonatal and adult BMDCs. (A-C) Newborn (N) and adult (Ad) BMDCs were stimulated with the indicated pattern recognition receptor agonists or adjuvants for 20-24 hours. Cytokine production (A, C) and MFI of surface marker expression (B, C) were respectively assessed by ELISA and flow cytometry. (A, B) Color intensities of the heatmaps are proportional to (A) mean cytokine levels (expressed as pg/ml) or (B) mean co-stimulatory molecule levels (expressed as fold change of median fluorescence intensity over CTRL) of 5-6 (A) or 3 (B) independent experiment. (C) Results are expressed as mean+SEM of 4-5 (cytokine production) or 3 (surface marker expression) independent experiments. *p<0.05, **p<0.01 determined by repeated measures two-way ANOVA with Sidak post hoc test.

Some aspects of the present disclosure provide vaccine compositions comprising an antigen and an adjuvantation system comprising a Stimulator of Interferon Genes (STING) ligand. In some embodiments, the adjuvantation system further comprises alum (e.g., the STING ligand is formulated with alum). In some embodiments, the STING ligand is 2'3'-cGAMP (also termed "cGAMP" herein). In some embodiments, the STING ligand (e.g., cGAMP) is adsorbed in alum. The vaccine composition provide herein may be used in methods of inducing an immune response to an antigen in a subject in need thereof, the method comprising administering to the subject an effective amount of an antigen and an effective amount of the adjuvantation system (e.g., either comprising a STING ligand alone, or comprising a STING ligand and alum). In some embodiments, the vaccine composition described herein may be used for inducing an immune response in a subject that is a newborn, an adult, or an elderly. In particular, the vaccine composition described herein is effective for early-life immunization (i.e., for immunizing a newborn subject).

"Stimulator of Interferon Genes (STING)," also known as MITA and MPYS, and encoded by TMEM173 gene, is a signaling molecule associated with the endoplasmic reticulum (ER) and is essential for controlling the transcription of numerous host defense genes, including type I interferons (IFNs) and pro-inflammatory cytokines, following the recognition of aberrant DNA species or cyclic dinucleotides (CDNs) in the cytosol of the cell1.

A "STING ligand" refers to a molecule that can be recognized by STING and can activate STING signaling pathway. Natural STING ligands include DNA that induce CDNs include the genome of invading pathogens, such as herpes simplex virus 1 (HSV1) or certain bacteria species. Self-DNA that has leaked from the nucleus of the host cell, perhaps following cell division or as a consequence of DNA damage, can also be potent activators of the STING pathway. Such DNA species may be responsible for causing various autoinflammatory diseases, such as systemic lupus erythematosus (SLE) or Aicardi-Goutières syndrome (AGS), and may influence inflammation-associated cancer. The commercially available STING ligand (an agonist) MK-1454 is a synthetic cyclic dinucleotide that has potent immunoactivating and antineoplastic activities.

In some embodiments, the STING ligand for use in the vaccine compositions and methods described herein is cyclic guanosine monophosphate (GMP)-adenosine monophosphate (AMP), also termed "cGAMP" herein. cGAMP has been show to bind and activate STING (e.g., as described in Wang et al., Journal of Investigative Dermatology, Volume 136, Issue 11, November 2016, Pages 2183-2191, incorporated herein by reference). However, the effects of STING ligands (e.g., cGAMP) as vaccine adjuvants in newborn subjects have not previously been investigated or demonstrated.

An "adjuvantation system" refers to a composition comprising one or more adjuvants. An "adjuvant" refers to a pharmacological or immunological agent that modifies the effect of other agents, for example, of an antigen in a vaccine. Adjuvants are typically included in vaccines to enhance the recipient subject's immune response to an antigen. The use of adjuvants allows the induction of a greater immune response in a subject with the same dose of antigen, or the induction of a similar level of immune response with a lower dose of injected antigen. Adjuvants are thought to function in several ways, including by increasing the surface area of antigen, prolonging the retention of the antigen in the body thus allowing time for the lymphoid system to have access to the antigen, slowing the release of antigen, targeting antigen to macrophages, activating macrophages, activating leukocytes such as antigen-presenting cells (e.g., monocytes, macrophages, and/or dendritic cells), or otherwise eliciting broad activation of the cells of the immune system see, e.g., H. S. Warren et al, Annu. Rev. immunol., 4:369 (1986), incorporated herein by reference. The ability of an adjuvant to induce and increase a specific type of immune response and the identification of that ability is thus a key factor in the selection of particular adjuvants for vaccine use against a particular pathogen. Adjuvants that are known to those of skill in the art, include, without limitation: aluminum salts (referred to herein as "alum"), liposomes, lipopolysaccharide (LPS) or derivatives such as monophosphoryl lipid A (MPLA) and glycopyranosyl lipid A (GLA), molecular cages for antigen, components of bacterial cell walls, endocytosed nucleic acids such as double-stranded RNA (dsRNA), single-stranded DNA (ssDNA), and unmethylated CpG dinucleotide-containing DNA. Typical adjuvants include water and oil emulsions, e.g., Freund's adjuvant and MF59, and chemical compounds such as aluminum hydroxide or alum. At present, currently licensed vaccines in the United States contain only a limited number of adjuvants, such as alum that enhances production of TH 2 cells and MPLA which activates innate immunity via Toll-like receptor 4 (TLR4). Many of the most effective adjuvants include bacteria or their products, e.g., microorganisms such as the attenuated strain of *Mycobacterium bovis*, Bacille Calmette-Guérin (BCG); microorganism components, e.g., alum-precipitated diphtheria toxoid, bacterial lipopolysaccharides ("endotoxins") and their derivatives such as MPLA and GLA.

In some embodiments, the adjuvantation system of the present disclosure comprises a STING ligand (e.g., cGAMP). In some embodiments, the adjuvantation system of the present disclosure comprises more than one adjuvants (e.g., 2, 3, 4, 5, or more adjuvants). Any known adjuvant may be used in the adjuvantation system described herein, e.g., without limitation, agonists of Pattern Recognition Receptors (PRRs) such as Toll-like receptors (TLRs), NOD-like receptors (NLRs), RIG-I-like receptor, C-type Lectin receptors (CLRs), and other STING ligands. An "agonist" is a chemical that binds to a receptor and activates the receptor to produce a biological response. Agonists of the PPRs enhance immune responses (e.g., innate or adaptive immune response). Agonists of PPRs are known to those skilled in the art. For example, various TLR and NLR agonists are described in Kaczanowska et al, J Leukoc Biol. 2013 June; 93(6): 847-863; Higgins et al., Curr Infect Dis Rep. 2010 January; 12(1):4-12; and Maisonneuve et al., Proc Natl Acad Sci USA. 2014 Aug. 26; 111(34): 12294-12299, incorporated herein by reference. RIG-I-like receptor agonists are described in Ranjith-Kumar et al., J Biol Chem. 2009 Jan. 9; 284(2): 1155-1165; and Goulet et al., PLOS Pathogens 9(8): 10, incorporated herein by reference. CLR agonists are described in Lamb et al., Biochemistry. 2002 Dec. 3; 41(48): 14340-7; and Yan et al., Front Immunol. 2015; 6: 408, incorporated herein by reference. STING agonists are described in Fu et al., Sci Transl Med. 2015 Apr. 15; 7(283): 283ra52; and Foote et al., Cancer Immunology Research, DOI: 10.1158/2326-6066. CIR-16-0284, incorporated herein by reference. The PPR agonists described herein are also commercially available, e.g., from InvivoGen (California, USA). In some embodiments, the adjuvantation system of the present disclosure comprises a STING ligand (e.g., cGAMP) and aluminum salts (referred to herein as "alum"). In some embodiments, the alum is Alhydrogel® (InvivoGen, USA). In some embodiments, in a adjuvantation system comprising a STING ligand (e.g., cGAMP) and alum, the STING ligand (e.g., cGAMP) is adsorbed into alum (e.g., cribed in Jones et al., Journal of Biological Chemistry 280, 13406-13414, 2005, incorporated herein by reference).

Adjuvants or adjuvantation systems are used in vaccine compositions (e.g., the vaccine composition described herein). The terms "vaccine composition" and "vaccine" are used interchangeably herein. A "vaccine composition" is a composition that activates or enhances a subject's immune response to an antigen after the vaccine is administered to the subject. In some embodiments, a vaccine stimulates the subject's immune system to recognize the antigen as foreign, and enhances the subject's immune response if the subject is later exposed to the pathogen, whether attenuated, inactivated, killed, or not. Vaccines may be prophylactic, for example, preventing or ameliorating a detrimental effect of a future exposure to a pathogen, or therapeutic, for example, activating the subject's immune response to a pathogen after the subject has been exposed to the pathogen. In some embodiments, a vaccine composition is used to protect or treat an organism against a disease (e.g., an infectious disease or cancer). In some embodiments, the vaccine is a subunit vaccine (e.g., a recombinant subunit vaccine), an attenuated vaccine (e.g., containing an attenuated pathogen such as a bacterial cell or a viral genome), a live vaccine (e.g., containing a live attenuated pathogen such as a bacterium or virus), or a conjugated vaccine (e.g., a vaccine containing an antigen that is not very immunogenic covalently attached to an antigen that is more immunogenic). One non-limiting example of a conjugated vaccine comprises a LPS attached to a strong protein antigen. Vaccines that contain cancer-specific antigens are termed herein as "cancer vaccine." Cancer vaccines induce cancer-specific immune response against a cancer or a cancer-specific antigen. Such immune response is effective in inhibiting cancer growth and/or preventing reoccurrence of tumor. Cancer vaccines may be used for cancer immunotherapy, which is a type of cancer treatment designed to boost the body's natural defenses to fight the cancer. It uses substances either made by the body or in a laboratory to improve or restore immune system function.

An "antigen" refers to an entity that is bound by an antibody or receptor, or an entity that induces the production of the antibody. In some embodiments, an antigen increases the production of antibodies that specifically bind the antigen. In some embodiments, an antigen comprises a protein or polypeptide. Such protein or peptide are referred to herein as "immunogenic polypeptide." In some embodiments, the term "antigen" encompasses nucleic acids (e.g., DNA or RNA molecules) that encode immunogenic polypeptides. In some embodiments, the antigen is from a microbial pathogen. For example, the antigen may comprise parts (coats, capsules, cell walls, flagella, fimbriae, and toxins) of bacteria, viruses, fungi, and other microorganisms. In some embodiments, the antigen is a cancer-specific antigen.

In some embodiments, a protein or polypeptide antigen is a wild type protein or polypeptide. In some embodiments, a protein or polypeptide antigen is a polypeptide variant to a wild type protein or polypeptide. The term "polypeptide variant" refers to molecules which differ in their amino acid sequence from a native or reference sequence. The amino acid sequence variants may possess substitutions, deletions, and/or insertions at certain positions within the amino acid sequence, as compared to a native or reference sequence. In some embodiments, polypeptide variants possess at least 50% identity to a native or reference sequence. In some embodiments, variants share at least 70%, at least 80%, at least 90%, at least 95%, or at least 99% identity with a native or reference sequence.

In some embodiments, a polypeptide variant comprises substitutions, insertions, deletions. In some embodiments, a polypeptide variant encompasses covalent variants and derivatives. The term "derivative" is used synonymously with the term "variant" but generally refers to a molecule that has been modified and/or changed in any way relative to a reference molecule or starting molecule.

In some embodiments, sequence tags or amino acids, such as one or more lysines, can be added to peptide sequences (e.g., at the N-terminal or C-terminal ends). Sequence tags can be used for peptide detection, purification or localization. Lysines can be used to increase peptide solubility or to allow for biotinylation. Alternatively, amino acid residues located at the carboxy and amino terminal regions of the amino acid sequence of a peptide or protein may optionally be deleted providing for truncated sequences. Certain amino acids (e.g., C-terminal or N-terminal residues) may alternatively be deleted depending on the use of the sequence, as for example, expression of the sequence as part of a larger sequence which is soluble, or linked to a solid support.

In some embodiments, the polypeptide variants comprises at least one amino acid residue in a native or starting sequence removed and a different amino acid inserted in its place at the same position. Substitutions may be single, where only one amino acid in the molecule has been substituted, or they may be multiple, where two or more amino acids have been substituted in the same molecule. In some embodiments, the antigen is a polypeptide that includes 2, 3, 4, 5, 6, 7, 8, 9, 10, or more substitutions compared to a reference protein.

In some embodiments, the substitution is a conservative amino acids substitution. The term "conservative amino acid substitution" refers to the substitution of an amino acid that is normally present in the sequence with a different amino acid of similar size, charge, or polarity. Examples of conservative substitutions include the substitution of a non-polar (hydrophobic) residue such as isoleucine, valine and leucine for another non-polar residue. Likewise, examples of conservative substitutions include the substitution of one polar (hydrophilic) residue for another such as between arginine and lysine, between glutamine and asparagine, and between glycine and serine. Additionally, the substitution of a basic residue such as lysine, arginine or histidine for another, or the substitution of one acidic residue such as aspartic acid or glutamic acid for another acidic residue are additional examples of conservative substitutions. Examples of non-conservative substitutions include the substitution of a non-polar (hydrophobic) amino acid residue such as isoleucine, valine, leucine, alanine, methionine for a polar (hydrophilic) residue such as cysteine, glutamine, glutamic acid or lysine and/or a polar residue for a non-polar residue.

In some embodiments, protein fragments, functional protein domains, and homologous proteins are used as antigens in accordance with the present disclosure. For example, an antigen may comprise any protein fragment (meaning a polypeptide sequence at least one amino acid residue shorter than a reference polypeptide sequence but otherwise identical) of a reference protein 10, 20, 30, 40, 50, 60, 70, 80, 90, 100 or greater than 100 amino acids in length. In another example, any protein that includes a stretch of 20, 30, 40, 50, or 100 amino acids which are 40%, 50%, 60%, 70%, 80%, 90%, 95%, or 100% identical to a reference protein (e.g., a protein from a microbial pathogen) herein can be utilized in accordance with the disclosure.

In some embodiments, the antigen comprises more than one immunogenic proteins or polypeptides (e.g., 2, 3, 4, 5, 6, 7, 8, 9, 10, or more). In some embodiments, the more than one immunogenic proteins or polypeptides are derived from one protein (e.g., different fragments or one protein). In some embodiments, the more than one immunogenic proteins or polypeptides are derived from multiple proteins (e.g., from 2, 3, 4, 5, 6, 7, 8, 9, 10, or more proteins).

In some embodiments, the antigen comprises a nucleic acid encoding an immunogenic protein or polypeptide. In some embodiments, the antigen comprises an immunogenic protein or polypeptide and a nucleic acid encoding the immunogenic protein or polypeptide. The term "nucleic acid" or "polynucleotide," in its broadest sense, includes any compound and/or substance that comprises a polymer of nucleotides. Nucleic acids encoding immunogenic proteins or polypeptides typically comprise an open reading frame (ORF), and one or more regulatory sequences. Nucleic acids (also referred to as polynucleotides) may be or may include, for example, ribonucleic acids (RNAs), deoxyribonucleic acids (DNAs), threose nucleic acids (TNAs), glycol nucleic acids (GNAs), peptide nucleic acids (PNAs), locked nucleic acids (LNAs, including LNA having a β-D-ribo configuration, α-LNA having an α-L-ribo configuration (a diastereomer of LNA), 2'-amino-LNA having a 2'-amino functionalization, and 2'-amino-α-LNA having a 2'-amino functionalization), ethylene nucleic acids (ENA), cyclohexenyl nucleic acids (CeNA) or chimeras or combinations thereof.

In some embodiments, the nucleic acid encoding the immunogenic polypeptide is a DNA (e.g., an expression vector for an immunogenic protein or polypeptide). In some embodiments, the nucleic acid encoding the immunogenic polypeptide is a RNA (e.g., a messenger RNA). A "messenger RNA" (mRNA) refers to any polynucleotide that encodes a (at least one) polypeptide (a naturally-occurring, non-naturally-occurring, or modified polymer of amino acids) and can be translated to produce the encoded polypeptide in vitro, in vivo, in situ, or ex vivo. The basic components of an mRNA molecule typically include at least one coding region, a 5' untranslated region (UTR), a 3' UTR, a 5' cap and a poly-A tail.

In some embodiments, the coding region of the nucleic acid (e.g., DNA or RNA) encoding an immunogenic polypeptide is codon optimized. Codon optimization methods are known in the art and may be used as provided herein. Codon optimization, in some embodiments, may be used to match codon frequencies in target and host organisms to ensure proper folding; bias GC content to increase mRNA stability or reduce secondary structures; minimize tandem repeat codons or base runs that may impair gene construction or expression; customize transcriptional and translational control regions; insert or remove protein trafficking sequences; remove/add post translation modification sites in encoded protein (e.g. glycosylation sites); add, remove or shuffle protein domains; insert or delete restriction sites; modify ribosome binding sites and mRNA degradation sites; adjust translational rates to allow the various domains of the protein to fold properly; or to reduce or eliminate problem secondary structures within the polynucleotide. Codon optimization tools, algorithms and services are known in the art—non-limiting examples include services from GeneArt (Life Technologies), DNA2.0 (Menlo Park Calif.) and/or proprietary methods. In some embodiments, the open reading frame (ORF) sequence is optimized using optimization algorithms.

In some embodiments, a codon optimized sequence shares less than 95% sequence identity to a naturally-occurring or wild-type sequence (e.g., a naturally-occurring or wild-type mRNA sequence encoding an immunogenic protein or polypeptide). In some embodiments, a codon optimized sequence shares less than 90% sequence identity to a naturally-occurring or wild-type sequence (e.g., a naturally-occurring or wild-type mRNA sequence encoding an immunogenic protein or polypeptide). In some embodiments, a codon optimized sequence shares less than 85% sequence identity to a naturally-occurring or wild-type sequence (e.g., a naturally-occurring or wild-type mRNA sequence encoding an immunogenic protein or polypeptide). In some embodiments, a codon optimized sequence shares less than 80% sequence identity to a naturally-occurring or wild-type sequence (e.g., a naturally-occurring or wild-type mRNA sequence encoding an immunogenic protein or polypeptide). In some embodiments, a codon optimized sequence shares less than 75% sequence identity to a naturally-occurring or wild-type sequence (e.g., a naturally-occurring or wild-type mRNA sequence encoding an immunogenic protein or polypeptide).

In some embodiments, the nucleic acid encoding an immunogenic protein or polypeptide comprises one or more chemical modifications. The terms "chemical modification" and "chemically modified" refer to modification with respect to adenosine (A), guanosine (G), uridine (U), thymidine (T) or cytidine (C) ribonucleosides or deoxyribonucleosides in at least one of their position, pattern, percent or population.

In some embodiments, the nucleic acids (e.g., DNA or RNA) comprise various (more than one) different modifications. In some embodiments, a particular region of a nucleic acid (e.g., DNA or RNA) contains one, two or more (optionally different) nucleoside or nucleotide modifications. In some embodiments, a modified nucleic acid (e.g., DNA or RNA), introduced to a cell or organism, exhibits reduced degradation in the cell or organism, respectively, relative to an unmodified nucleic acid. In some embodiments, a modified nucleic acid (e.g., DNA or RNA), introduced into a cell or organism, may exhibit reduced immunogenicity in the cell or organism, respectively (e.g., a reduced innate response).

Modified nucleic acid (e.g., DNA or RNA) may comprise modifications that are naturally-occurring, non-naturally-occurring or the polynucleotide may comprise a combination of naturally-occurring and non-naturally-occurring modifications. Polynucleotides may include any useful modification, for example, of a sugar, a nucleobase, or an internucleoside linkage (e.g., to a linking phosphate, to a phosphodiester linkage or to the phosphodiester backbone). Modified nucleic acid (e.g., DNA or RNA), in some embodiments, comprise non-natural modified nucleotides that are introduced during synthesis or post-synthesis of the polynucleotides to achieve desired functions or properties. The modifications may be present on an internucleotide linkages, purine or pyrimidine bases, or sugars. The modification may be introduced with chemical synthesis or with a polymerase enzyme at the terminal of a chain or anywhere else in the chain. Any of the regions of a nucleic acid may be chemically modified.

In some embodiments, a chemically modified nucleic acid comprises one or more modified nucleosides. A "nucleoside" refers to a compound containing a sugar molecule (e.g., a pentose or ribose) or a derivative thereof in combination with an organic base (e.g., a purine or pyrimidine) or a derivative thereof (also referred to herein as "nucleobase"). A nucleotide" refers to a nucleoside, including a phosphate group. Modified nucleotides may by synthesized by any useful method, such as, for example, chemically, enzymatically, or recombinantly, to include one or more modified or non-natural nucleosides. Polynucleotides may comprise a region or regions of linked nucleosides. Such regions may have variable backbone linkages. The linkages may be standard phosphodiester linkages, in which case the polynucleotides would comprise regions of nucleotides.

In some embodiments, a modified nucleobase is a modified uridine. Exemplary nucleobases and nucleosides having a modified cytosine include N4-acetyl-cytidine (ac4C), 5-methyl-cytidine (m5C), 5-halo-cytidine (e.g., 5-iodo-cytidine), 5-hydroxymethyl-cytidine (hm5C), 1-methyl-pseudoisocytidine, 2-thio-cytidine (s2C), and 2-thio-5-methyl-cytidine.

In some embodiments, a modified nucleobase is a modified uridine. Exemplary nucleobases and In some embodiments, a modified nucleobase is a modified cytosine. nucleosides having a modified uridine include 5-cyano uridine, and 4'-thio uridine.

In some embodiments, a modified nucleobase is a modified adenine. Exemplary nucleobases and nucleosides having a modified adenine include 7-deaza-adenine, 1-methyl-adenosine (m1A), 2-methyl-adenine (m2A), and N6-methyl-adenosine (m6A).

In some embodiments, a modified nucleobase is a modified guanine. Exemplary nucleobases and nucleosides having a modified guanine include inosine (I), 1-methyl-inosine (m1I), wyosine (imG), methylwyosine (mimG), 7-deaza-guanosine, 7-cyano-7-deaza-guanosine (preQ0), 7-aminomethyl-7-deaza-guanosine (preQ1), 7-methyl-guanosine (m7G), 1-methyl-guanosine (m1G), 8-oxo-guanosine, 7-methyl-8-oxo-guanosine.

In some embodiments, the antigen of the present disclosure is from a microbial pathogen, e.g., from a bacterium, *mycobacterium*, fungus, a virus, parasite, or prion. For example, the antigen may comprise a protein or polypeptide, or a nucleic acid encoding the protein or polypeptide from the microbial pathogen. In some embodiments, the antigen may comprise a microbial pathogen (e.g., a bacterial cell, a viral particle, or a fungus cell). In some embodiments, the microbial pathogen cell is live or killed. In some embodiments, the microbial pathogen is attenuated its pathogenicity. An attenuated microbial pathogen may elicit immune response but does not cause the disease that a wild-type microbial pathogen would cause.

Exemplary, non-limiting bacterial taxa, species, and strains, suitable for use in some embodiments of this disclosure include: *Escherichia* spp., *Enterobacter* spp. (e.g., *Enterobacter cloacae*), *Salmonella* spp. (e.g., *Salmonella enteritidis, Salmonella typhi*), *Shigella* spp., *Pseudomonas* spp. (e.g., *Pseudomonas aeruginosa, Pseudomonas pachastrellae, Pseudomonas stutzeri*), *Moraxella* spp. (e.g., *Moraxella catarrhalis*), *Neisseria* spp. (e.g., *Neisseria gonorrhoeae, Neisseria meningitidis*), *Helicobacter* spp., (e.g., *Helicobacter pylori*) *Stenotrophomonas* spp., *Vibrio* spp. (e.g., *Vibrio cholerae*), *Legionella* spp. (*Legionella pneumophila*), *Hemophilus* spp. (e.g., *Hemophilus influenzae*), *Klebsiella* spp. (e.g., *Klebsiella pneumoniae*), *Proteus* spp. (e.g., *Proteus mirabilis*), *Serratia* spp. (*Serratia marc-* escens), *Streptococcus* spp., *Staphylococcus* spp., *Corynebacterium* spp., *Listeria* spp., and *Clostridium* spp., *Bacillus* spp. (e.g., *Bacillus anthracis*) *Bordetella* spp. (e.g., *Bordetella pertussis*); *Borrelia* spp. (e.g., *Borrelia burgdorferi*); *Brucella* spp. (e.g., *Brucella abortus*, *Brucella canis*, *Brucella melitensis*, *Brucella suis*); *Campylobacter* spp. (e.g., *Campylobacter jejuni*); *Chlamydia* spp. and *Chlamydophila* spp. (e.g., *Chlamydia pneumoniae*, *Chlamydia trachomatis*, *Chlamydophila psittaci*); *Clostridium* spp. (e.g., *Clostridium botulinum*, *Clostridium difficile*, *Clostridium perfringens*, *Clostridium tetani*); *Corynebacterium* spp. (e.g., *Corynebacterium diphtheriae*); *Enterococcus* spp. (e.g., *Enterococcus faecalis*, *Enterococcus faecium*); *Escherichia* spp. (e.g., *Escherichia coli*, Enterotoxic *E. coli*, enteropathogenic *E. coli*; *E. coli* O157: H7); *Francisella* spp. (e.g., *Francisella tularensis*); *Haemophilus* spp. (e.g., *Haemophilus influenzae*); *Helicobacter* spp. (e.g., *Helicobacter pylori*); *Legionella* spp. (e.g., *Legionella pneumophila*); *Leptospira* spp. (e.g., *Leptospira interrogans*); *Listeria* spp. (e.g., *Listeria monocytogenes*); *Mycobacterium* spp. (e.g., *Mycobacterium leprae*, *Mycobacterium tuberculosis*, *Mycobacterium ulcerans*); *Mycoplasma* spp. (e.g., *Mycoplasma pneumoniae*); *Neisseria* spp. (e.g., *Neisseria gonorrhoeae*, *Neisseria meningitidis*); *Pseudomonas* spp. (e.g., *Pseudomonas aeruginosa*); *Rickettsia* spp. (e.g., *Rickettsia rickettsii*); *Salmonella* spp. (e.g., *Salmonella typhi*, *Salmonella typhimurium*); *Shigella* spp. (e.g., *Shigella sonnei*); *Staphylococcus* spp. (e.g., *Staphylococcus aureus*, *Staphylococcus epidermidis*, *Staphylococcus saprophyticus*); *Streptococcus* spp. (e.g., *Streptococcus agalactiae*, *Streptococcus pneumoniae*, *Streptococcus pyogenes*); *Treponema* spp. (e.g., *Treponema pallidum*); *Pseudodiomarina* spp. (e.g., *P. maritima*); *Marinobacter* spp. (e.g., *Marinobacter hydrocarbonoclasticus*, *Marinobacter vinifirmus*) *Alcanivorax* spp. (e.g., *alcanivorax dieselolei*); *Acetinobacter* spp. (e.g., *A. venetianus*); *Halomonas* spp. (e.g., *H. shengliensis*); *Labrenzia* spp.; *Microbulifer* spp. (e.g., *M. schleiferi*); *Shewanella* spp. (e.g., *S. algae*); *Vibrio* spp. (e.g., *Vibrio cholerae*, *Vibrio alginolyticus*, *Vibrio hepatarius*); and *Yersinia* spp. (e.g., *Yersinia pestis*).

In some embodiments, the bacterium is *Bacillus anthracis* (causing anthrax), *Bordetella pertussis* (causing whooping cough), *Corynebacterium diphtheriae* (causing diphtheria), *Clostridium tetani* (causing tetanus), *Haemophilus influenzae* type b, pneumococcus (causing pneumococcal infections), Staphylococci spp. (including Group A or B streptococci), *Mycobacterium tuberculosis*, *Neiserria meningitidis* (causing meningococcal disease), *Salmonella typhi* (causing typhoid), *Vibrio cholerae* (causing Cholera), or *Yersinia pestis* (causing plague).

In some embodiments, the antigen is derived from a Gram-negative bacterium. In some embodiments, the antigen is a lipopolysaccharide endotoxin (LPS) from a Gram-negative bacterium. Non-limiting examples of gram-negative bacterial species include: *Neisseria* species including *Neisseria gonorrhoeae* and *Neisseria meningitidis*, *Branhamella* species including *Branhamella catarrhalis*, *Escherichia* species including *Escherichia coli*, *Enterobacter* species, *Proteus* species including *Proteus mirabilis*, *Pseudomonas* species including *Pseudomonas aeruginosa*, *Pseudomonas mallei*, and *Pseudomonas pseudomallei*, *Klebsiella* species including *Klebsiella pneumoniae*, *Salmonella* species, *Shigella* species, *Serratia* species, *Acinetobacter* species; *Haemophilus* species including *Haemophilus influenzae* and *Haemophilus ducreyi*; *Brucella* species, *Yersinia* species including *Yersinia pestis* and *Yersinia enterocolitica*, *Francisella* species including *Francisella tularensis*, *Pasteurella* species including *Pasteurella multocida*, *Vibrio cholerae*,

*Flavobacterium* species, *meningosepticum*, *Campylobacter* species including *Campylobacter jejuni*, *Bacteroides* species (oral, pharyngeal) including *Bacteroides fragilis*,

*Fusobacterium* species including *Fusobacterium nucleatum*, *Calymmatobacterium granulomatis* *Streptobacillus* species including *Streptobacillus moniliformis*, *Legionella* species including *Legionella pneumophila*.

In some embodiments, the antigen is derived from a Gram-positive bacterium. Exemplary Gram-positive bacteria include, but are not limited to, *Staphylococcus* spp., *Streptococcus* spp., *Micrococcus* spp., *Peptococcus* spp., *Peptostreptococcus* spp., *Enterococcus* spp., *Bacillus* spp., *Clostridium* spp., *Lactobacillus* spp., *Listeria* spp., *Erysipelothrix* spp., *Propionibacterium* spp., *Eubacterium* spp., *Corynebacterium* spp., *Capnocytophaga* spp., *Bifidobacterium* spp., and *Gardnerella* spp. In some embodiments, the Gram-positive bacteria is a bacteria of the phylum Firmicutes. In some embodiments, the Gram-positive bacteria is *Streptococcus*.

Other types of bacteria include acid-fast bacilli, spirochetes, and actinomycetes. Examples of acid-fast bacilli include *Mycobacterium* species including *Mycobacterium tuberculosis* and *Mycobacterium leprae*. Examples of spirochetes include *Treponema* species including *Treponema pallidum*, *Treponema pertenue*, *Borrelia* species including *Borrelia burgdorferi* (Lyme disease), and *Borrelia recurrentis*, and *Leptospira* species. Examples of actinomycetes include: *Actinomyces* species including *Actinomyces israelii*, and *Nocardia* species including *Nocardia asteroides*.

Examples of viruses include but are not limited to: Retroviruses, human immunodeficiency viruses including HIV-1, HDTV-III, LAVE, HTLV-III/LAV, HIV-III, HIV-LP, Cytomegaloviruses (CMV), Picornaviruses, polio viruses, hepatitis A virus, enteroviruses, human Coxsackie viruses, rhinoviruses, echoviruses, Calciviruses, Togaviruses, equine encephalitis viruses, rubella viruses, Flaviruses, dengue viruses, encephalitis viruses, yellow fever viruses, Coronaviruses, Rhabdoviruses, vesicular stomatitis viruses, rabies viruses, Filoviruses, ebola virus, Paramyxoviruses, parainfluenza viruses, mumps virus, measles virus, respiratory syncytial virus (RSV), Orthomyxoviruses, influenza viruses, Bungaviruses, Hantaan viruses, phleboviruses and Nairo viruses, Arena viruses, hemorrhagic fever viruses, reoviruses, orbiviruses, rotaviruses, Birnaviruses, Hepadnaviruses, Hepatitis B virus, parvoviruses, Papovaviridae, papilloma viruses, polyoma viruses, Adenoviruses, Herpesviruses including herpes simplex virus 1 and 2, varicella zoster virus, Poxviruses, variola viruses, vaccinia viruses, Irido viruses, African swine fever virus, delta hepatitis virus, non-A, non-B hepatitis virus, Hepatitis C, Norwalk viruses, astroviruses, and unclassified viruses. In some embodiments, the virus is adenovirus, enterovirus such as poliomyelitis (polio), Ebola virus, herpes viruses such as herpes simplex virus, cytomegalovirus and varicella-zoster (chickenpox and shingles), measles, mumps, rubella, hepatitis-A, -B, or -C, human papilloma virus, Influenza virus, rabies, Japanese encephalitis, rotavirus, human immunodeficiency virus (HIV), respiratory syncytial virus (RSV), smallpox, yellow fever, or Zika Virus.

In some embodiments, the antigen comprises a viral protein and/or a nucleic acid encoding a viral protein (e.g., a viral structural or non-structural protein). In some embodiments, the antigen comprises a nucleic acid encoding the viral genome. In some embodiments, the viral genome is modified to produce a modified virus that is attenuated.

Examples of fungus include, but are not limited to: *Cryptococcus* species including *Crytococcus neoformans*, *Histoplasma* species including *Histoplasma capsulatum*, *Coccidioides* species including *Coccidiodes immitis*, *Paracoccidioides* species including *Paracoccidioides brasiliensis*, *Blastomyces* species including *Blastomyces dermatitidis*, *Chlamydia* species including *Chlamydia trachomatis*, *Candida* species including *Candida albicans*, *Sporothrix* species including *Sporothrix schenckii*, *Aspergillus* species, and fungi of mucormycosis. In some embodiments, the fungus is *Candida* spp., *Aspergillus* spp., *Cryptococcus* spp., Mucormycete, *Blastomyces dermatitidis* (causing blastomycosis), or endemic mycosis causing fungus such as *Histoplasma capsulatum* (causing histoplasmosis), or *Sporothrix schenckii* (causing sporotrichosis).

Other infectious organisms include, without limitation: parasites, Parasites include *Plasmodium* species, such as *Plasmodium* species including *Plasmodium falciparum*, *Plasmodium malariae*, *Plasmodium ovale*, and *Plasmodium vivax* and *Toxoplasma gondii*. Blood-borne and/or tissues parasites include *Plasmodium*, species, *Babesia* species including *Babesia microti* and *Babesia divergens*. *Leishmania* species including *Leishmania tropica*, *Leishmania* species, *Leishmania brasiliensis*, *Leishmania donovani*, *Trypanasoma* species including *Trypanosoma gambiense*, *Trypanosoma rhodesiense* (African sleeping sickness), and *Trypanosoma cruzi* (Chagas' disease). In some embodiments, the parasite is *Plasmodium* spp., *Leishmania*, or a helminth.

Other medically relevant microorganisms have been described extensively in the literature, e.g., see C. G. A Thomas, *Medical Microbiology*, Bailliere Tindall, Great Britain 1983, incorporated herein by reference.

In some embodiments, the antigen of the present disclosure comprises a cancer-specific antigen and/or a nucleic acid encoding such. A "cancer-specific antigen" refers to a protein that is specifically expressed or upregulated in a cancer cell, as compared to non-cancerous cells of the same origin. A cancer-specific antigen, or epitopes derived therefrom, can be recognized by the immune system to induce a immune response against the cancer. Classes of proteins that may be cancer-specific antigen include, without limitation: enzymes, receptors, and transcription factors.

A large number of proteins that specifically express in cancer cells or are upregulated in cancer cells have been identified (Hassane et al., Holland-Frei Cancer Medicine. 6th edition, incorporated herein by reference). The known tumor specific antigens are classified into different classes: cancer-testis antigens (e.g., MAGE family members or NY-ESO-1), differentiation antigens (e.g., tyrosinase and Melan-A/MART-1 for melanoma, and PSA for prostate cancer), overexpressed cancer-specific antigens (e.g., Her-2/neu, Survivin, Telomerase and WT1), cancer-specific antigens arising from mutations of normal genes (e.g., mutated β-catenin or CDK4), cancer-specific antigens arising from abnormal post-translational modifications (e.g., altered glycosylation patterns) that lead to novel epitopes in tumors (e.g., MUC1), and oncoviral proteins (e.g., human papilloma type 16 virus proteins, E6 and E7). In some embodiments, the tumor-specific antigen is expressed in a broad range of different types of cancers. In some embodiments, the tumor-specific antigen is expressed only in one or a few types of cancers.

In some embodiments, the antigen comprises a fragment or an epitope derived from a cancer-specific antigen and/or a nucleic acid encoding such. For example, the fragment or an epitope derived from a cancer-specific antigen may be 5-40 amino acids long. In some embodiments, the fragment or an epitope derived from a cancer-specific antigen is 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 amino acids long.

In some embodiments, the fragment or epitope derived from a cancer-specific antigen is a heteroclitic epitope. A "heteroclitic epitope" refers to an altered version of an endogenous peptide sequence (i.e., an analog) from a cancer-specific antigen engineered to elicit potent immune reactions. Heteroclitic epitopes have increased stimulatory capacity or potency for a specific T cell, as measured by increased responses to a given dose, or by a requirement of lesser amounts to achieve the same response and therefore provide benefit as vaccine components since these epitopes induce T cell responses stronger than those induced by the native epitope.

In some embodiments, the heteroclitic epitope comprises modifications, e.g., amino acid substitutions, as compared to the native sequence in the cancer-specific antigen. In some embodiments, the heteroclitic epitope comprises more than one amino acid substitutions (e.g., 2, 3, 4, 5, or more) compared to the native sequence of the cancer-specific antigen it is derived from. In some embodiments, a heteroclitic epitope is at least 60%, at least 70%, at least 80%, at least 90%, at least 98%, or at least 99% identical to the native sequence that it is derived from. In some embodiments, a heteroclitic epitope is 60%, 65%, 70%, 75%, 80%, 85%, 90%, 95%, 98%, or 99% identical to the native sequence that it is derived from.

In some embodiments, a heteroclitic epitope is more immunogenic than a peptide of its native sequence. For example, a heteroclitic epitope may be at least 30% more immunogenic (i.e., induces a stronger immune response) than its corresponding native peptide. In some embodiments, a heteroclitic epitope may be at least 30%, at least 40%, at least 50%, at least 60%, at least 70%, at least 80%, at least 90%, at least 100%, at least 2-fold, at least 3-fold, at least 4-fold, at least 5-fold, at least 6-fold, at least 7-fold, at least 8-fold, at least 9-fold, at least 10-fold, at least 20-fold, at least 30-fold, at least 40-fold, at least 50-fold, at least 60-fold, at least 70-fold, at least 80-fold, at least 90-fold, at least 100-fold, or more immunogenic than its corresponding native peptide.

In some embodiments, the fragment or epitope derived from a cancer-specific antigen is a cryptic epitope. A "cryptic epitope" refers to an epitope derived from a cancer-specific antigen that does not necessarily undergo antigen processing/presentation and are 'hidden' from immune recognition. Cryptic epitopes usually appear in very low concentration on APC and do not delete auto-reactive T cells. Cryptic epitopes are not presented for recognition by T cells unless they are produced in unusually large concentrations or unless they are freed from the configuration of their native antigen. Cryptic epitopes derived from cancer-specific antigens may be used to break the tolerance of T cells to the tumor and induce potent immune response against the tumor. Such principles have been described in Pardoll, et al., PNAS, Vol. 96, pp. 5340-5342 (1999), the entire contents of which are incorporated herein by reference.

In some embodiments, the cryptic epitope is generated from translation of a non-coding region of the cancer-specific antigen gene or translation of a different reading frame of a coding region of the cancer-specific antigen. A cryptic epitope may be more immunogenic (i.e., induces a stronger immune response) than any native peptide derived from the cancer-specific antigen. For example, a cryptic epitope may be at least 30% more immunogenic than any native peptide derived from the cancer-specific antigen. In some embodiments, a cryptic epitope is at least 30%, at least 40%, at least 50%, at least 60%, at least 70%, at least 80%, at least 90%, at least 100%, at least 2-fold, at least 3-fold, at least 4-fold, at least 5-fold, at least 6-fold, at least 7-fold, at least 8-fold, at least 9-fold, at least 10-fold, at least 20-fold, at least 30-fold, at least 40-fold, at least 50-fold, at least 60-fold, at least 70-fold, at least 80-fold, at least 90-fold, at least 100-fold, or more immunogenic than any native peptide derived from the cancer-specific antigen. One skilled in the art is familiar with how to assess the immune response induced by an antigen, e.g., measuring antibody titers.

In some embodiments, the cancer-specific antigen is a neoantigen. A "neoantigen" refers to an antigen generated via random somatic mutations occurring in cancer cells and are thus specific to the lineage of cancer cells it is derived from. Neoantigens are regarded in the art to be responsible for the immunogenicity of tumors ((Srivastava et al., 1993, Duan et al., 2009; van der Bruggen et al., 2013, incorporated herein by reference), and mathematic modeling has predicted the existence of tens to hundreds of neoepitopes (epitopes derived from neoantigens) in individual human tumors (Srivastava 2009, incorporated herein by reference). The recent revolution in high-throughput DNA sequencing and accompanying bioinformatics approaches has finally made it possible to actually identify the individually specific neoepitopes in individual cancers.

In some embodiments, the antigen described herein is an antigen designed to provide broad heterologous protection against a range of pathogens. Heterologous immunity refers to the phenomenon whereby a history of an immune response against a stimulus or pathogen can provide a level of immunity to a second unrelated stimulus or pathogen (e.g., as described in Chen et al., Virology 2015 482: 89-97, incorporated herein by reference). For example, an antigen that induces cross-reactive memory CD8+ T cells against multiple unrelated viruses such as influenza A and Epstein-Barr Virus (EBV), as described in Watkin et al., J Allerg Clin Immunol 2017 October; 140(4) 1206-1210, incorporated herein by reference. In some embodiments, the adjuvantation system described in induce and/or enhance the heterologous protection.

Polypeptide or polynucleotide molecules of the present disclosure may share a certain degree of sequence similarity or identity with reference molecules (e.g., reference polypeptides or reference polynucleotides), for example, wild-type molecules. The term "identity" as known in the art, refers to a relationship between the sequences of two or more polypeptides or polynucleotides, as determined by comparing the sequences. In the art, identity also means the degree of sequence relatedness between them as determined by the number of matches between strings of two or more amino acid residues or nucleic acid residues. Identity measures the percent of identical matches between the smaller of two or more sequences with gap alignments (if any) addressed by a particular mathematical model or computer program (e.g., "algorithms"). Identity of related peptides can be readily calculated by known methods. "% identity" as it applies to polypeptide or polynucleotide sequences is defined as the percentage of residues (amino acid residues or nucleic acid residues) in the candidate amino acid or nucleic acid sequence that are identical with the residues in the amino acid sequence or nucleic acid sequence of a second sequence after aligning the sequences and introducing gaps, if necessary, to achieve the maximum percent identity. Methods and computer programs for the alignment are well known in the art. It is understood that identity depends on a calculation of percent identity but may differ in value due to gaps and penalties introduced in the calculation. Generally, variants of a particular polynucleotide or polypeptide have at least 40%, 45%, 50%, 55%, 60%, 65%, 70%, 75%, 80%, 85%, 90%, 91%, 92%, 93%, 94%, 95%, 96%, 97%, 98%, 99% but less than 100% sequence identity to that particular reference polynucleotide or polypeptide as determined by sequence alignment programs and parameters described herein and known to those skilled in the art. Such tools for alignment include those of the BLAST suite (Stephen F. Altschul, et al (1997), "Gapped BLAST and PSI-BLAST: a new generation of protein database search programs", Nucleic Acids Res. 25:3389-3402). Another popular local alignment technique is based on the Smith-Waterman algorithm (Smith, T. F. & Waterman, M. S. (1981) "Identification of common molecular subsequences." J. Mol. Biol. 147: 195-197.) A general global alignment technique based on dynamic programming is the Needleman-Wunsch algorithm (Needleman, S. B. & Wunsch, C. D. (1970) "A general method applicable to the search for similarities in the amino acid sequences of two proteins." J. Mol. Biol. 48:443-453.). More recently a Fast Optimal Global Sequence Alignment Algorithm (FOGSAA) has been developed that purportedly produces global alignment of nucleotide and protein sequences faster than other optimal global alignment methods, including the Needleman-Wunsch algorithm. Other tools are described herein, specifically in the definition of "identity" below.

As used herein, the term "homology" refers to the overall relatedness between polymeric molecules, e.g. between nucleic acid molecules (e.g. DNA molecules and/or RNA molecules) and/or between polypeptide molecules. Polymeric molecules (e.g. nucleic acid molecules (e.g. DNA molecules and/or RNA molecules) and/or polypeptide molecules) that share a threshold level of similarity or identity determined by alignment of matching residues are termed homologous. Homology is a qualitative term that describes a relationship between molecules and can be based upon the quantitative similarity or identity. Similarity or identity is a quantitative term that defines the degree of sequence match between two compared sequences. In some embodiments, polymeric molecules are considered to be "homologous" to one another if their sequences are at least 25%, 30%, 35%, 40%, 45%, 50%, 55%, 60%, 65%, 70%, 75%, 80%, 85%, 90%, 95%, or 99% identical or similar. The term "homologous" necessarily refers to a comparison between at least two sequences (polynucleotide or polypeptide sequences). Two polynucleotide sequences are considered homologous if the polypeptides they encode are at least 50%, 60%, 70%, 80%, 90%, 95%, or even 99% for at least one stretch of at least 20 amino acids. In some embodiments, homologous polynucleotide sequences are characterized by the ability to encode a stretch of at least 4-5 uniquely specified amino acids. For polynucleotide sequences less than 60 nucleotides in length, homology is determined by the ability to encode a stretch of at least 4-5 uniquely specified amino acids. Two protein sequences are considered homologous if the proteins are at least 50%, 60%, 70%, 80%, or 90% identical for at least one stretch of at least 20 amino acids.

Homology implies that the compared sequences diverged in evolution from a common origin. The term "homolog" refers to a first amino acid sequence or nucleic acid sequence (e.g., gene (DNA or RNA) or protein sequence) that is related to a second amino acid sequence or nucleic acid sequence by descent from a common ancestral sequence. The term "homolog" may apply to the relationship between genes and/or proteins separated by the event of speciation or to the relationship between genes and/or proteins separated by the event of genetic duplication. "Orthologs" are genes (or proteins) in different species that evolved from a common ancestral gene (or protein) by speciation. Typically, orthologs retain the same function in the course of evolution. "Paralogs" are genes (or proteins) related by duplication within a genome. Orthologs retain the same function in the course of evolution, whereas paralogs evolve new functions, even if these are related to the original one.

The term "identity" refers to the overall relatedness between polymeric molecules, for example, between polynucleotide molecules (e.g. DNA molecules and/or RNA molecules) and/or between polypeptide molecules. Calculation of the percent identity of two polynucleic acid sequences, for example, can be performed by aligning the two sequences for optimal comparison purposes (e.g., gaps can be introduced in one or both of a first and a second nucleic acid sequences for optimal alignment and non-identical sequences can be disregarded for comparison purposes). In some embodiments, the length of a sequence aligned for comparison purposes is at least 30%, at least 40%, at least 50%, at least 60%, at least 70%, at least 80%, at least 90%, at least 95%, or 100% of the length of the reference sequence. The nucleotides at corresponding nucleotide positions are then compared. When a position in the first sequence is occupied by the same nucleotide as the corresponding position in the second sequence, then the molecules are identical at that position. The percent identity between the two sequences is a function of the number of identical positions shared by the sequences, taking into account the number of gaps, and the length of each gap, which needs to be introduced for optimal alignment of the two sequences. The comparison of sequences and determination of percent identity between two sequences can be accomplished using a mathematical algorithm. For example, the percent identity between two nucleic acid sequences can be determined using methods such as those described in Computational Molecular Biology, Lesk, A. M., ed., Oxford University Press, New York, 1988; Biocomputing: Informatics and Genome Projects, Smith, D. W., ed., Academic Press, New York, 1993; Sequence Analysis in Molecular Biology, von Heinje, G., Academic Press, 1987; Computer Analysis of Sequence Data, Part I, Griffin, A. M., and Griffin, H. G., eds., Humana Press, New Jersey, 1994; and Sequence Analysis Primer, Gribskov, M. and Devereux, J., eds., M Stockton Press, New York, 1991; each of which is incorporated herein by reference. For example, the percent identity between two nucleic acid sequences can be determined using the algorithm of Meyers and Miller (CABIOS, 1989, 4:11-17), which has been incorporated into the ALIGN program (version 2.0) using a PAM120 weight residue table, a gap length penalty of 12 and a gap penalty of 4. The percent identity between two nucleic acid sequences can, alternatively, be determined using the GAP program in the GCG software package using an NWSgapdna.CMP matrix. Methods commonly employed to determine percent identity between sequences include, but are not limited to those disclosed in Carillo, H., and Lipman, D., SIAM J Applied Math., 48:1073 (1988); incorporated herein by reference. Techniques for determining identity are codified in publicly available computer programs. Exemplary computer software to determine homology between two sequences include, but are not limited to, GCG program package, Devereux, J., et al., Nucleic Acids Research, 12(1), 387 (1984)), BLASTP, BLASTN, and FASTA Altschul, S. F. et al., J. Molec. Biol., 215, 403 (1990)).

In some embodiments, the vaccine composition described herein are formulated for administration to a subject. In some embodiments, the vaccine composition is formulated or administered in combination with one or more pharmaceutically-acceptable excipients. In some embodiments, vaccine compositions comprise at least one additional active substances, such as, for example, a therapeutically-active substance, a prophylactically-active substance, or a combination of both. Vaccine compositions may be sterile, pyrogen-free or both sterile and pyrogen-free. General considerations in the formulation and/or manufacture of pharmaceutical agents, such as vaccine compositions, may be found, for example, in Remington: The Science and Practice of Pharmacy 21st ed., Lippincott Williams & Wilkins, 2005 (incorporated herein by reference in its entirety).

Formulations of the vaccine compositions described herein may be prepared by any method known or hereafter developed in the art of pharmacology. In general, such preparatory methods include the step of bringing the antigen and/or the adjuvant (e.g., STING ligand alone or STING ligand and alum) into association with an excipient and/or one or more other accessory ingredients, and then, if necessary and/or desirable, dividing, shaping and/or packaging the product into a desired single- or multi-dose unit.

Relative amounts of the antigen, the adjuvant, the pharmaceutically acceptable excipient, and/or any additional ingredients in a pharmaceutical composition in accordance with the disclosure will vary, depending upon the identity, size, and/or condition of the subject treated and further depending upon the route by which the composition is to be administered. By way of example, the composition may comprise between 0.1% and 100%, e.g., between 0.5 and 50%, between 1-30%, between 5-80%, at least 80% (w/w) active ingredient.

In some embodiments, the vaccine composition described herein are formulated using one or more excipients to: (1) increase stability; (2) increase cell transfection; (3) permit the sustained or delayed release (e.g., from a depot formulation); (4) alter the biodistribution (e.g., target to specific tissues or cell types); (5) increase the translation of encoded protein in vivo; and/or (6) alter the release profile of encoded protein (antigen) in vivo. In addition to traditional excipients such as any and all solvents, dispersion media, diluents, or other liquid vehicles, dispersion or suspension aids, surface active agents, isotonic agents, thickening or emulsifying agents, preservatives, excipients can include, without limitation, lipidoids, liposomes, lipid nanoparticles, polymers, lipoplexes, core-shell nanoparticles, peptides, proteins, cells transfected with DNA or RNA vaccines (e.g., for transplantation into a subject), hyaluronidase, nanoparticle mimics and combinations thereof.

In some embodiments, the vaccine composition is formulated in an aqueous solution. In some embodiments, the vaccine composition is formulated in a nanoparticle. In some embodiments, the vaccine composition is formulated in a lipid nanoparticle. In some embodiments, the vaccine composition is formulated in a lipid-polycation complex, referred to as a lipid nanoparticle. The formation of the lipid nanoparticle may be accomplished by methods known in the art and/or as described in U.S. Pub. No. 20120178702, incorporated herein by reference. As a non-limiting example, the polycation may include a cationic peptide or a polypeptide such as, but not limited to, polylysine, polyornithine and/or polyarginine and the cationic peptides described in International Pub. No. WO2012013326 or US Patent Pub. No. US20130142818; each of which is incorporated herein by reference. In some embodiments, the vaccine composition is formulated in a lipid nanoparticle that includes a non-cationic lipid such as, but not limited to, cholesterol or dioleoyl phosphatidylethanolamine (DOPE).

A lipid nanoparticle formulation may be influenced by, but not limited to, the selection of the ionizable lipid component, the degree of ionizable lipid saturation, the nature of the PEGylation, ratio of all components and biophysical parameters such as size. In one example by Semple et al. (Nature Biotech. 2010 28:172-176; incorporated herein by reference), the lipid nanoparticle formulation is composed of 57.1% cationic lipid, 7.1% dipalmitoylphosphatidylcholine, 34.3% cholesterol, and 1.4% PEG-c-DMA. As another example, changing the composition of the cationic lipid can more effectively deliver siRNA to various antigen presenting cells (Basha et al. Mol Ther. 2011 19:2186-2200; incorporated herein by reference).

In some embodiments, lipid nanoparticle formulations may comprise 35 to 45% ionizable cationic lipid, 40% to 50% ionizable cationic lipid, 50% to 60% ionizable cationic lipid and/or 55% to 65% ionizable cationic lipid. In some embodiments, the ratio of lipid to RNA (e.g., mRNA) in lipid nanoparticles may be 5:1 to 20:1, 10:1 to 25:1, 15:1 to 30:1 and/or at least 30:1.

In some embodiments, the ratio of PEG in the lipid nanoparticle formulations may be increased or decreased and/or the carbon chain length of the PEG lipid may be modified from C14 to C18 to alter the pharmacokinetics and/or biodistribution of the lipid nanoparticle formulations. As a non-limiting example, lipid nanoparticle formulations may contain 0.5% to 3.0%, 1.0% to 3.5%, 1.5% to 4.0%, 2.0% to 4.5%, 2.5% to 5.0% and/or 3.0% to 6.0% of the lipid molar ratio of PEG-c-DOMG (R-3-[(ω-methoxy-poly(ethyleneglycol)2000)carbamoyl)]-1,2-dimyristyloxypropyl-3-amine) (also referred to herein as PEG-DOMG) as compared to the cationic lipid, DSPC and cholesterol. In some embodiments, the PEG-c-DOMG may be replaced with a PEG lipid such as, but not limited to, PEG-DSG (1,2-Distearoyl-sn-glycerol, methoxypolyethylene glycol), PEG-DMG (1,2-Dimyristoyl-sn-glycerol) and/or PEG-DPG (1,2-Dipalmitoyl-sn-glycerol, methoxypolyethylene glycol). The cationic lipid may be selected from any lipid known in the art such as, but not limited to, DLin-MC3-DMA, DLin-DMA, C12-200 and DLin-KC2-DMA.

In some embodiments, a vaccine formulation described herein is a nanoparticle that comprises at least one lipid (termed a "lipid nanoparticle" or "LNP"). The lipid may be selected from, but is not limited to, DLin-DMA, DLin-K-DMA, 98N12-5, C12-200, DLin-MC3-DMA, DLin-KC2-DMA, DODMA, PLGA, PEG, PEG-DMG, PEGylated lipids and amino alcohol lipids. In some embodiments, the lipid may be a cationic lipid such as, but not limited to, DLin-DMA, DLin-D-DMA, DLin-MC3-DMA, DLin-KC2-DMA, DODMA and amino alcohol lipids. The amino alcohol cationic lipid may be the lipids described in and/or made by the methods described in US Patent Publication No. US20130150625, incorporated herein by reference. As a non-limiting example, the cationic lipid may be 2-amino-3-[(9Z,12Z)-octadeca-9,12-dien-1-yloxy]-2-{[(9Z,2Z)-octadeca-9,12-dien-1-yloxy]methyl}propan-1-ol (Compound 1 in US20130150625); 2-amino-3-[(9Z)-octadec-9-en-1-yloxy]-2-{[(9Z)-octadec-9-en-1-yloxy]methyl}propan-1-ol (Compound 2 in US20130150625); 2-amino-3-[(9Z,12Z)-octadeca-9,12-dien-1-yloxy]-2-[(octyloxy)methyl]propan-1-ol (Compound 3 in US20130150625); and 2-(dimethylamino)-3-[(9Z,12Z)-octadeca-9,12-dien-1-yloxy]-2-{[(9Z,12Z)-octadeca-9,12-dien-1-yloxy]methyl}propan-1-ol (Compound 4 in US20130150625); or any pharmaceutically acceptable salt or stereoisomer thereof.

Lipid nanoparticle formulations typically comprise a lipid, in particular, an ionizable cationic lipid, for example, 2,2-dilinoleyl-4-dimethylaminoethyl-[1,3]-dioxolane (DLin-KC2-DMA), dilinoleyl-methyl-4-dimethylaminobutyrate (DLin-MC3-DMA), or di((Z)-non-2-en-1-yl) 9-((4-(dimethylamino)butanoyl)oxy)heptadecanedioate (L319), and further comprise a neutral lipid, a sterol and a molecule capable of reducing particle aggregation, for example a PEG or PEG-modified lipid.

In some embodiments, a lipid nanoparticle formulation consists essentially of (i) at least one lipid selected from the group consisting of 2,2-dilinoleyl-4-dimethylaminoethyl-[1,3]-dioxolane (DLin-KC2-DMA), dilinoleyl-methyl-4-dimethylaminobutyrate (DLin-MC3-DMA), and di((Z)-non-2-en-1-yl) 9-((4-(dimethylamino)butanoyl)oxy)heptadecanedioate (L319); (ii) a neutral lipid selected from DSPC, DPPC, POPC, DOPE and SM; (iii) a sterol, e.g., cholesterol; and (iv) a PEG-lipid, e.g., PEG-DMG or PEG-cDMA, in a molar ratio of 20-60% ionizable cationic lipid: 5-25% neutral lipid: 25-55% sterol; 0.5-15% PEG-lipid.

Non-limiting examples of lipid nanoparticle compositions and methods of making them are described, for example, in Semple et al. (2010) Nat. Biotechnol. 28:172-176; Jayarama et al. (2012), Angew. Chem. Int. Ed., 51: 8529-8533; and Maier et al. (2013) Molecular Therapy 21, 1570-1578 (the contents of each of which are incorporated herein by reference in their entirety).

The lipid nanoparticles described herein may be made in a sterile environment by the system and/or methods described in US Patent Publication No. US20130164400, incorporated herein by reference.

In some embodiments, the lipid nanoparticle formulation may be formulated in a nanoparticle such as a nucleic acid-lipid particle described in U.S. Pat. No. 8,492,359, the contents of which are incorporated herein by reference. As a non-limiting example, the lipid nanoparticle may comprise one or more active agents or therapeutic agents; one or more cationic lipids comprising from about 50 mol % to about 85 mol % of the total lipid present in the particle; one or more non-cationic lipids comprising from about 13 mol % to about 49.5 mol % of the total lipid present in the particle; and one or more conjugated lipids that inhibit aggregation of particles comprising from about 0.5 mol % to about 2 mol % of the total lipid present in the particle. The nucleic acid in the nanoparticle may be the polynucleotides described herein and/or are known in the art.

In some embodiments, the lipid nanoparticle formulation may be formulated by the methods described in International Publication Nos. WO2011127255 or WO2008103276, the contents of each of which are herein incorporated by reference in their entirety. As a non-limiting example, the antigen and the adjuvantation system described herein may be encapsulated in LNP formulations as described in WO2011127255 and/or WO2008103276; the contents of each of which are herein incorporated by reference in their entirety.

In some embodiments, lipid nanoparticle formulations described herein may comprise a polycationic composition. As a non-limiting example, the polycationic composition may be selected from formula 1-60 of US Patent Publication No. US20050222064; the content of which is incorporated herein by reference. In another embodiment, the LNP formulations comprising a polycationic composition may be used for the delivery of the modified RNA described herein in vivo and/or in vitro.

In some embodiments, the lipid nanoparticle formulations described herein may additionally comprise a permeability enhancer molecule. Non-limiting permeability enhancer molecules are described in US Patent Publication No. US20050222064; the content of which is incorporated herein by reference.

In some embodiments, the vaccine compositions may be formulated in liposomes such as, but not limited to, DiLa2 liposomes (Marina Biotech, Bothell, Wash.), SMARTICLES® (Marina Biotech, Bothell, Wash.), neutral DOPC (1,2-dioleoyl-sn-glycero-3-phosphocholine) based liposomes (e.g., siRNA delivery for ovarian cancer (Landen et al. Cancer Biology & Therapy 2006 5(12) 1708-1713); incorporated herein by reference) and hyaluronan-coated liposomes (Quiet Therapeutics, Israel).

In some embodiments, the vaccine compositions may be formulated in a lyophilized gel-phase liposomal composition as described in US Publication No. US2012060293, incorporated herein by reference.

In some embodiments, the vaccine compositions described herein may be formulated in lipid nanoparticles having a diameter from about 10 to about 100 nm such as, but not limited to, about 10 to about 20 nm, about 10 to about 30 nm, about 10 to about 40 nm, about 10 to about 50 nm, about 10 to about 60 nm, about 10 to about 70 nm, about 10 to about 80 nm, about 10 to about 90 nm, about 20 to about 30 nm, about 20 to about 40 nm, about 20 to about 50 nm, about 20 to about 60 nm, about 20 to about 70 nm, about 20 to about 80 nm, about 20 to about 90 nm, about 20 to about 100 nm, about 30 to about 40 nm, about 30 to about 50 nm, about 30 to about 60 nm, about 30 to about 70 nm, about 30 to about 80 nm, about 30 to about 90 nm, about 30 to about 100 nm, about 40 to about 50 nm, about 40 to about 60 nm, about 40 to about 70 nm, about 40 to about 80 nm, about 40 to about 90 nm, about 40 to about 100 nm, about 50 to about 60 nm, about 50 to about 70 nm about 50 to about 80 nm, about 50 to about 90 nm, about 50 to about 100 nm, about 60 to about 70 nm, about 60 to about 80 nm, about 60 to about 90 nm, about 60 to about 100 nm, about 70 to about 80 nm, about 70 to about 90 nm, about 70 to about 100 nm, about 80 to about 90 nm, about 80 to about 100 nm and/or about 90 to about 100 nm.

In some embodiments, the lipid nanoparticles may have a diameter from about 10 to 500 nm. In some embodiments, the lipid nanoparticle may have a diameter greater than 100 nm, greater than 150 nm, greater than 200 nm, greater than 250 nm, greater than 300 nm, greater than 350 nm, greater than 400 nm, greater than 450 nm, greater than 500 nm, greater than 550 nm, greater than 600 nm, greater than 650 nm, greater than 700 nm, greater than 750 nm, greater than 800 nm, greater than 850 nm, greater than 900 nm, greater than 950 nm or greater than 1000 nm.

In some embodiments, the vaccine composition is formulated in a liposome. Liposomes are artificially-prepared vesicles which may primarily be composed of a lipid bilayer and may be used as a delivery vehicle for the administration of nutrients and pharmaceutical formulations. Liposomes can be of different sizes such as, but not limited to, a multilamellar vesicle (MLV) which may be hundreds of nanometers in diameter and may contain a series of concentric bilayers separated by narrow aqueous compartments, a small unicellular vesicle (SUV) which may be smaller than 50 nm in diameter, and a large unilamellar vesicle (LUV) which may be between 50 and 500 nm in diameter. Liposome design may include, but is not limited to, opsonins or ligands in order to improve the attachment of liposomes to unhealthy tissue or to activate events such as, but not limited to, endocytosis. Liposomes may contain a low or a high pH in order to improve the delivery of the pharmaceutical formulations.

The formation of liposomes may depend on the physicochemical characteristics such as, but not limited to, the pharmaceutical formulation entrapped and the liposomal ingredients, the nature of the medium in which the lipid vesicles are dispersed, the effective concentration of the entrapped substance and its potential toxicity, any additional processes involved during the application and/or delivery of the vesicles, the optimization size, polydispersity and the shelf-life of the vesicles for the intended application, and the batch-to-batch reproducibility and possibility of large-scale production of safe and efficient liposomal products.

As a non-limiting example, liposomes such as synthetic membrane vesicles may be prepared by the methods, apparatus and devices described in US Patent Publication No. US20130177638, US20130177637, US20130177636, US20130177635, US20130177634, US20130177633, US20130183375, US20130183373 and US20130183372, the contents of each of which are incorporated herein by reference.

In some embodiments, the vaccine compositions described herein may include, without limitation, liposomes such as those formed from 1,2-dioleyloxy-N,N-dimethylaminopropane (DODMA) liposomes, DiLa2 liposomes from Marina Biotech (Bothell, Wash.), 1,2-dilinoleyloxy-3-dimethylaminopropane (DLin-DMA), 2,2-dilinoleyl-4-(2-dimethylaminoethyl)-[1,3]-dioxolane (DLin-KC2-DMA), and MC3 (US20100324120; incorporated herein by reference) and liposomes which may deliver small molecule drugs such as, but not limited to, DOXIL® from Janssen Biotech, Inc. (Horsham, Pa.).

In some embodiments, pharmaceutical compositions described herein may include, without limitation, liposomes such as those formed from the synthesis of stabilized plasmid-lipid particles (SPLP) or stabilized nucleic acid lipid particle (SNALP) that have been previously described and shown to be suitable for oligonucleotide delivery in vitro and in vivo (see Wheeler et al. Gene Therapy. 1999 6:271-281; Zhang et al. Gene Therapy. 1999 6:1438-1447; Jeffs et al. Pharm Res. 2005 22:362-372; Morrissey et al., Nat Biotechnol. 2005 2:1002-1007; Zimmermann et al., Nature. 2006 441:111-114; Heyes et al. J Contr Rel. 2005 107:276-287; Semple et al. Nature Biotech. 2010 28:172-176; Judge et al. J Clin Invest. 2009 119:661-673; deFougerolles Hum Gene Ther. 2008 19:125-132; U.S. Patent Publication No US20130122104; all of which are incorporated herein in their entireties). The original manufacture method by Wheeler et al. was a detergent dialysis method, which was later improved by Jeffs et al. and is referred to as the spontaneous vesicle formation method. The liposome formulations are composed of 3 to 4 lipid components in addition to the polynucleotide. As an example a liposome can contain, but is not limited to, 55% cholesterol, 20% disteroylphosphatidyl choline (DSPC), 10% PEG-S-DSG, and 15% 1,2-dioleyloxy-N,N-dimethylaminopropane (DODMA), as described by Jeffs et al. As another example, certain liposome formulations may contain, but are not limited to, 48% cholesterol, 20% DSPC, 2% PEG-c-DMA, and 30% cationic lipid, where the cationic lipid can be 1,2-distearloxy-N,N-dimethylaminopropane (DSDMA), DODMA, DLin-DMA, or 1,2-dilinolenyloxy-3-dimethylaminopropane (DLenDMA), as described by Heyes et al.

In some embodiments, liposomes may be formulated for targeted delivery. As a non-limiting example, the liposome may be formulated for targeted delivery to the liver. The liposome used for targeted delivery may include, but is not limited to, the liposomes described in and methods of making liposomes described in US Patent Publication No. US20130195967, the contents of which are incorporated herein by reference.

In some embodiments, the antigen and/or the adjuvantation system may be formulated in a cationic oil-in-water emulsion where the emulsion particle comprises an oil core and a cationic lipid which can interact with the polynucleotide anchoring the molecule to the emulsion particle (see International Pub. No. WO2012006380; incorporated herein by reference).

In some embodiments, the antigen and/or the adjuvantation system may be formulated in a water-in-oil emulsion comprising a continuous hydrophobic phase in which the hydrophilic phase is dispersed. As a non-limiting example, the emulsion may be made by the methods described in International Publication No. WO201087791, the contents of which are incorporated herein by reference.

The antigen, the adjuvantation system, and/or optionally the second adjuvant may be formulated using any of the methods described herein or known in the art separately or together. For example, the antigen and the adjuvantation system may be formulated in one lipid nanoparticle or two separately lipid nanoparticles. In some embodiments, the antigen, the adjuvantation system are formulated in the same aqueous solution or two separate aqueous solutions.

Other aspects of the present disclosure provide methods of inducing an immune response to an antigen in a subject in need thereof, the method comprising administering to the subject an effective amount of an antigen and an effective amount of an adjuvantation system comprising a Stimulator of Interferon Genes (STING) ligand (e.g., cGAMP). In some embodiments, the adjuvantation system further comprises alum.

In some embodiments, the adjuvantation system (e.g., comprising STING ligand such as cGAMP alone or STING ligand and alum) is administered separately from the antigen. In some embodiments, the adjuvantation system (e.g., comprising STING ligand such as cGAMP alone or STING ligand and alum) is administered prior to administering the antigen. In some embodiments, the adjuvantation system (e.g., comprising STING ligand such as cGAMP alone or STING ligand and alum) is administered after administering the antigen. In some embodiments, the adjuvantation system (e.g., comprising STING ligand such as cGAMP alone or STING ligand and alum) and the antigen are administered simultaneously. In some embodiment, the adjuvantation system (e.g., comprising STING ligand such as cGAMP alone or STING ligand and alum) and the antigen are administered as an admixture.

A "subject" to which administration is contemplated refers to a human (i.e., male or female of any age group, e.g., pediatric subject (e.g., infant, child, or adolescent) or adult subject (e.g., young adult, middle-aged adult, or senior adult)) or non-human animal. In some embodiments, the non-human animal is a mammal (e.g., primate (e.g., cynomolgus monkey or rhesus monkey), commercially relevant mammal (e.g., cattle, pig, horse, sheep, goat, cat, or dog), or bird (e.g., commercially relevant bird, such as chicken, duck, goose, or turkey)). In some embodiments, the non-human animal is a fish, reptile, or amphibian. The non-human animal may be a male or female at any stage of development. The non-human animal may be a transgenic animal or genetically engineered animal. A "subject in need thereof" refers to a subject (e.g., a human subject or a non-human mammal) in need of treatment of a disease or in need of reducing the risk of developing a disease. In some embodiments, the subject has any of the diseases described herein (e.g., infectious disease, cancer, or allergy). In some embodiments, the subject is at risk of developing any of the diseases described herein (e.g., infectious disease, cancer, or allergy). In some embodiments, administering the antigen and the adjuvantation system described herein (e.g., comprising STING ligand such as cGAMP alone or STING ligand and alum) to a subject having a disease treats the disease (therapeutic use). In some embodiments, administering the antigen and the adjuvantation system described herein (e.g., comprising STING ligand such as cGAMP alone or STING ligand and alum) to a subject at risk of developing a disease reduces the likelihood (e.g., by 20%, 30%, 40%, 50%, 60%, 70%, 80%, 90%, 95%, 99% or more) of the subject developing the disease (prophylactic use).

In some embodiments, the subject is a human subject, e.g., a human neonate, infant, child, adult, or elderly. In particular, the present disclosure demonstrate the immune enhancing effects of the adjuvantation system described herein (e.g., STING ligand alone, or STING ligand formulated with alum) in newborn human subjects. In some embodiments, the STING ligand used in the adjuvantation system for enhancing an immune response in a newborn human subject is cGAMP (e.g., cGAMP alone or cGAMP formulated with alum). A "newborn" refers to a subject that is still in its infancy stage. For different species the infancy stage may be of different length. In some embodiments, the newborn subject is a human newborn. A human newborn refers to a human that is no more than one year of age (e.g., a human subject that is 1 hour, 12 hours, 1 day, 1 week, 1 month, 2 months, 3 months, 4 months, 5 months, 6 months, 7 months, 8 months, 9 months, 10 months, 11 months, or 12 months of age).

In some embodiments, the human newborn is a neonate that is less than 28 days of age at the time the vaccine described herein is administered. In some embodiments, the human neonate is 0-28 days, 0-27 days, 0-26 days, 0-25 days, 0-24 days, 0-23 days, 0-22 days, 0-21 days, 0-20 days, 0-19 days, 0-18 days, 0-17 days, 0-16 days, 0-15 days, 0-14 days, 0-13 days, 0-12 days, 0-11 days, 0-10 days, 0-9 days, 0-8 days, 0-7 days, 0-6 days, 0-5 days, 0-4 days, 0-3 days, 0-2 days, 0-1 days, 0-12 hours, 0-6 hours, 0-2 hours, 0-1 hour, 1-28 days, 1-27 days, 1-26 days, 1-25 days, 1-24 days, 1-23 days, 1-22 days, 1-21 days, 1-20 days, 1-19 days, 1-18 days, 1-17 days, 1-16 days, 1-15 days, 1-14 days, 1-13 days, 1-12 days, 1-11 days, 1-10 days, 1-9 days, 1-8 days, 1-7 days, 1-6 days, 1-5 days, 1-4 days, 1-3 days, 1-2 days, 2-28 days, 2-27 days, 2-26 days, 2-25 days, 2-24 days, 2- 23 days, 2-22 days, 2-21 days, 2-20 days, 2-19 days, 2-18 days, 2-17 days, 2-16 days, 2-15 days, 2-14 days, 2-13 days, 2-12 days, 2-11 days, 2-10 days, 2-9 days, 2-8 days, 2-7 days, 2-6 days, 2-5 days, 2-4 days, 2-3 days, 3-28 days, 3-27 days, 3-26 days, 3-25 days, 3-24 days, 3-23 days, 3-22 days, 3-21 days, 3-20 days, 3-19 days, 3-18 days, 3-17 days, 3-16 days, 3-15 days, 3-14 days, 3-13 days, 3-12 days, 3-11 days, 3-10 days, 3-9 days, 3-8 days, 3-7 days, 3-6 days, 3-5 days, 3-4 days, 4-28 days, 4-27 days, 4-26 days, 4-25 days, 4-24 days, 4-23 days, 4-22 days, 4-21 days, 4-20 days, 4-19 days, 4-18 days, 4-17 days, 4-16 days, 4-15 days, 4-14 days, 4-13 days, 4-12 days, 4-11 days, 4-10 days, 4-9 days, 4-8 days, 4-7 days, 4-6 days, 4-5 days, 5-28 days, 5-27 days, 5-26 days, 5-25 days, 5-24 days, 5-23 days, 5-22 days, 5-21 days, 5-20 days, 5-19 days, 5-18 days, 5-17 days, 5-16 days, 5-15 days, 5-14 days, 5-13 days, 5-12 days, 5-11 days, 5-10 days, 5-9 days, 5-8 days, 5-7 days, 5-6 days, 6-28 days, 6-27 days, 6-26 days, 6-25 days, 6-24 days, 6-23 days, 6-22 days, 6-21 days, 6-20 days, 6-19 days, 6-18 days, 6-17 days, 6-16 days, 6-15 days, 6-14 days, 6-13 days, 6-12 days, 6-11 days, 6-10 days, 6-9 days, 6-8 days, 6-7 days, 7-28 days, 7-27 days, 7-26 days, 7-25 days, 7- 24 days, 7-23 days, 7-22 days, 7-21 days, 7-20 days, 7-19 days, 7-18 days, 7-17 days, 7-16 days, 7-15 days, 7-14 days, 7-13 days, 7-12 days, 7-11 days, 7-10 days, 7-9 days, 7-8 days, 9-28 days, 9- 27 days, 9-26 days, 9-25 days, 9-24 days, 9-23 days, 9-22 days, 9-21 days, 9-20 days, 9-19 days, 9-18 days, 9-17 days, 9-16 days, 9-15 days, 9-14 days, 9-13 days, 9-12 days, 9-11 days, 9-10 days, 10-28 days, 10-27 days, 10-26 days, 10-25 days, 10-24 days, 10-23 days, 10-22 days, 10-21 days, 10-20 days, 10-19 days, 10-18 days, 10-17 days, 10-16 days, 10-15 days, 10-14 days, 10-13 days, 10-12 days, 10-11 days, 11-28 days, 11-27 days, 11-26 days, 11-25 days, 11-24 days, 11-23 days, 11-22 days, 11-21 days, 11-20 days, 11-19 days, 11-18 days, 11-17 days, 11-16 days, 11-15 days, 11-14 days, 11-13 days, 11-12 days, 12-28 days, 12-27 days, 12-26 days, 12-25 days, 12-24 days, 12-23 days, 12-22 days, 12-21 days, 12-20 days, 12-19 days, 12-18 days, 12-17 days, 12-16 days, 12-15 days, 12-14 days, 12-13 days, 13-28 days, 13-27 days, 13-26 days, 13-25 days, 13-24 days, 13-23 days, 13-22 days, 13-21 days, 13-20 days, 13-19 days, 13-18 days, 13-17 days, 13-16 days, 13-15 days, 13-14 days, 14-28 days, 14-27 days, 14-26 days, 14-25 days, 14-24 days, 14-23 days, 14-22 days, 14-21 days, 14-20 days, 14-19 days, 14-18 days, 14-17 days, 14-16 days, 14-15 days, 15-28 days, 15-27 days, 15-26 days, 15-25 days, 15-24 days, 15-23 days, 15-22 days, 15-21 days, 15-20 days, 15-19 days, 15-18 days, 15-17 days, 15-16 days, 16-28 days, 16-27 days, 16-26 days, 16-25 days, 16-24 days, 16-23 days, 16-22 days, 16-21 days, 16-20 days, 16-19 days, 16-18 days, 16-17 days, 17-28 days, 17-27 days, 17-26 days, 17-25 days, 17-24 days, 17-23 days, 17-22 days, 17-21 days, 17-20 days, 17-19 days, 17-18 days, 18-28 days, 18-27 days, 18-26 days, 18-25 days, 18-24 days, 18-23 days, 18-22 days, 18-21 days, 18-20 days, 18-19 days, 19-28 days, 19-27 days, 19-26 days, 19-25 days, 19-24 days, 19-23 days, 19-22 days, 19-21 days, 19-20 days, 20-28 days, 20-27 days, 20-26 days, 20-25 days, 20-24 days, 20-23 days, 20-22 days, 20-21 days, 21-28 days, 21-27 days, 21-26 days, 21-25 days, 21-24 days, 21-23 days, 21-22 days, 22-28 days, 22-27 days, 22-26 days, 22-25 days, 22-24 days, 22-23 days, 23-28 days, 23-27 days, 23-26 days, 23-25 days, 23-24 days, 24-28 days, 24-27 days, 24-26 days, 24-25 days, 25-28 days, 25-27 days, 25-26 days, 26-28 days, 26-27 days, or 27-28 days of age at the time of administration of the vaccine composition described herein. In some embodiments, the human neonate is 1, 2, 3, 4, 5, 6, 7, 8, 9, 10, 11, 12, 13, 14, 15, 16, 17, 18, 19, 20, 21, 22, 23, 24, 25, 26, 27, or 28 days of age at the time of administration of the vaccine composition described herein.

In some embodiments, the human infant is less than 28 days of age at the time of administration (vaccination). In some embodiments, the human infant is less than 4 days of age at the time of administration (vaccination). In some embodiments, the human infant is less than 2 days of age at the time of administration (vaccination). In some embodiments, the human infant is less than 24 hours of age at the time of administration (vaccination). In some embodiments, the administration (vaccination) occurs at birth. In some embodiments, a human neonate (less than 28 days of age) receives 1 or 2 doses of the vaccine described herein. In some embodiments, the human neonate receives one dose before 28-days of age (e.g., 2, 3, 4, 5, 6, 7, 8, 9, 10, 11, 12, 13, 14, 15, 16, 17, 18, 19, 20 days of age) and a second dose before or at 28-days of age. In some embodiments, the human subject receives one dose at 2 months, 4 months, or 6 months of age, and a second dose after the first dose at 2 months, 4 months, or 6 months of age. In some embodiments, a human subject receives a second dose before or equal to 6-months of age (e.g., 1, 2, 3, 4, 5, 6 months of age). In some embodiments, the administration occurs when the human infant is 2 months, 4 months, and 6 months of age. In some embodiments, a human subject receives a second dose after 6-months of age (e.g., 1 year, 2 years, 3 years of age).

In some embodiments, immunization of older human subjects that are more than 28-days old (e.g., 1 month, 2 months, 3 months, 4 months, 5 months, 6 months, 7 months, 8 months, 9 months, 10 months, 11 months, 12 months, 2 years, 3 years, 4 years, 5 years, 10 years, 11 years, 12 years, 13 years, 14 years, 15 years, 16 years, 17 years old) is contemplated. In some embodiments, the human subject is an adult (e.g., more than 18 years old). In some embodiments, the human subject is an elderly (e.g., more than 60 years old). In some embodiments, the human subject is more than 65-years of age. In some embodiments, the human subject receives one or two doses of the vaccine described herein after 65-years of age.

In some embodiments, the human subject is born prematurely or has low birth weight.

"Born prematurely" means the human subject is born before 40-weeks of term. In some embodiments, the human subject is born before 37-weeks of term. In some embodiments, the human subject is born before 32 weeks of term. In some embodiments, the human subject is born before 24 weeks of term. In some embodiments, the human subject is born before 40 weeks, 39 weeks, 38 weeks, 37 weeks, 36 weeks, 35 weeks, 34 weeks, 33 weeks, 32 weeks, 31 weeks, 30 weeks, 29 weeks, 28 weeks, 27 weeks, 26 weeks, 25 weeks, or 24 weeks of term. In some embodiments, the human subject is born with low birth weight (e.g., at least 20% lower than a normal birth weight).

In some embodiments, the human subject has an undeveloped (e.g., an infant or a neonate), weak (an elderly), or compromised immune system. Immunocompromised subjects include, without limitation, subjects with primary immunodeficiency or acquired immunodeficiency such as those suffering from sepsis, HIV infection, and cancers, including those undergoing chemotherapy and/or radiotherapy.

In some embodiments, the subject is a companion animal (a pet). The use of the vaccine compositions described herein in veterinary vaccine is also within the scope of the present disclosure. "A companion animal," as used herein, refers to pets and other domestic animals. Non-limiting examples of companion animals include dogs and cats; livestock such as horses, cattle, pigs, sheep, goats, and chickens; and other animals such as mice, rats, guinea pigs, and hamsters. In some embodiments, the subject is a research animal. Non-limiting examples of research animals include: rodents (e.g., ferrets, pigs, rats, mice, guinea pigs, and hamsters), rabbits, or non-human primates.

Once administered, the vaccine composition described herein elicits an immune response in the subject. In some embodiments, the immune response is an innate immune response. In some embodiments, the immune response is an adaptive immune response specific to the antigen in the composition or vaccine. In some embodiments, the vaccine composition described herein activates B cell immunity. In some embodiments, the vaccine composition elicits production of antibodies against the antigen. In some embodiments, the vaccine composition activates cytotoxic T cells specific to the antigen.

In some embodiments, the adjuvantation system described herein (e.g., STING ligand alone, or STING ligand formulated with alum), whether administered alone or in an admixture with an antigen, enhance the innate immune response, compared to without the adjuvantation system or when the antigen is administered alone. In some embodiments, the adjuvantation system described herein (e.g., STING ligand alone, or STING ligand formulated with alum) activates new born or elderly peripheral blood mononuclear cells (PBMCs). In some embodiments, the number of PBMCs that are activated is increased by at least 20% in the presence of the adjuvantation system described herein (e.g., STING ligand alone, or STING ligand formulated with alum), compared to without the adjuvantation system or when the antigen is administered alone. For example, the number of PBMCs that are activated may be increased by at least 20%, at least 30%, at least 40%, at least 50%, at least 60%, at least 70%, at least 80%, at least 90%, at least 100%, at least 2-fold, at least 5-fold, at least 10-fold, at least 100-fold, at least 1000-fold or more, in the presence of the adjuvantation system, compared to without the adjuvantation system or when the antigen is administered alone. In some embodiments, the number of PBMCs that are activated is increased by 20%, 30%, 40%, 50%, 60%, 70%, 80%, 90%, 100%, 2-fold, 5-fold, 10-fold, 100-fold, 1000-fold or more, in the presence of the adjuvantation system, compared to without the adjuvantation system or when the antigen is administered alone.

In some embodiments, the adjuvantation system described herein (e.g., STING ligand alone, or STING ligand formulated with alum) enhances the production of a proinflammatory cytokine (e.g., IFNγ+) in the subject. In some embodiments, the level of proinflammatory cytokines (e.g., IFNγ+) is increased by at least 20% in the presence of the adjuvantation system, compared to without the adjuvantation system or when the antigen is administered alone. For example, the level of proinflammatory cytokines (e.g., IFNγ+) may be increased by at least 20%, at least 30%, at least 40%, at least 50%, at least 60%, at least 70%, at least 80%, at least 90%, at least 100%, at least 2-fold, at least 5-fold, at least 10-fold, at least 100-fold, at least 1000-fold or more, in the presence of the adjuvantation system, compared to without the adjuvantation system or when the antigen is administered alone. In some embodiments, the level of proinflammatory cytokines (e.g., IFNγ+) is increased by 20%, 30%, 40%, 50%, 60%, 70%, 80%, 90%, 100%, 2-fold, 5-fold, 10-fold, 100-fold, 1000-fold or more, in the presence of the adjuvantation system, compared to without the adjuvantation system or when the antigen is administered alone.

In some embodiments, the adjuvantation system enhances innate immune memory (also referred to as trained immunity). "Innate immune memory" confers heterologous immunity that provides broad protection against a range of pathogens. In some embodiments, the innate immune memory is increased by at least 20% in the presence of the adjuvantation system, compared to without the adjuvantation system or when the antigen is administered alone. For example, the innate immune memory may be increased by at least 20%, at least 30%, at least 40%, at least 50%, at least 60%, at least 70%, at least 80%, at least 90%, at least 100%, at least 2-fold, at least 5-fold, at least 10-fold, at least 100-fold, at least 1000-fold or more, in the presence of the adjuvantation system, compared to without the adjuvantation system or when the antigen is administered alone. In some embodiments, the innate immune memory is increased by 20%, 30%, 40%, 50%, 60%, 70%, 80%, 90%, 100%, 2-fold, 5-fold, 10-fold, 100-fold, 1000-fold or more, in the presence of the adjuvantation system, compared to without the adjuvantation system or when the antigen is administered alone.

In some embodiments, the adjuvantation system, when administered as an admixture with an antigen (e.g., the vaccine composition described herein), enhances the anti-specific immune response against the antigen or against the invading agent where the antigen is derived from (e.g., a microbial pathogen or cancer), compared to without the adjuvantation system or when the antigen is administered alone. In some embodiments, the adjuvantation system enhances the production of antigen-specific antibody titer (e.g., by at least 20%) in the subject, compared to without the adjuvantation system or when the antigen is administered alone. For example, the adjuvantation system may enhance the production of antigen-specific antibody titer by at least 20%, at least 30%, at least 40%, at least 50%, at least 60%, at least 70%, at least 80%, at least 90%, at least 100%, at least 2-fold, at least 5-fold, at least 10-fold, at least 100-fold, at least 1000-fold or more. in the subject, compared to without the adjuvantation system or when the antigen is administered alone. In some embodiments, the adjuvantation system enhances the production of antigen-specific antibody titer by 20%, 30%, 40%, 50%, 60%, 70%, 80%, 90%, 100%, 2-fold, 5-fold, 10-fold, 100-fold, 1000-fold or more, in the presence of the adjuvantation system, compared to without the adjuvantation system or when the antigen is administered alone. One skilled in the art is familiar with how to evaluate the level of an antibody titer, e.g., by ELISA.

In some embodiments, the adjuvantation system polarizes the innate and adaptive immune response by shaping the pattern of cytokine and/or chemokine responses toward T helper 1 (Th1) immunity, important for host defense against intracellular pathogens. In some embodiments, the adjuvantation system polarizes the innate immune response toward T follicular helper (Tfh) cell immunity.

In some embodiments, the adjuvantation system prolongs the effect of a vaccine (e.g., by at least 20%) in the subject, compared to without the adjuvantation system or when the antigen is administered alone. For example, the adjuvantation system may prolong the effect of a vaccine by at least 20%, at least 30%, at least 40%, at least 50%, at least 60%, at least 70%, at least 80%, at least 90%, at least 100%, at least 2-fold, at least 5-fold, at least 10-fold, at least 100-fold, at least 1000-fold or more. in the subject, compared to without the adjuvantation system or when the antigen is administered alone. In some embodiments, the adjuvantation system prolongs the effect of a vaccine by 20%, 30%, 40%, 50%, 60%, 70%, 80%, 90%, 100%, 2-fold, 5-fold, 10-fold, 100-fold, 1000-fold or more, in the presence of the adjuvantation system, compared to without the adjuvantation system or when the antigen is administered alone.

In some embodiments, the adjuvantation system increases rate of (accelerates) an immune response, compared to without the adjuvantation system or when the antigen is administered alone. For example, the adjuvantation system may increase the rate of an immune response by at least 20%, at least 30%, at least 40%, at least 50%, at least 60%, at least 70%, at least 80%, at least 90%, at least 100%, at least 2-fold, at least 5-fold, at least 10-fold, at least 100-fold, at least 1000-fold or more. in the subject, compared to without the adjuvantation system or when the antigen is administered alone. In some embodiments, the adjuvantation system increases the rate of an immune response by 20%, 30%, 40%, 50%, 60%, 70%, 80%, 90%, 100%, 2-fold, 5-fold, 10-fold, 100-fold, 1000-fold or more, in the presence of the adjuvantation system, compared to without the adjuvantation system or when the antigen is administered alone. "Increase the rate of immune response" mean it takes less time for the immune system of a subject to react to an invading agent (e.g., a microbial pathogen).

In some embodiments, the antigen produces a same level of immune response against the antigen at a lower dose in the presence of the adjuvantation system, compared to without the adjuvantation system or when the antigen is administered alone. In some embodiments, the amount of antigen needed to produce the same level of immune response is reduced by at least 20% in the presence of the adjuvantation system, compared to without the adjuvantation system or when the antigen is administered alone. For example, the amount of antigen needed to produce the same level of immune response may be reduced by at least 20%, at least 30%, at least 40%, at least 50%, at least 60%, at least 70%, at least 80%, at least 90%, at least 95%, at least 99% or more, in the presence of the adjuvantation system, compared to without the adjuvantation system or when the antigen is administered alone. In some embodiments, the amount of antigen needed to produce the same level of immune response is reduced by at 20%, 30%, 40%, 50%, 60%, 70%, 80%, 90%, 95%, 99% or more, in the presence of the adjuvantation system, compared to without the adjuvantation system or when the antigen is administered alone.

The prophylactic or therapeutic use of the adjuvantation system, or the vaccine composition described herein is also within the scope of the present disclosure. In some embodiments, the composition or vaccine composition described herein are used in methods of vaccinating a subject by prophylactically administering to the subject an effective amount of the composition or vaccine composition described herein. "Vaccinating a subject" refer to a process of administering an immunogen, typically an antigen formulated into a vaccine, to the subject in an amount effective to increase or activate an immune response against the antigen and, thus, against a pathogen displaying the antigen. In some embodiments, the terms do not require the creation of complete immunity against the pathogen. In some embodiments, the terms encompass a clinically favorable enhancement of an immune response toward the antigen or pathogen. Methods for immunization, including formulation of a vaccine composition and selection of doses, routes of administration and the schedule of administration (e.g. primary dose and one or more booster doses), are well known in the art. In some embodiments, vaccinating a subject reduces the risk of developing a disease (e.g., an infectious disease or cancer) in a subject.

In some embodiments, the disease is an infectious disease. An "infectious disease" refers to an illness caused by a pathogenic biological agent that results from transmission from an infected person, animal, or reservoir to a susceptible host, either directly or indirectly, through an intermediate plant or animal host, vector, or inanimate environment. See Last J M. ed. A dictionary of epidemiology. 4th ed., New York: Oxford University Press, 1988. Infectious disease is also known as transmissible disease or communicable disease. In some embodiments, infectious diseases may be asymptomatic for much or even all of their course in a given host. Infectious pathogens include some viruses, bacteria, fungi, protozoa, multicellular parasites, and aberrant proteins known as prions. In some embodiments, the infectious disease is caused by any of the microbial pathogens (e.g., a bacterium, a *mycobacterium*, a fungus, a virus, a parasite or a prion) described herein or known to one skilled in the art. In some embodiments, the infectious disease is caused by *Plasmodium* spp. (malaria), *Bacillus anthracis* (anthrax), *Bordetella pertussis* (whooping cough), *Corynebacterium diphtheriae* (diphtheria), *Clostridium tetani* (tetanus), *Haemophilus influenzae* type b, pneumococcus (pneumococcal infections), Staphylococci spp., Group A or B streptococci, *Mycobacterium tuberculosis*, *Neiserria meningitidis* (meningococcal disease), *Salmonella typhi* (typhoid), *Vibrio cholerae* (Cholera), or *Yersinia pestis* (plague). In some embodiments, the infectious disease is caused by adenovirus, enterovirus such as poliomyelitis (polio), Ebola virus, herpes viruses such as herpes simplex virus, cytomegalovirus and varicella-zoster (chickenpox and shingles), measles, mumps, rubella, hepatitis-A, -B, or -C, human papilloma virus, Influenza virus, rabies, Japanese encephalitis, rotavirus, human immunodeficiency virus (HIV), respiratory syncytial virus (RSV), smallpox, yellow fever, or Zika Virus. In some embodiments, the infectious disease is caused by malaria, *Leishmania*, or a helminth. In some embodiments, the infectious disease is caused by *Candida* spp., *Aspergillus* spp., *Cryptococcus* spp., *Mucormycete, Blastomyces dermatitidis, Histoplasma capsulatum*, or *Sporothrix schenckii*. In some embodiments, the infectious disease is caused by prion.

In some embodiments, the composition or vaccine composition may be administered in combination with another therapeutic agent for the infectious diseases. Such other therapeutic agents may be, without limitation: antibiotics, anti-viral agents, anti-fungal agents, or anti-parasitic agents. One skilled in the art is familiar with how to select or administer the additional therapeutic agent based on the disease to be treated.

In some embodiments, the disease is allergy (e.g., allergic rhinitis) or asthma. It has been demonstrated that Th1/Th2 imbalance results in the clinical manifestation of allergy or asthma (e.g., as described in Ngoc et al., Curr Opin Allergy Clin Immunol. 2005 April; 5(2):161-6, incorporated herein by reference).

In some embodiments, the disease is cancer. Vaccine compositions described herein may be used in cancer immunotherapy by eliciting cancer-specific immune response against the cancer. The term "cancer" refers to a class of diseases characterized by the development of abnormal cells that proliferate uncontrollably and have the ability to infiltrate and destroy normal body tissues. See, e.g., *Stedman's Medical Dictionary*, 25th ed.; Hensyl ed.; Williams & Wilkins: Philadelphia, 1990. Exemplary cancers include, but are not limited to, hematological malignancies. Additional exemplary cancers include, but are not limited to, lung cancer (e.g., bronchogenic carcinoma, small cell lung cancer (SCLC), non-small cell lung cancer (NSCLC), adenocarcinoma of the lung); kidney cancer (e.g., nephroblastoma, a.k.a. Wilms' tumor, renal cell carcinoma); acoustic neuroma; adenocarcinoma; adrenal gland cancer; anal cancer; angiosarcoma (e.g., lymphangiosarcoma, lymphangioendotheliosarcoma, hemangiosarcoma); appendix cancer; benign monoclonal gammopathy; biliary cancer (e.g., cholangiocarcinoma); bladder cancer; breast cancer (e.g., adenocarcinoma of the breast, papillary carcinoma of the breast, mammary cancer, medullary carcinoma of the breast); brain cancer (e.g., meningioma, glioblastomas, glioma (e.g., astrocytoma, oligodendroglioma), medulloblastoma); bronchus cancer; carcinoid tumor; cervical cancer (e.g., cervical adenocarcinoma); choriocarcinoma; chordoma; craniopharyngioma; colorectal cancer (e.g., colon cancer, rectal cancer, colorectal adenocarcinoma); connective tissue cancer; epithelial carcinoma; ependymoma; endotheliosarcoma (e.g., Kaposi's sarcoma, multiple idiopathic hemorrhagic sarcoma); endometrial cancer (e.g., uterine cancer, uterine sarcoma); esophageal cancer (e.g., adenocarcinoma of the esophagus, Barrett's adenocarcinoma); Ewing's sarcoma; ocular cancer (e.g., intraocular melanoma, retinoblastoma); familiar hypereosinophilia; gall bladder cancer; gastric cancer (e.g., stomach adenocarcinoma); gastrointestinal stromal tumor (GIST); germ cell cancer; head and neck cancer (e.g., head and neck squamous cell carcinoma, oral cancer (e.g., oral squamous cell carcinoma), throat cancer (e.g., laryngeal cancer, pharyngeal cancer, nasopharyngeal cancer, oropharyngeal cancer)); heavy chain disease (e.g., alpha chain disease, gamma chain disease, mu chain disease; hemangioblastoma; hypopharynx cancer; inflammatory myofibroblastic tumors; immunocytic amyloidosis; liver cancer (e.g., hepatocellular cancer (HCC), malignant hepatoma); leiomyosarcoma (LMS); mastocytosis (e.g., systemic mastocytosis); muscle cancer; myelodysplastic syndrome (MDS); mesothelioma; myeloproliferative disorder (MPD) (e.g., polycythemia vera (PV), essential thrombocytosis (ET), agnogenic myeloid metaplasia (AMM) a.k.a. myelofibrosis (MF), chronic idiopathic myelofibrosis, chronic myelocytic leukemia (CML), chronic neutrophilic leukemia (CNL), hypereosinophilic syndrome (HES)); neuroblastoma; neurofibroma (e.g., neurofibromatosis (NF) type 1 or type 2, schwannomatosis); neuroendocrine cancer (e.g., gastroenteropancreatic neuroendoctrine tumor (GEP-NET), carcinoid tumor); osteosarcoma (e.g., bone cancer); ovarian cancer (e.g., cystadenocarcinoma, ovarian embryonal carcinoma, ovarian adenocarcinoma); papillary adenocarcinoma; pancreatic cancer (e.g., pancreatic andenocarcinoma, intraductal papillary mucinous neoplasm (IPMN), Islet cell tumors); penile cancer (e.g., Paget's disease of the penis and scrotum); pinealoma; primitive neuroectodermal tumor (PNT); plasma cell neoplasia; paraneoplastic syndromes; intraepithelial neoplasms; prostate cancer (e.g., prostate adenocarcinoma); rectal cancer; rhabdomyosarcoma; salivary gland cancer; skin cancer (e.g., squamous cell carcinoma (SCC), keratoacanthoma (KA), melanoma, basal cell carcinoma (BCC)); small bowel cancer (e.g., appendix cancer); soft tissue sarcoma (e.g., malignant fibrous histiocytoma (MFH), liposarcoma, malignant peripheral nerve sheath tumor (MPNST), chondrosarcoma, fibrosarcoma, myxosarcoma); sebaceous gland carcinoma; small intestine cancer; sweat gland carcinoma; synovioma; testicular cancer (e.g., seminoma, testicular embryonal carcinoma); thyroid cancer (e.g., papillary carcinoma of the thyroid, papillary thyroid carcinoma (PTC), medullary thyroid cancer); urethral cancer; vaginal cancer; and vulvar cancer (e.g., Paget's disease of the vulva). In some embodiments, the cancer treated using the composition and methods of the present disclosure is melanoma.

In some embodiments, additional anti-cancer agents may be administered in combination with the composition or vaccine composition described herein. In some embodiments, the anti-cancer agent is selected from the group consisting of: small molecules, oligonucleotides, polypeptides, and combinations thereof. In some embodiments, the anti-cancer agent is a chemotherapeutic agent. In some embodiments, the chemotherapeutic agent is selected from the group consisting of: Actinomycin, All-trans retinoic acid, Azacitidine, Azathioprine, Bleomycin, Bortezomib, Carboplatin, Capecitabine, Cisplatin, Chlorambucil, Cyclophosphamide, Cytarabine, Daunorubicin, Docetaxel, Doxifluridine, Doxorubicin, Epirubicin, Epothilone, Etoposide, Fluorouracil, Gemcitabine, Hydroxyurea, Idarubicin, Imatinib, Irinotecan, Mechlorethamine, Mercaptopurine, Methotrexate, Mitoxantrone, Oxaliplatin, Paclitaxel, Pemetrexed, Teniposide, Tioguanine, Topotecan, Valrubicin, Vinblastine, Vincristine, Vindesine, and Vinorelbine. In some embodiments, the chemotherapeutic agent is Doxorubicin.

In some embodiments, the anti-cancer agent is an immune checkpoint inhibitor. An "immune checkpoint" is a protein in the immune system that either enhances an immune response signal (co-stimulatory molecules) or reduces an immune response signal. Many cancers protect themselves from the immune system by exploiting the inhibitory immune checkpoint proteins to inhibit the T cell signal. Exemplary inhibitory checkpoint proteins include, without limitation, Cytotoxic T-Lymphocyte-Associated protein 4 (CTLA-4), Programmed Death 1 receptor (PD-1), T-cell Immunoglobulin domain and Mucin domain 3 (TIM3), Lymphocyte Activation Gene-3 (LAG3), V-set domain-containing T-cell activation inhibitor 1 (VTVN1 or B7-H4), Cluster of Differentiation 276 (CD276 or B7-H3), B and T Lymphocyte Attenuator (BTLA), Galectin-9 (GALS), Checkpoint kinase 1 (Chk1), Adenosine A2A receptor (A2aR), Indoleamine 2,3-dioxygenase (IDO), Killer-cell Immunoglobulin-like Receptor (KIR), Lymphocyte Activation Gene-3 (LAG3), and V-domain Ig suppressor of T cell activation (VISTA).

Some of these immune checkpoint proteins need their cognate binding partners, or ligands, for their immune inhibitory activity. For example, A2AR is the receptor of adenosine A2A and binding of A2A to A2AR activates a negative immune feedback loop. As another example, PD-1 associates with its two ligands, PD-L1 and PD-L2, to down regulate the immune system by preventing the activation of T-cells. PD-1 promotes the programmed cell death of antigen specific T-cells in lymph nodes and simultaneously reduces programmed cell death of suppressor T cells, thus achieving its immune inhibitory function. As yet another example, CTLA4 is present on the surface of T cells, and when bound to its binding partner CD80 or CD86 on the surface of antigen-present cells (APCs), it transmits an inhibitory signal to T cells, thereby reducing the immune response.

An "immune checkpoint inhibitor" is a molecule that prevents or weakens the activity of an immune checkpoint protein, For example, an immune checkpoint inhibitor may inhibit the binding of the immune checkpoint protein to its cognate binding partner, e.g., PD-1, CTLA-4, or A2aR. In some embodiments, the immune checkpoint inhibitor is a small molecule. In some embodiments, the immune checkpoint inhibitors is a nucleic acid aptamer (e.g., a siRNA targeting any one of the immune checkpoint proteins). In some embodiments, the immune checkpoint inhibitor is a recombinant protein. In some embodiments, the immune checkpoint inhibitor is an antibody. In some embodiments, the antibody comprises an anti-CTLA-4, anti-PD-1, anti-PD-L1, anti-TIM3, anti-LAG3, anti-B7-H3, anti-B7-H4, anti-BTLA, anti-GALS, anti-Chk, anti-A2aR, anti-IDO, anti-KIR, anti-LAG3, anti-VISTA antibody, or a combination of any two or more of the foregoing antibodies. In some embodiments, the immune checkpoint inhibitor is a monoclonal antibody. In some embodiments, the immune checkpoint inhibitor comprises anti-PD1, anti-PD-L1, anti-CTLA-4, or a combination of any two or more of the foregoing antibodies. For example, the anti-PD-1 antibody is pembrolizumab (Keytruda®) or nivolumab (Opdivo®) and the anti-CTLA-4 antibody is ipilimumab (Yervoy®). Thus, in some embodiments, the immune checkpoint inhibitor comprises pembrolizumab, nivolumab, ipilimumab, or any combination of two or more of the foregoing antibodies. The examples described herein are not meant to be limiting and that any immune checkpoint inhibitors known in the art and any combinations thereof may be used in accordance with the present disclosure.

Additional exemplary agents that may be used in combination with the compositions described herein include, but are not limited to, anti-proliferative agents, anti-cancer agents, anti-angiogenesis agents, anti-inflammatory agents, immunosuppressants, anti-bacterial agents, anti-viral agents, cardiovascular agents, cholesterol-lowering agents, anti-diabetic agents, anti-allergic agents, contraceptive agents, pain-relieving agents, and a combination thereof. In some embodiments, the additional agent is an anti-proliferative agent (e.g., anti-cancer agent). In some embodiments, the additional pharmaceutical agent is an anti-leukemia agent. In some embodiments, the additional pharmaceutical agent is ABITREXATE (methotrexate), ADE, Adriamycin RDF (doxorubicin hydrochloride), Ambochlorin (chlorambucil), ARRANON (nelarabine), ARZERRA (ofatumumab), BOSULIF (bosutinib), BUSULFEX (busulfan), CAMPATH (alemtuzumab), CERUBIDINE (daunorubicin hydrochloride), CLAFEN (cyclophosphamide), CLOFAREX (clofarabine), CLOLAR (clofarabine), CVP, CYTOSAR-U (cytarabine), CYTOXAN (cyclophosphamide), ERWINAZE (Asparaginase *Erwinia Chrysanthemi*), FLUDARA (fludarabine phosphate), FOLEX (methotrexate), FOLEX PFS (methotrexate), GAZYVA (obinutuzumab), GLEEVEC (imatinib mesylate), Hyper-CVAD, ICLUSIG (ponatinib hydrochloride), IMBRUVICA (ibrutinib), LEUKERAN (chlorambucil), LINFOLIZIN (chlorambucil), MARQIBO (vincristine sulfate liposome), METHOTREXATE LPF (methorexate), MEXATE (methotrexate), MEXATE-AQ (methotrexate), mitoxantrone hydrochloride, MUSTARGEN (mechlorethamine hydrochloride), MYLERAN (busulfan), NEOSAR (cyclophosphamide), ONCASPAR (Pegaspargase), PURINETHOL (mercaptopurine), PURIXAN (mercaptopurine), Rubidomycin (daunorubicin hydrochloride), SPRYCEL (dasatinib), SYNRIBO (omacetaxine mepesuccinate), TARABINE PFS (cytarabine), TASIGNA (nilotinib), TREANDA (bendamustine hydrochloride), TRISENOX (arsenic trioxide), VINCASAR PFS (vincristine sulfate), ZYDELIG (idelalisib), or a combination thereof. In some embodiments, the additional pharmaceutical agent is an anti-lymphoma agent. In some embodiments, the additional pharmaceutical agent is ABITREXATE (methotrexate), ABVD, ABVE, ABVE-PC, ADCETRIS (brentuximab vedotin), ADRIAMYCIN PFS (doxorubicin hydrochloride), ADRIAMYCIN RDF (doxorubicin hydrochloride), AMBOCHLORIN (chlorambucil), AMBOCLORIN (chlorambucil), ARRANON (nelarabine), BEACOPP, BECENUM (carmustine), BELEODAQ (belinostat), BEXXAR (tositumomab and iodine I 131 tositumomab), BICNU (carmustine), BLENOXANE (bleomycin), CARMUBRIS (carmustine), CHOP, CLAFEN (cyclophosphamide), COPP, COPP-ABV, CVP, CYTOXAN (cyclophosphamide), DEPOCYT (liposomal cytarabine), DTIC-DOME (dacarbazine), EPOCH, FOLEX (methotrexate), FOLEX PFS (methotrexate), FOLOTYN (pralatrexate), HYPER-CVAD, ICE, IMBRUVICA (ibrutinib), INTRON A (recombinant interferon alfa-2b), ISTODAX (romidepsin), LEUKERAN (chlorambucil), LINFOLIZIN (chlorambucil), Lomustine, MATULANE (procarbazine hydrochloride), METHOTREXATE LPF (methotrexate), MEXATE (methotrexate), MEXATE-AQ (methotrexate), MOPP, MOZOBIL (plerixafor), MUSTARGEN (mechlorethamine hydrochloride), NEOSAR (cyclophosphamide), OEPA, ONTAK (denileukin diftitox), OPPA, R-CHOP, REVLIMID (lenalidomide), RITUXAN (rituximab), STANFORD V, TREANDA (bendamustine hydrochloride), VAMP, VELBAN (vinblastine sulfate), VELCADE (bortezomib), VELSAR (vinblastine sulfate), VINCASAR PFS (vincristine sulfate), ZEVALIN (ibritumomab tiuxetan), ZOLINZA (vorinostat), ZYDELIG (idelalisib), or a combination thereof. In some embodiments, the additional pharmaceutical agent is REVLIMID (lenalidomide), DACOGEN (decitabine), VIDAZA (azacitidine), CYTOSAR-U (cytarabine), IDAMYCIN (idarubicin), CERUBIDINE (daunorubicin), LEUKERAN (chlorambucil), NEOSAR (cyclophosphamide), FLUDARA (fludarabine), LEUSTATIN (cladribine), or a combination thereof. In some embodiments, the additional pharmaceutical agent is ABITREXATE (methotrexate), ABRAXANE (paclitaxel albumin-stabilized nanoparticle formulation), AC, AC-T, ADE, ADRIAMYCIN PFS (doxorubicin hydrochloride), ADRUCIL (fluorouracil), AFINITOR (everolimus), AFINITOR DISPERZ (everolimus), ALDARA (imiquimod), ALIMTA (pemetrexed disodium), AREDIA (pamidronate disodium), ARIMIDEX (anastrozole), AROMASIN (exemestane), AVASTIN (bevacizumab), BECENUM (carmustine), BEP, BICNU (carmustine), BLENOXANE (bleomycin), CAF, CAMPTOSAR (irinotecan hydrochloride), CAPDX, CAPRELSA (vandetanib), CARBOPLATIN-TAXOL, CARMUBRIS (carmustine), CASODEX (bicalutamide), CEENU (lomustine), CERUBIDINE (daunorubicin hydrochloride), CERVARIX (recombinant HPV bivalent vaccine), CLAFEN (cyclophosphamide), CMF, COMETRIQ (cabozantinib-s-malate), COSMEGEN (dactinomycin), CYFOS (ifosfamide), CYRAMZA (ramucirumab), CYTOSAR-U (cytarabine), CYTOXAN (cyclophosphamide), DACOGEN (decitabine), DEGARELIX, DOXIL (doxorubicin hydrochloride liposome), DOXORUBICIN HYDROCHLORIDE, DOX-SL (doxorubicin hydrochloride liposome), DTIC-DOME (dacarbazine), EFUDEX (fluorouracil), ELLENCE (epirubicin hydrochloride), ELOXATIN (oxaliplatin), ERBITUX (cetuximab), ERIVEDGE (vismodegib), ETOPOPHOS (etoposide phosphate), EVACET (doxorubicin hydrochloride liposome), FARESTON (toremifene), FASLODEX (fulvestrant), FEC, FEMARA (letrozole), FLUOROPLEX (fluorouracil), FOLEX (methotrexate), FOLEX PFS (methotrexate), FOLFIRI, FOLFIRI-BEVACIZUMAB, FOLFIRI-CETUXIMAB, FOLFIRINOX, FOLFOX, FU-LV, GARDASIL (recombinant human papillomavirus (HPV) quadrivalent vaccine), GEMCITABINE-CISPLATIN, GEMCITABINE-OXALIPLATIN, GEMZAR (gemcitabine hydrochloride), GILOTRIF (afatinib dimaleate), GLEEVEC (imatinib mesylate), GLIADEL (carmustine implant), GLIADEL WAFER (carmustine implant), HERCEPTIN (trastuzumab), HYCAMTIN (topotecan hydrochloride), IFEX (ifosfamide), IFOSFAMIDUM (ifosfamide), INLYTA (axitinib), INTRON A (recombinant interferon alfa-2b), IRESSA (gefitinib), IXEMPRA (ixabepilone), JAKAFI (ruxolitinib phosphate), JEVTANA (cabazitaxel), KADCYLA (ado-trastuzumab emtansine), KEYTRUDA (pembrolizumab), KYPROLIS (carfilzomib), LIPODOX (doxorubicin hydrochloride liposome), LUPRON (leuprolide acetate), LUPRON DEPOT (leuprolide acetate), LUPRON DEPOT-3 MONTH (leuprolide acetate), LUPRON DEPOT-4 MONTH (leuprolide acetate), LUPRON DEPOT-PED (leuprolide acetate), MEGACE (megestrol acetate), MEKINIST (trametinib), METHAZO- LASTONE (temozolomide), METHOTREXATE LPF (methotrexate), MEXATE (methotrexate), MEXATE-AQ (methotrexate), MITOXANTRONE HYDROCHLORIDE, MITOZYTREX (mitomycin c), MOZOBIL (plerixafor), MUSTARGEN (mechlorethamine hydrochloride), MUTAMYCIN (mitomycin c), MYLOSAR (azacitidine), NAVELBINE (vinorelbine tartrate), NEOSAR (cyclophosphamide), NEXAVAR (sorafenib tosylate), NOLVADEX (tamoxifen citrate), NOVALDEX (tamoxifen citrate), OFF, PAD, PARAPLAT (carboplatin), PARAPLATIN (carboplatin), PEG-INTRON (peginterferon alfa-2b), PEMETREXED DISODIUM, PERJETA (pertuzumab), PLATINOL (cisplatin), PLATINOL-AQ (cisplatin), POMALYST (pomalidomide), prednisone, PROLEUKIN (aldesleukin), PROLIA (denosumab), PROVENGE (sipuleucel-t), REVLIMID (lenalidomide), RUBIDOMYCIN (daunorubicin hydrochloride), SPRYCEL (dasatinib), STIVARGA (regorafenib), SUTENT (sunitinib malate), SYLATRON (peginterferon alfa-2b), SYLVANT (siltuximab), SYNOVIR (thalidomide), TAC, TAFINLAR (dabrafenib), TARABINE PFS (cytarabine), TARCEVA (erlotinib hydrochloride), TASIGNA (nilotinib), TAXOL (paclitaxel), TAXOTERE (docetaxel), TEMODAR (temozolomide), THALOMID (thalidomide), TOPOSAR (etoposide), TORISEL (temsirolimus), TPF, TRISENOX (arsenic trioxide), TYKERB (lapatinib ditosylate), VECTIBIX (panitumumab), VEIP, VELBAN (vinblastine sulfate), VELCADE (bortezomib), VELSAR (vinblastine sulfate), VEPESID (etoposide), VIADUR (leuprolide acetate), VIDAZA (azacitidine), VINCASAR PFS (vincristine sulfate), VOTRIENT (pazopanib hydrochloride), WELLCOVORIN (leucovorin calcium), XALKORI (crizotinib), XELODA (capecitabine), XELOX, XGEVA (denosumab), XOFIGO (radium 223 dichloride), XTANDI (enzalutamide), YERVOY (ipilimumab), ZALTRAP (ziv-aflibercept), ZELBORAF (vemurafenib), ZOLADEX (goserelin acetate), ZOMETA (zoledronic acid), ZYKADIA (ceritinib), ZYTIGA (abiraterone acetate), ENMD-2076, PCI-32765, AC220, dovitinib lactate (TKI258, CHIR-258), BIBW 2992 (TOVOKTM), SGX523, PF-04217903, PF-02341066, PF-299804, BMS-777607, ABT-869, MP470, BIBF 1120 (VARGATEF®), AP24534, JNJ-26483327, MGCD265, DCC-2036, BMS-690154, CEP-11981, tivozanib (AV-951), OSI-930, MM-121, XL-184, XL-647, and/or XL228), proteasome inhibitors (e.g., bortezomib (Velcade)), mTOR inhibitors (e.g., rapamycin, temsirolimus (CCI-779), everolimus (RAD-001), ridaforolimus, AP23573 (Ariad), AZD8055 (AstraZeneca), BEZ235 (Novartis), BGT226 (Norvartis), XL765 (Sanofi Aventis), PF-4691502 (Pfizer), GDC0980 (Genetech), SF1126 (Semafoe) and OSI-027 (OSI)), oblimersen, gemcitabine, carminomycin, leucovorin, pemetrexed, cyclophosphamide, dacarbazine, procarbizine, prednisolone, dexamethasone, campathecin, plicamycin, asparaginase, aminopterin, methopterin, porfiromycin, melphalan, leurosidine, leurosine, chlorambucil, trabectedin, procarbazine, discodermolide, carminomycin, aminopterin, and hexamethyl melamine, or a combination thereof. In some embodiments, the additional pharmaceutical agent is a binder or inhibitor of an HMT (e.g., EZH1, EZH2, DOT1). In some embodiments, the additional agent is a protein kinase inhibitor (e.g., tyrosine protein kinase inhibitor). In some embodiments, the additional agent is selected from the group consisting of epigenetic or transcriptional modulators (e.g., DNA methyltransferase inhibitors, histone deacetylase inhibitors (HDAC inhibitors), lysine methyltransferase inhibitors), antimitotic drugs (e.g., taxanes and *vinca* alkaloids), hormone receptor modulators (e.g., estrogen receptor modulators and androgen receptor modulators), cell signaling pathway inhibitors (e.g., tyrosine protein kinase inhibitors), modulators of protein stability (e.g., proteasome inhibitors), Hsp90 inhibitors, glucocorticoids, all-trans retinoic acids, and other agents that promote differentiation.

In some embodiments, the vaccine composition described herein are formulated for administration to a subject. In some embodiments, the composition or vaccine composition further comprises a pharmaceutically acceptable carrier. The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio. The phrase "pharmaceutically acceptable carrier" means a pharmaceutically acceptable material, composition or vehicle, such as a liquid or solid filler, diluent, excipient, solvent or encapsulating material, involved in carrying or transporting the subject agents from one organ, or portion of the body, to another organ, or portion of the body. Each carrier must be "acceptable" in the sense of being compatible with the other ingredients of the formulation and not injurious to the tissue of the patient (e.g., physiologically compatible, sterile, physiologic pH, etc.). The term "carrier" denotes an organic or inorganic ingredient, natural or synthetic, with which the active ingredient is combined to facilitate the application. The components of the composition or vaccine composition described herein also are capable of being co-mingled with the molecules of the present disclosure, and with each other, in a manner such that there is no interaction which would substantially impair the desired pharmaceutical efficacy. Some examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, methylcellulose, ethyl cellulose, microcrystalline cellulose and cellulose acetate; (4) powdered tragacanth; (5) malt; (6) gelatin; (7) lubricating agents, such as magnesium stearate, sodium lauryl sulfate and talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol (PEG); (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) pH buffered solutions; (21) polyesters, polycarbonates and/or polyanhydrides; (22) bulking agents, such as polypeptides and amino acids (23) serum component, such as serum albumin, HDL and LDL; (22) C2-C12 alcohols, such as ethanol; and (23) other non-toxic compatible substances employed in pharmaceutical formulations. Wetting agents, coloring agents, release agents, coating agents, sweetening agents, flavoring agents, perfuming agents, preservative and antioxidants can also be present in the formulation.

The vaccine composition described herein may conveniently be presented in unit dosage form and may be prepared by any of the methods well-known in the art of pharmacy. The term "unit dose" when used in reference to a composition or vaccine composition described herein of the present disclosure refers to physically discrete units suitable as unitary dosage for the subject, each unit containing a predetermined quantity of active material calculated to produce the desired therapeutic effect in association with the required diluent; i.e., carrier, or vehicle.

The formulation of the composition or vaccine composition described herein may dependent upon the route of administration. Injectable preparations suitable for parenteral administration or intratumoral, peritumoral, intralesional or perilesional administration include, for example, sterile injectable aqueous or oleaginous suspensions and may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3 propanediol or 1,3 butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil may be employed including synthetic mono- or di-glycerides. In addition, fatty acids such as oleic acid find use in the preparation of injectables. The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

For topical administration, the composition or vaccine composition described herein can be formulated into ointments, salves, gels, or creams, as is generally known in the art. Topical administration can utilize transdermal delivery systems well known in the art. An example is a dermal patch.

Compositions suitable for oral administration may be presented as discrete units, such as capsules, tablets, lozenges, each containing a predetermined amount of the anti-inflammatory agent. Other compositions include suspensions in aqueous liquids or non-aqueous liquids such as a syrup, elixir or an emulsion.

Other delivery systems can include time-release, delayed release or sustained release delivery systems. Such systems can avoid repeated administrations of the anti-inflammatory agent, increasing convenience to the subject and the physician. Many types of release delivery systems are available and known to those of ordinary skill in the art. They include polymer base systems such as poly(lactide-glycolide), copolyoxalates, polycaprolactones, polyesteramides, polyorthoesters, polyhydroxybutyric acid, and polyanhydrides. Microcapsules of the foregoing polymers containing drugs are described in, for example, U.S. Pat. No. 5,075,109. Delivery systems also include non-polymer systems that are: lipids including sterols such as cholesterol, cholesterol esters and fatty acids or neutral fats such as mono- di- and tri-glycerides; hydrogel release systems; sylastic systems; peptide based systems; wax coatings; compressed tablets using conventional binders and excipients; partially fused implants; and the like. Specific examples include, but are not limited to: (a) erosional systems in which the anti-inflammatory agent is contained in a form within a matrix such as those described in U.S. Pat. Nos. 4,452,775, 4,667,014, 4,748,034 and 5,239,660 and (b) diffusional systems in which an active component permeates at a controlled rate from a polymer such as described in U.S. Pat. Nos. 3,832, 253, and 3,854,480. In addition, pump-based hardware delivery systems can be used, some of which are adapted for implantation.

Use of a long-term sustained release implant may be particularly suitable for treatment of chronic conditions. Long-term release, are used herein, means that the implant is constructed and arranged to delivery therapeutic levels of the active ingredient for at least 30 days, and preferably 60 days. Long-term sustained release implants are well-known to those of ordinary skill in the art and include some of the release systems described above.

In some embodiments, the vaccine composition described herein used for therapeutic administration must be sterile. Sterility is readily accomplished by filtration through sterile filtration membranes (e.g., 0.2 micron membranes). Alternatively, preservatives can be used to prevent the growth or action of microorganisms. Various preservatives are well known and include, for example, phenol and ascorbic acid. The cyclic Psap peptide and/or the composition or vaccine composition described herein ordinarily will be stored in lyophilized form or as an aqueous solution if it is highly stable to thermal and oxidative denaturation. The pH of the preparations typically will be about from 6 to 8, although higher or lower pH values can also be appropriate in certain instances. The chimeric constructs of the present disclosure can be used as vaccines by conjugating to soluble immunogenic carrier molecules. Suitable carrier molecules include protein, including keyhole limpet hemocyanin, which is a preferred carrier protein. The chimeric construct can be conjugated to the carrier molecule using standard methods. (Hancock et al., "Synthesis of Peptides for Use as Immunogens," in Methods in Molecular Biology: Immunochemical Protocols, Manson (ed.), pages 23-32 (Humana Press 1992)).

In some embodiments, the present disclosure contemplates a vaccine composition comprising a pharmaceutically acceptable injectable vehicle. The vaccines of the present disclosure may be administered in conventional vehicles with or without other standard carriers, in the form of injectable solutions or suspensions. The added carriers might be selected from agents that elevate total immune response in the course of the immunization procedure.

Liposomes have been suggested as suitable carriers. The insoluble salts of aluminum, that is aluminum phosphate or aluminum hydroxide, have been utilized as carriers in routine clinical applications in humans. Polynucleotides and polyelectrolytes and water soluble carriers such as muramyl dipeptides have been used.

Preparation of injectable vaccines of the present disclosure, includes mixing the vaccine composition with muramyl dipeptides or other carriers. The resultant mixture may be emulsified in a mannide monooleate/squalene or squalane vehicle. Four parts by volume of squalene and/or squalane are used per part by volume of mannide monooleate. Methods of formulating vaccine compositions are well-known to those of ordinary skill in the art. (Rola, Immunizing Agents and Diagnostic Skin Antigens. In: Remington's Pharmaceutical Sciences, 18th Edition, Gennaro (ed.), (Mack Publishing Company 1990) pages 1389-1404).

Additional pharmaceutical carriers may be employed to control the duration of action of a vaccine in a therapeutic application. Control release preparations can be prepared through the use of polymers to complex or adsorb chimeric construct. For example, biocompatible polymers include matrices of poly(ethylene-co-vinyl acetate) and matrices of a polyanhydride copolymer of a stearic acid dimer and sebacic acid. (Sherwood et al. (1992) Bio/Technology 10: 1446). The rate of release of the chimeric construct from such a matrix depends upon the molecular weight of the construct, the amount of the construct within the matrix, and the size of dispersed particles. (Saltzman et al. (1989) Biophys. J. 55: 163; Sherwood et al, supra.; Ansel et al.

Pharmaceutical Dosage Forms and Drug Delivery Systems, 5th Edition (Lea & Febiger 1990); and Gennaro (ed.), Remington's Pharmaceutical Sciences, 18th Edition (Mack Publishing Company 1990)). The chimeric construct can also be conjugated to polyethylene glycol (PEG) to improve stability and extend bioavailability times (e.g., Katre et al.; U.S. Pat. No. 4,766,106).

The terms "treatment," "treat," and "treating" refer to reversing, alleviating, delaying the onset of, or inhibiting the progress of a disease described herein. In some embodiments, treatment may be administered after one or more signs or symptoms of the disease have developed or have been observed. In other embodiments, treatment may be administered in the absence of signs or symptoms of the disease. For example, treatment may be administered to a susceptible subject prior to the onset of symptoms (e.g., in light of a history of symptoms and/or in light of exposure to a pathogen). Treatment may also be continued after symptoms have resolved, for example, to delay or prevent recurrence. Prophylactic treatment refers to the treatment of a subject who is not and was not with a disease but is at risk of developing the disease or who was with a disease, is not with the disease, but is at risk of regression of the disease. In some embodiments, the subject is at a higher risk of developing the disease or at a higher risk of regression of the disease than an average healthy member of a population.

An "effective amount" of a composition described herein refers to an amount sufficient to elicit the desired biological response. An effective amount of a composition described herein may vary depending on such factors as the desired biological endpoint, the pharmacokinetics of the compound, the condition being treated, the mode of administration, and the age and health of the subject. In some embodiments, an effective amount is a therapeutically effective amount. In some embodiments, an effective amount is a prophylactic treatment. In some embodiments, an effective amount is the amount of a compound described herein in a single dose. In some embodiments, an effective amount is the combined amounts of a compound described herein in multiple doses. When an effective amount of a composition is referred herein, it means the amount is prophylactically and/or therapeutically effective, depending on the subject and/or the disease to be treated. Determining the effective amount or dosage is within the abilities of one skilled in the art.

The terms "administer," "administering," or "administration" refers to implanting, absorbing, ingesting, injecting, inhaling, or otherwise introducing a compound described herein, or a composition thereof, in or on a subject. The composition of the vaccine composition described herein may be administered systemically (e.g., via intravenous injection) or locally (e.g., via local injection). In some embodiments, the composition of the vaccine composition described herein is administered orally, intravenously, topically, intranasally, or sublingually. Parenteral administrating is also contemplated. The term "parenteral" as used herein includes subcutaneous, intracutaneous, intravenous, intramuscular, intraarticular, intraarterial, intrasynovial, intrasternal, intrathecal, intralesional, and intracranial injection or infusion techniques. In some embodiments, the composition is administered prophylactically.

In some embodiments, the composition or vaccine composition is administered once or multiple times (e.g., 2, 3, 4, 5, or more times). For multiple administrations, the administrations may be done over a period of time (e.g., 6 months, a year, 2 years, 5 years, 10 years, or longer). In some embodiments, the composition or vaccine composition is administered twice (e.g., Day 0 and Day 7, Day 0 and Day 14, Day 0 and Day 21, Day 0 and Day 28, Day 0 and Day 60, Day 0 and Day 90, Day 0 and Day 120, Day 0 and Day 150, Day 0 and Day 180, Day 0 and 3 months later, Day 0 and 6 months later, Day 0 and 9 months later, Day 0 and 12 months later, Day 0 and 18 months later, Day 0 and 2 years later, Day 0 and 5 years later, or Day 0 and 10 years later).

EXAMPLES

Immunization is key to preventing infectious diseases, a leading cause of death early in life. However, due to age-specific immunity, vaccines often demonstrate reduced efficacy in newborns and young infants compared to adults. Here, in vitro and in vivo approaches were combined to identify adjuvant candidates for early life immunization. Newborn and adult bone marrow-derived dendritic cells (BMDCs) were employed to perform a screening of pattern recognition receptor agonists, and found that the Stimulator of Interferon Genes (STING) ligand 2'3'-cGAMP (hereafter cGAMP) induces a comparable expression of surface maturation markers in newborn and adult BMDCs. Then, the trivalent recombinant hemagglutinin (rHA) influenza vaccine, Flublok, was utilized as a model antigen to investigate the role of cGAMP in adult and early life immunization. cGAMP adjuvantation alone could increase rHA-specific antibody titers in adult but not newborn mice. Remarkably, as compared to alum or cGAMP alone, immunization with cGAMP formulated with alum (Alhydrogel) enhanced newborn rHA-specific IgG2a/c titers ~400 fold, an antibody subclass associated with the development of IFNγ-driven type 1 immunity in vivo and endowed with higher effector functions, by 42 days of life. Highlighting the amenability for successful vaccine formulation and delivery, next it was confirmed that cGAMP adsorbs onto alum in vitro. Accordingly, immunization early in life with (cGAMP+alum) promoted IFNγ production by $CD4^+$ T cells and increased the proportions and absolute numbers of $CD4^+CXCR5^+PD-1+T$ follicular helper and germinal center $GL-7^+$ or $CD138^+B$ cells, suggesting an enhancement of the germinal center reaction. Adjuvantation effects were apparently specific for IgG2a/c isotype switching without effect on antibody affinity maturation as there was no effect on rHA-specific IgG avidity. Overall this study suggests that cGAMP when formulated with alum may represent an effective adjuvantation system to foster humoral and cellular aspects of type 1 immunity for early life immunization.

1. Introduction

Infectious diseases represent a major cause of morbidity and mortality in neonates and young infants (Bhutta and Black, 2013, Liu et al., 2012). For example, each year in the US ~20,000 children <5 years old are hospitalized due to influenza complications and flu-related death may occur, especially among those with underlying chronic illness (Thompson et al., 2004). Immunization strategies are fundamental to prevent infectious diseases. However, due to age-specific immunity, vaccines often demonstrate reduced efficacy in newborns and young infants compared to adults (Kollmann et al., 2017, Levy et al., 2013). Newborn innate immune cells exhibit distinct activation profiles in response to pattern recognition receptor (PRR) agonists (Dowling and Levy, 2014, Zhang et al., 2017), and only certain PRR agonists (e.g. TLR7/8 agonists) (Dowling et al., 2017, Dowling et al., 2013, Dowling et al., 2017, Ganapathi et al., 2015, Levy et al., 2006, Levy et al., 2004, Philbin et al., 2012) or their combinations (Lemoine et al., 2015, van Haren et al., 2016) are able to induce an adult-like response. The newborn adaptive immune compartment presents distinct features that may also limit vaccine efficacy. Neonatal B cells can produce immunoregulatory cytokines (e.g. IL-10) (Pan et al., 2016, Sun et al., 2005, Zhang et al., 2007, Zhivaki et al., 2017), and the magnitude and persistence of the antibody response are reduced (Siegrist and Aspinall, 2009). Several mechanisms may contribute to distinct immunity in early life, including distinct activity of B and plasma cells (Pettengill and Levy, 2016, Pettengill et al., 2016), the presence of maternal antibodies, impaired CD4+ CXCR5+ PD-1+ T follicular helper (Tfh) cell differentiation and lymph node germinal center (GC) reaction (Debock et al., 2013, Mastelic et al., 2012) that may adequately support the antigen-specific B cell response. Moreover, neonatal CD4+ T cells produce lower amounts of IFNγ and are skewed toward Th2, Th17 and Treg polarization (Dowling and Levy, 2014, Zhang et al., 2017). Of note, adjuvants exhibit age-specific patterns of Th-polarization (van Haren et al., 2016) such that adjuvantation systems that boost adult immune responses do not necessarily lead to enhanced vaccine efficacy in newborns or young infants (Dowling and Levy, 2015). Therefore, identification of vaccine adjuvants capable of activating neonatal and infant immune responses may inform development of adjuvanted vaccine formulations that enhance early life immunization (Dowling et al., 2017).

Dendritic cells (DCs) play a pivotal role in activating T cells and instructing the adaptive immune response. They express a high diversity of PRRs, whose activation leads to DC migration to lymph nodes and enhancement of immune-stimulatory functions (Merad et al., 2013). Recently, a systems vaccinology analysis of young infants vaccinated with trivalent inactivated influenza vaccine with or without the oil-in-water adjuvant MF59 demonstrated that innate immune gene signatures (e.g. antiviral and DC genes) 1 day post-immunization correlated with vaccine efficacy, highlighting the importance of robust innate immune activation in early life immunization (Nakaya et al., 2016). Agonists of the intracellular receptors TLR7/8, that recognize viral single stranded RNAs, potently activate Th1-polarizing responses including expression of interferons, production of IL-12p'70, and up-regulation of co-stimulatory molecules in newborn DCs in vitro and enhance vaccine efficacy in newborn non-human primates in vivo (Dowling et al., 2017, Dowling et al., 2013, Dowling et al., 2017, Ganapathi et al., 2015, Levy et al., 2006, Levy et al., 2004, Philbin et al., 2012). Moreover, adjuvantation with the TLR9 agonist CpG increases CG Tfh and B cell responses in newborn mice (Mastelic et al., 2012). Among intracellular PRRs, the Stimulator of Interferon Genes (STING) is an amenable target for adjuvant discovery and development (Dubensky et al., 2013, Gutjahr et al., 2016). It binds cyclic dinucleotides (CDNs) derived from bacteria (i.e. c-di-AMP, c-di-GMP and 3'3'-cGAMP) or synthesized in mammalian cells by cGAMP synthase (cGAS) in response to double-stranded DNA in the cytoplasm (i.e. 2'3'-cGAMP). Upon activation, STING induces the TBK-1-mediated phosphorylation of IRF3, which in turn modulates the expression of type I interferons (IFNs), IFN-stimulated genes and also promotes DC maturation and type 1 (i.e. IFNγ-driven) immunity (Chen et al., 2016). Accordingly, STING agonists have demonstrated promising adjuvanticity in adult experimental models of parenteral and mucosal immunization as well as cancer immunotherapy (Baird et al., 2016, Blaauboer et al., 2014, Carroll et al., 2016, Corrales et al., 2015, Curran et al., 2016, Ebensen et al., 2011, Ebensen et al., 2007, Fu et al., 2015, Hanson et al., 2015, Karaolis et al., 2007, Li et al., 2013, Libanova et al., 2010, Madhun et al., 2011, Martin et al., 2017, Matos et al., 2017, Nakamura et al., 2015, Ogunniyi et al., 2008, Wang et al., 2016). However, to date, STING has not yet been investigated as an adjuvant target for early life immunization.

Here, an unbiased approach was used to identify PRR-based agonists for early life immunization. Adult and neonatal bone marrow-derived DCs (BMDCs) were employed to screen the activity of a comprehensive panel of PRR agonists and adjuvants, and found that the STING ligand 2'3'-cGAMP is a potent activator of newborn BMDCs. Strikingly, it was found that 2'3'-cGAMP formulated with alum induces antibody isotype switching toward IgG2a/c, a subclass endowed with higher effector functions, appears to enhance the GC reaction and also promotes Th1 polarization in immunized newborn mice. Altogether, this study supports the use of STING ligands and their formulations for enhancement of early life immunization.

2. Materials and Methods 2.1 Ethics Statements

All experiments involving animals were approved by the Animal Care and Use Committee of Boston Children's Hospital and Harvard Medical School (protocol numbers 15-11-3011 and 16-02-3130).

2.2 Animals

C57BL/6 and BALB/c mice were obtained from Taconic Biosciences or Charles River Laboratories and housed in specific pathogen-free conditions in the animal research facilities at Boston Children's Hospital. For breeding purposes, mice were housed in couples, and cages checked daily to assess pregnancy status of dams and/or the presence of pups. When a new litter was discovered, that day was recorded as day of life (DOL) 0. Both male and female pups were used for experiments.

2.3 Generation of Neonatal and Adult Murine Bone Marrow-Derived Dendritic Cells (BMDCs)

BMDCs were generated from newborn (5-7 days old) and adult (6-12 weeks old) C57BL/6 mice with an adaptation of previously described methods (Dowling et al., 2008, Lutz et al., 1999). Briefly, mice were sacrificed and legs removed; bones were surgically cleaned from surrounding tissue, extremities of tibiae and femurs were trimmed with sterile scissors and bone marrow flushed through a 70 µm nylon mesh strainer (Corning Life Sciences). Cell number and viability was determined by trypan blue exclusion. Whole bone marrow cells were plated into non-tissue culture-treated 100 mm Petri dishes (Corning Life Sciences) at a density of $0.3 \times 10^6$ cells/ml in 10 ml total volume/plate of complete culture medium (RPMI 1640 plus 10% heat inactivated fetal bovine serum [FBS, GE Healthcare HyClone], 50 µM 2-mercaptoethanol, 2 mM L-glutamine, 100 U/ml penicillin/streptomycin [Gibco ThermoFisher Scientific]) supplemented with 20 ng/ml of recombinant murine GM-CSF (rmGM-CSF, R&D systems). Plates were incubated in humidified atmosphere at 37° C., 5% $CO_2$ for 6 days, with one supplement of 10 ml of complete culture medium and rmGM-CSF on day 3. On Day 6, non-adherent and loosely adherent cells were harvested by washing the plate gently with culture medium. Adherent cells were discarded. For flow cytometry analysis, BMDCs were stained (20 minutes at 4° C.) in PBS+FBS 2%+EDTA 2 mM, fixed with formaldehyde 4% (10 minutes at RT) and acquired on a BD LSRFortessa flow cytometer (BD Biosciences) or a Sony spectral analyzer SP6800 (Sony Biotechnology) and data were analyzed using FlowJo v.10 software (Tree Star). For a complete list of antibodies and fluorochromes used in the study see Table 2.

2.4 PRRs Agonists, Adjuvants and BMDC In Vitro Stimulation

Rough (*Salmonella Minnesota*, R595) and smooth (*Escherichia coli*, O55:B5) lipopolysaccharide (LPS) were purchased from List Biological Laboratories. Aluminium hydroxide (Alhydrogel) and Aluminium phosphate (Adjuphos) were purchased from Brenntag Biosector. All remaining PRR agonists and adjuvants, as indicated in Table 3, were purchased from Invivogen. All PRR agonists employed in the studies were chosen based on and verified endotoxin free as indicated by the manufacturers. For stimulation experiments, immature BMDCs generated from newborn and adult mice were plated in round bottom 96-wells non-tissue culture-treated plates at the density of $10^5$ cells/well in 200 μl of fresh complete culture medium with rmGM-CSF as described above, with the appropriate stimuli at the concentrations indicated in Table 3. Cells were incubated at 37° C. for 20-24 hours, then supernatant harvested and TNF, IL-6, IL-1β and IL-12p70 concentrations were measured by ELISA (R&D Systems). IFNβ was measured with a bioluminescent ELISA kit (LumiKine, Invivogen). Alternatively, BMDCs were stained and analyzed by flow cytometry as indicated above. For experiments involving blocking antibodies, BMDCs were pre-incubated for 20 minutes at 37° C. with anti-mouse IFNAR1 (clone MAR1-5A3, 10 μg/ml, Biolegend) or anti-mouse TNF (clone MP6-XT22, 10 μg/ml, Biolegend) antibodies or an isotype control before stimulation.

2.5 Antigens, Immunization and Antibody Quantification

Both neonate and adult mice were immunized intramuscularly (i.m.) in the right posterior thigh with 50 μl of the 2016-2017 formulation of the FluBlok vaccine (Protein Sciences Corp.) containing 0.33 μg of each of the following recombinant influenza virus hemagglutinins (rHA): A/Michigan/45/2015 (H1N1), A/Hong Kong/4801/2014 (H3N2), and B/Brisbane/60/2008. Mice were immunized with a single dose at DOL 7 or a prime-boost schedule (two injections one week apart, for newborn mice at DOL 7 and 14). As indicated for specific experimental groups, the vaccine was formulated with Aluminium hydroxide (100 μg, hereafter "alum") with or without 2'3'-cGAMP (10 μg). Serum was collected at the indicated intervals for antibody detection. rHA-specific IgG, IgG1, IgG2c (for C57BL/6 mice) and IgG2a (for BALB/c mice) antibodies were quantified by ELISA. High binding flat bottom 96-well plates (Corning Life Sciences) were coated with 1 μg/l rHA in carbonate buffer pH 9.6, incubated overnight at 4° C. and blocked with PBS+BSA 1% (Sigma-Aldrich) for 1 h at room temperature (RT). Then, sera from vaccinated mice were added with an initial dilution of 1:100 and 1:4 serial dilutions in PBS+BSA 1% and incubated for 2 h at RT. Plates were then washed and incubated for 1 h at RT with HRP-conjugated anti-mouse IgG, IgG1, IgG2c or IgG2a (Southern Biotech). At the end of the incubation plates were washed again and developed with tetramethylbenzidine (BD Biosciences) for 5 minutes, then stopped with 2 N $H_2SO_4$. The optical density was read at 450 nm Versamax microplate reader with SoftMax Pro Version 5 (both from Molecular Devices) and endpoint titers were calculated using as cutoff three times the optical density of the background.

For assessing antibody avidity, plates were incubated 15 minutes with ammonium thiocyanate 0.5 M before the addition of HRP-conjugated anti-mouse IgG antibodies. Avidity was expressed as the Log $EC_{50}$ ratio of corresponding plates treated with or without ammonium thiocyanate.

2.6 Quantification of 2'3'-cGAMP Adsorption onto Alum

To quantify the extent of 2'3'-cGAMP adsorption to aluminum hydroxide (Alhydrogel), 100 μg/100 μl of 2'3'-cGAMP with 1000 μg/100 μl of alum (a 1:10 cGAMP:alum mass ratio) plus 300 μl of 0.9% saline were mixed. After vortexing for 10 seconds the sample was placed in a 37° C. incubator. Every 15 minutes the sample was vortexed for an additional 5 seconds and placed back into the incubator. Aliquots (0.75 ml) were taken at t=0.25, 0.5, 1, 2, 4 and 24 hours and centrifuged at 3000 RPM (rcf=664 g) to separate the alum from the supernatant. Supernatant was immediately removed and placed into an autosampler vial undiluted for analysis by reverse-phase high performance liquid chromatography (RP-HPLC) to determine adsorption as a function of time. RP-HPLC samples were run on a Waters 2695 HPLC equipped with a 2996 photodiode array detector at a wavelength of 254 nm. A gradient was performed using a two mobile phase system of 0.1% trifluoroacetic acid in water and 0.1% trifluoroacetic acid in acetonitrile, on an Agilent Zorbax Eclipse Plus C18, 4.6×150 mm, 5 micron column at 25° C. The response (peak area) of the samples were compared against a 50 μl 2'3'-cGAMP plus 200 μl 0.9% saline control and a separate 100 μl alum plus 400 μl saline control.

2.7 In Vitro Restimulation of rHA-Specific T Cell Responses

Splenocytes from immunized mice were harvested 10 days post-boost (DOL 24), as previously reported (Bagnoli et al., 2015, Lofano et al., 2015, Mastelic et al., 2012) and re-stimulated in vitro to assess cytokine production by flow cytometry. Spleens were mashed through a 70 μM strainer, washed with PBS and erythrocytes were lysed with 2 minute of incubation in ammonium chloride-based lysis buffer (BD Biosciences). Cells were then counted and plated $2 \times 10^6$ per well (round bottom 96-well plate) in 200 μl of complete culture medium with or without rHA 10 μg/ml or rHA 10 μg/ml+anti-mouse CD28 2 μg/ml (BioLegend). Plates were incubated for 18 hours at 37° C. with the addition of Brefeldin A (BD Biosciences) for the last 6 hours. Cells were stained against for surface antigens in (PBS+BSA 0.2%+$NaN_3$ 0.05%) for 20 minutes at 4° C., then fixed with formalin 2% (10 minutes at RT) and permeabilized with intracellular staining permeabilization wash buffer (BioLegend) for 20 minutes at 4° C. Finally, cells were stained with conjugated antibodies against IFNγ, IL-2, IL-4 and IL-17. Data were acquired on a BD LSRFortessa flow cytometer (BD Biosciences) and analyzed using FlowJo v.10 software (Tree Star). For a complete list of antibodies and fluorochromes used in the study see Table 2.

2.8 Analysis of the Germinal Center Reaction

Draining (inguinal) lymph nodes (dLNs) from immunized mice were harvested 10 days post-boost (DOL 24), as previously reported (Bagnoli et al., 2015, Lofano et al., 2015, Mastelic et al., 2012). To prepare a single-cell suspension, dLNs were pressed using the plunger end of a syringe. Then, cells were washed and stained with the following antibodies: for germinal center (GC) T follicular helper cells, anti-CD45, anti-B220, anti-CD3, anti-CD4, anti-programmed death-1 (CD279 or PD-1), anti-CXCR5; for GC B cells, anti-CD45, anti-B220, anti-CD3, anti-GL7 and anti-Syndecan-1 (CD138) (all from BioLegend). GC T follicular helper cells were defined as viable singlet $CD45^+$ $B220^-$ $CD3^+$ $CD4^+$ $CXCR5^+$ $PD-1^+$ cells. GC B cells were defined as viable singlet $CD45^+$ $B220^+$ $CD3^-$ $CD138^-$ $GL-7^+$. Cells were acquired on a BD LSRFortessa (BD Biosciences) and data were analyzed using FlowJo v.10 software (Tree Star). Absolute number of cell subsets were determined using CountBright Absolute Counting Beads (ThermoFisher Scientific). For a complete list of antibodies and fluorochromes used in the study see Table 2.

2.9 IFNγ ELISPOT

Draining lymph nodes (dLNs) from immunized mice were harvested 3 days post-boost (DOL 17). Nitrocellulose 96-microwell plates (Millipore) were coated with 75 µl/well of anti-mouse IFNγ (10 µg/ml in PBS, clone R4-6A2, BD Pharmingen) overnight at 4° C., washed twice with wash buffer (PBS+Tween-20 0.05%) and once with distilled water. Wells were blocked with 200 µl of complete culture medium for 2 h at RT. Single-cell suspensions of dLNs in complete culture medium supplemented with recombinant mouse IL-2 (5 ng/ml, PeproTech) were added to the wells in the presence or absence of 10 µg/ml of Flublok and 2 µg/ml anti-mouse CD28 (Biolegend) and cultured for 18 h. Wells were then washed and incubated with 100 ml of biotinylated anti-mouse IFNγ (5 µg/ml in PBS+FBS 10%, clone XMG1.2, BD Pharmingen) for 2 h at RT, washed again and incubated with 100 ul of streptavidin-alkaline phosphatise (1:1000 dilution in PBS+FBS 10%, MabTech) for 1 h prior to color development using BCIP/NBT substrate (Biorad) as per manufacturer's protocol. Spots on air-dried plates were counted on an ImmunoSpot Analyzer.

2.10 Statistical Analyses and Graphics

Data were analyzed and graphed using Prism for MacIntosh v. 7.0 (GraphPad Software). Tests used for statistical comparisons are indicated in figure legends. p value <0.05 was considered significant.

3. Results 3.1 Phenotypic and Functional Characterization of Neonatal BMDCs

Figures 8A, 8B, 8C:
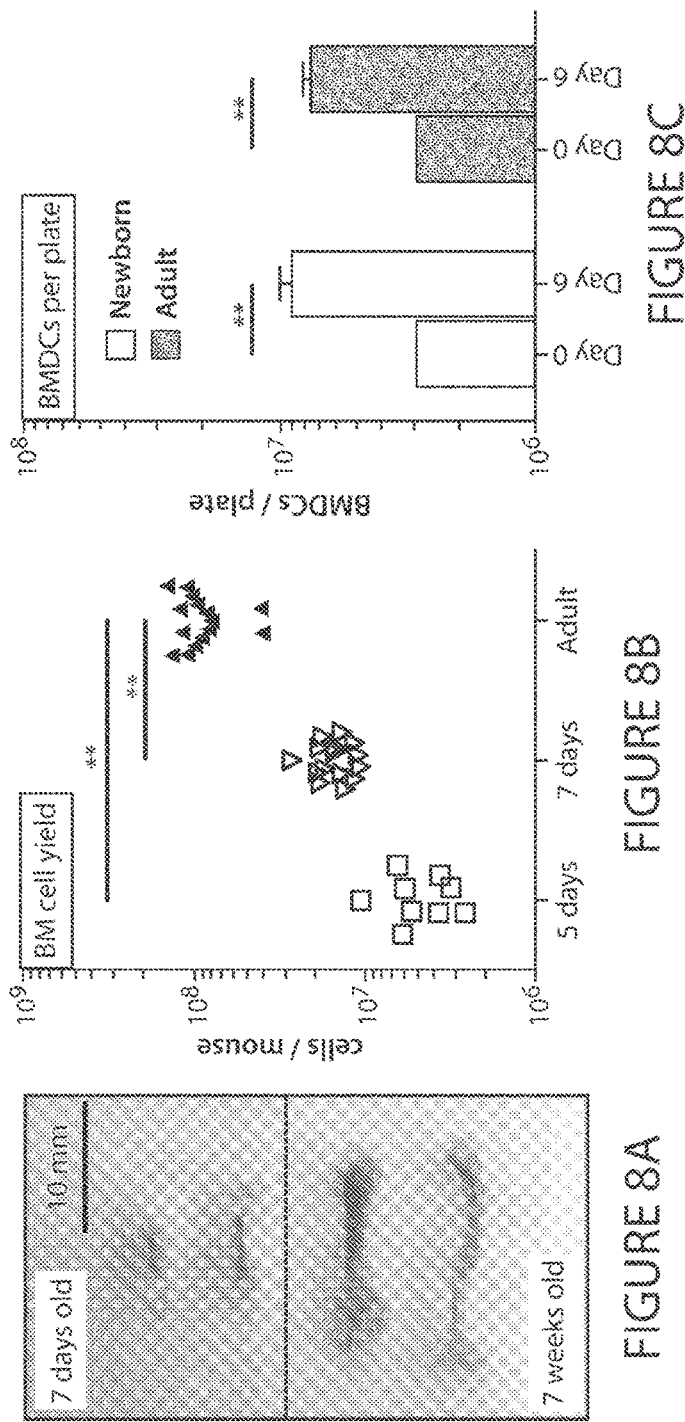
FIG. 8. Characterization of neonatal GM-CSF-differentiated bone marrow-derived dendritic cells. (A) Representative picture of tibia and femur from 7 day old (top) and 8 week old (bottom) mice. (B) Bone marrow cell yield at different ages from 4 bones per mouse. (C) In vitro expansion of BM precursors into BMDCs after 6 days of culture for newborn (white) and adult (gray) mice. (D) Representative gating strategy used to identify neonatal (top) and adult (bottom) BMDCs. (E) Median fluorescence intensity (MFI) of CD11c and MHCII expression by newborn (N, white) and adult (Ad, gray) BMDCs. Dotted line, unstained controls. Results are shown as scatter dot plot (B) or as mean+SEM (C, E) of 9-15 mice (B), 17-24 (C) or 6 (E) independent experiment. *p<0.01 determined by one-way ANOVA with Tukey's post hoc test (B) or unpaired t test (C, E).
Figure 9A:
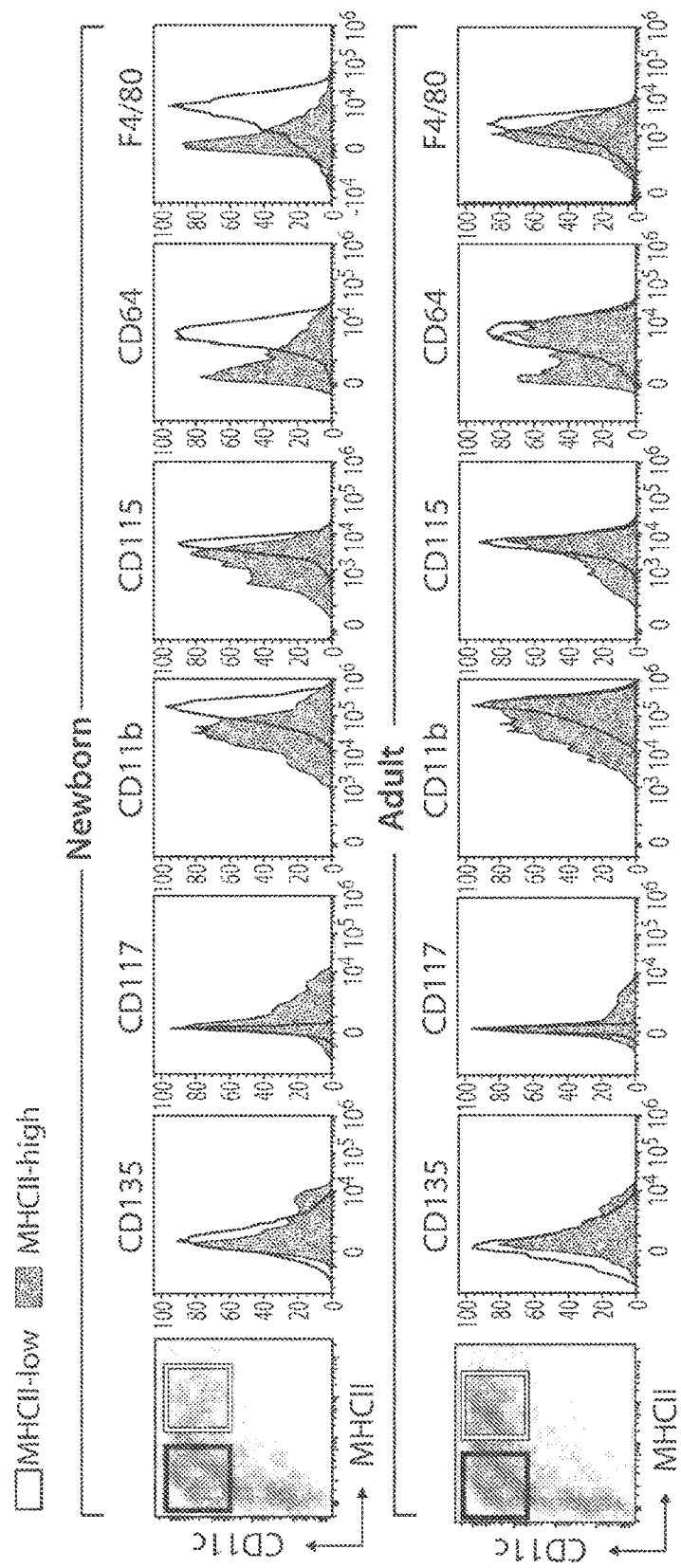
FIG. 9. Neonatal and adult BMDCs express distinct surface phenotypes. (A) Representative gating strategy and surface marker expression of MHCII-high (open histograms) and MHC-low (grey histograms) BMDCs generated from newborn (top) and adult (bottom) mice. (B) Percentage of MHCII-high and -low BMDCs generated from adult and newborn mice (left panel) and MFI of myeloid marker expression by neonatal and adult MHCII-high (gray bars) and -low (white bars) BMDCs. Results are expressed as mean+SEM of 4 independent experiments. * $p<0.05$, ** $p<0.01$ determined by two-way ANOVA with Sidak post hoc test.
Figure 9B:
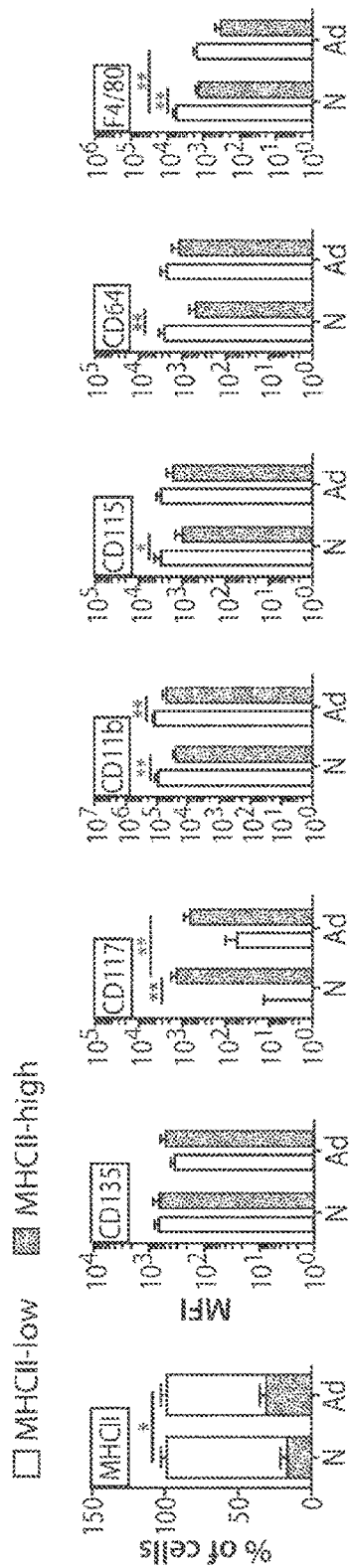

Murine BMDCs represent a widely used model to study DC function in vitro. Adult BMDCs represent a heterogeneous population composed of CD11c$^+$ macrophage-like and DC-like cells with distinct phenotypic and functional profiles (Helft et al., 2015). However, murine neonatal BMDCs have never been characterized in depth. Therefore, it was first sought to define the phenotypic and functional properties of neonatal BMDCs. Although the cell yield from neonatal bone marrow was lower compared to adult ones (FIG. 8A, B), neonatal immature BMDCs generated from 7 day-old mice grew in culture similarly to adult cells (FIG. 8C), and once fully differentiated they expressed similar levels of CD11c compared to adult cells but significantly lower levels of MHCII (FIG. 8D, E). To further characterize phenotypic differences between newborn and adult BMDCs, the expression of different macrophage and DC markers was assessed by flow cytometry. As previously reported for adult BMDCs (Helft et al., 2015), neonatal BMDCs were also comprised of CD11c$^+$ MHCII-low and CD11c$^+$ MHCII-high cells. Of note, the percentage of MHCII-low cells was higher in neonatal BMDCs compared to adult BMDCs. Neonatal MHCII-low BMDCs also expressed higher levels macrophage-associated markers (CD64, CD115, CD11b, F4/80) compared to MHCII-high BMDCs, while this population expressed higher levels of CD117. No significant differences in surface marker expression were found between corresponding neonatal and adult MHCII-high and -low populations, except for neonatal MHCII-low BMDCs that expressed higher levels of F4/80 and neonatal MHCII-high BMDCs that expressed higher levels of CD117 compared to their adult counterparts (FIG. 9 A, B).

Figures 10A, 10B:
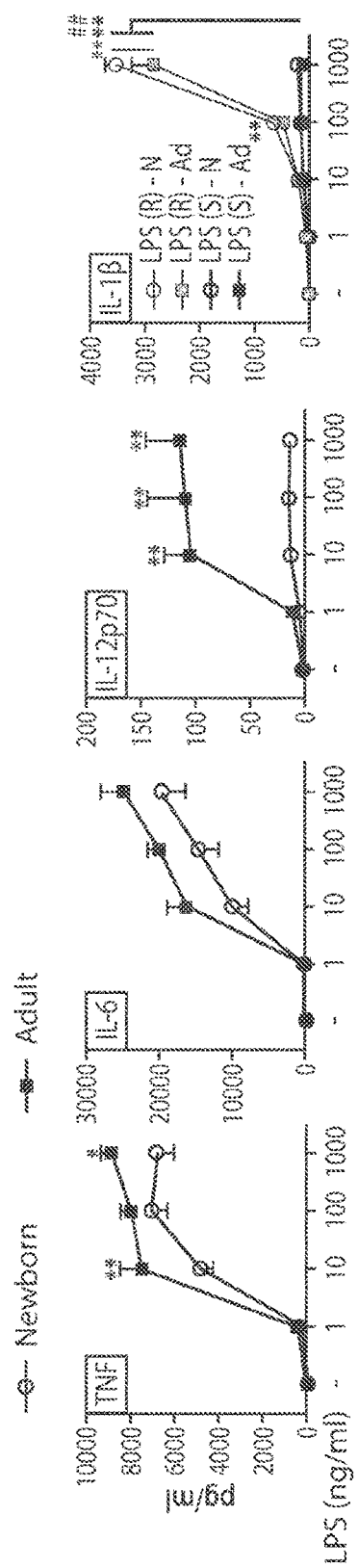
FIG. 10. Neonatal and adult BMDCs exhibit distinct cytokine and phenotypic profiles upon LPS stimulation. Neonatal and adult BMDCs were stimulated with smooth (A-D) or rough (B, red lines and symbols) LPS for 20-24 hours. Cytokine production (A, B) and MFI of surface marker expression (C, D) were respectively assessed by ELISA and flow cytometry. (C) Representative histograms of surface marker expression. Results are expressed as mean+SEM of 6 (A, B) or 4 (D) independent experiments. * $p<0.05$, ** $p<0.01$ determined by two-way ANOVA with Sidak post hoc test.
Figures 10C, 10D:
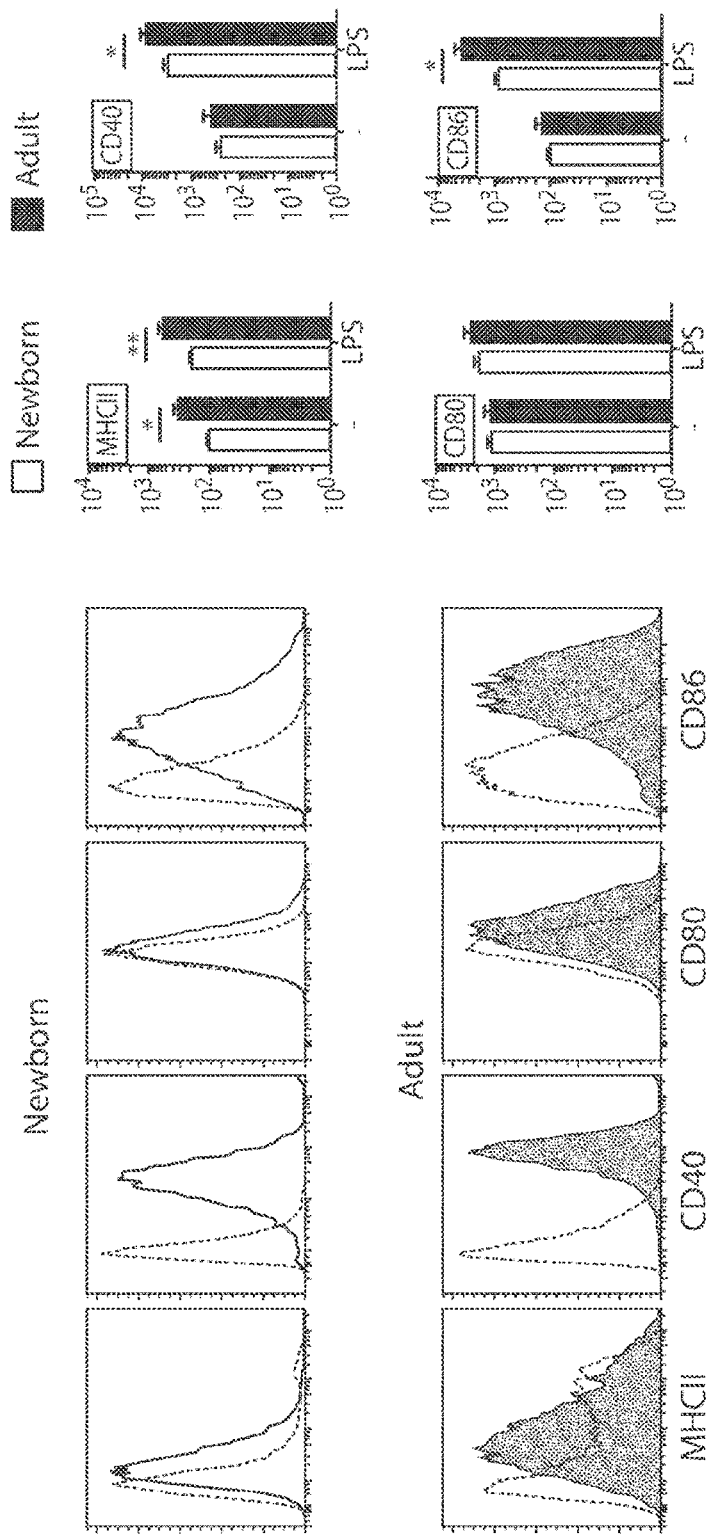

To characterize a functional response of newborn BMDCs, cytokine production and upregulation of co-stimulatory molecules in response to the TLR4 agonist smooth LPS were assessed. While newborn BMDC production of IL-6 and TNF was respectively comparable or slightly lower than adult BMDCs, IL-12p70 production, albeit detectable, was markedly reduced compared to adult BMDCs (FIG. 10A). The latter result might be consistent with a more macrophage-like phenotype of newborn BMDCs. As previously reported, both adult and newborn BMDCs produced IL-1β in response to rough but not smooth LPS (Zanoni et al., 2012), with newborn BMDCs producing slightly higher amounts of IL-1β (FIG. 10B). Finally, newborn BMDCs expressed lower levels of MHCII, CD40 and CD86 in response to smooth LPS (FIG. 10C, D).

3.2 Identification of STING as a Target for Inducing Neonatal BMDC Maturation

Figure 1C:
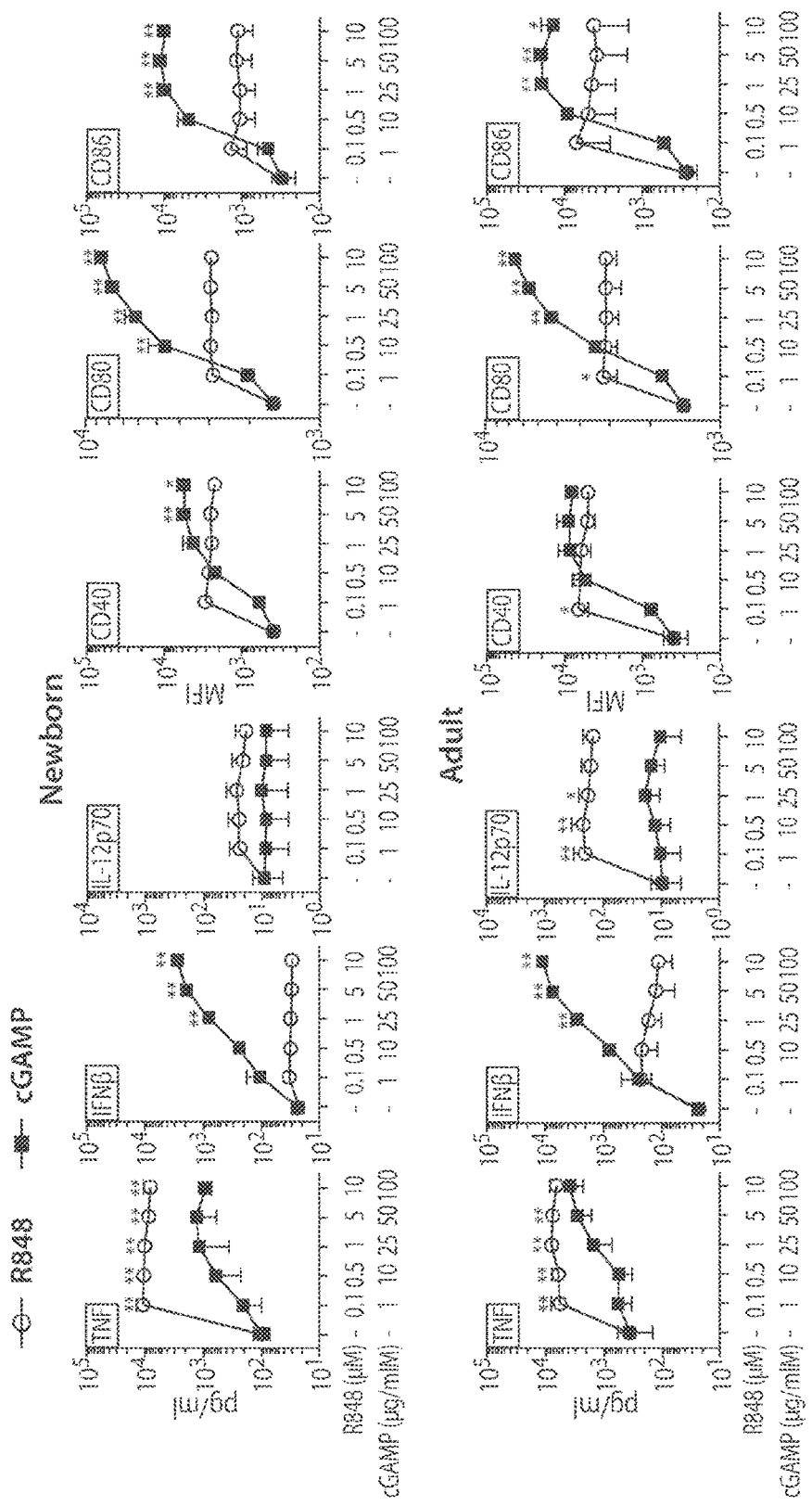
Figure 11:
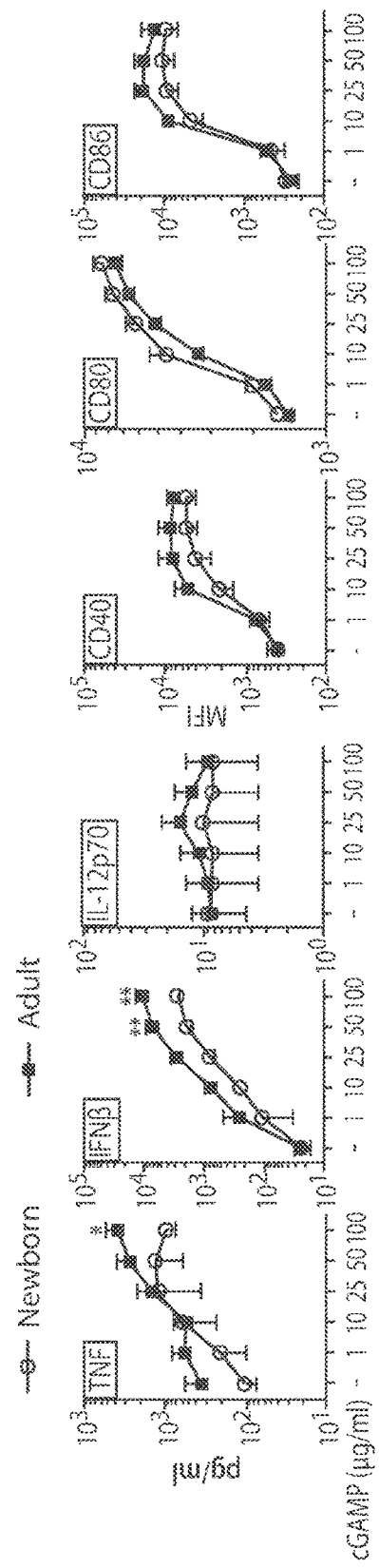
FIG. 11. Neonatal and adult BMDC cytokine production and surface maturation marker expression upon stimulation with cGAMP. Neonatal (open circles) and adult (black boxes) BMDCs were stimulated for 20-24 hours with increasing concentrations of cGAMP. Cytokine production and surface expression of maturation markers were respectively assessed by ELISA and flow cytometry. Results are expressed as mean+SEM of 4-5 (cytokine production) or 3 (surface marker expression) independent experiments. * $p<0.05$, ** $p<0.01$ determined by repeated measures two-way ANOVA with Sidak post hoc test.
Figure 12:
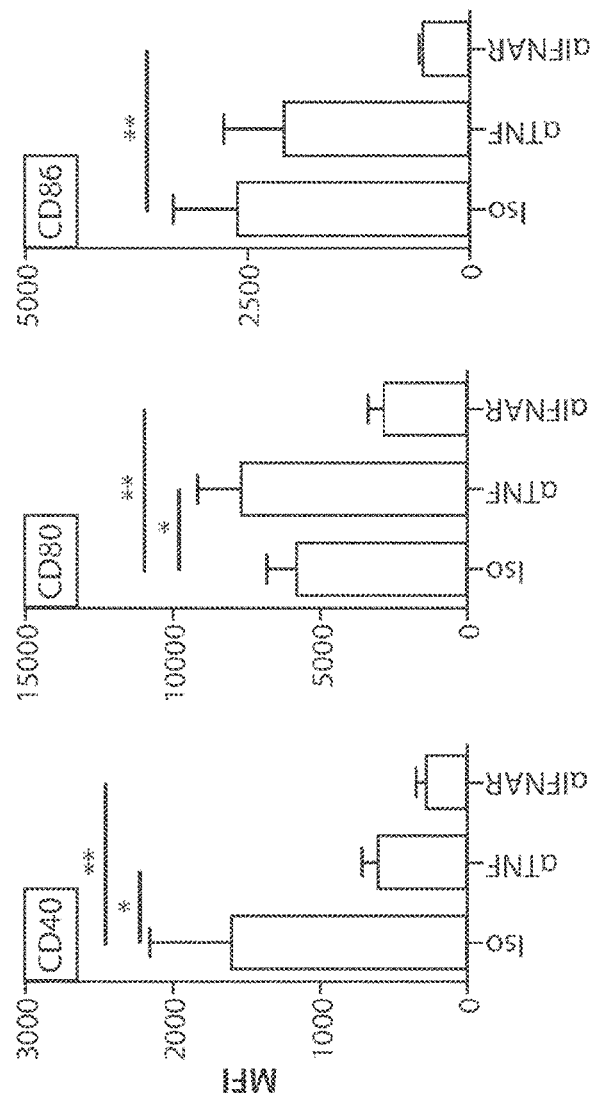
FIG. 12. cGAMP induces neonatal BMDC maturation in a type I interferon-dependent manner. Neonatal BMDCs were stimulated for 20-24 hours with cGAMP (25 µg/ml) in the presence of blocking anti-TNF and anti-IFNAR antibodies or an isotype control. Surface expression of maturation markers was assessed by flow cytometry. Results are expressed as mean+SEM of 3 independent experiments. * $p<0.05$, ** $p<0$. determined by repeated measures one-way ANOVA with Dunnett's post hoc test.

Having characterized phenotypic and functional features of neonatal and adult BMDCs, their response to a panel of PRR agonists and adjuvants (Table 3) were assessed. As readouts cytokine production (TNF, IL-1β, IL-6 and IL-12p70) and surface expression of maturation markers (CD40, CD80 and CD86) were measured. At the most effective, non-toxic (as established in preliminary experiments, data not shown) concentration of each agonist (in bold in Table 3), neonatal BMDCs produced similar amounts of TNF, IL-6 and IL-1β compared to adult BMDCs in response to different TLR7/8 agonists, namely R848 (Resiquimod, imidazoquinoline), CL075 (thiazoloquinolone) or CL264 (9-benzyl-8 hydroxyadenine), but again failed to produce IL-12p'70 (FIG. 1A). Remarkably, the upregulation of surface maturation marker expression on neonatal BMDCs was much lower than adult BMDCs upon any PRR stimulation, with the exception of the STING agonist 2'3'-cGAMP (hereafter cGAMP) (FIG. 1B). To assess in depth the response to STING and TLR7/8 agonists, neonatal and adult BMDCs were stimulated with different concentrations of cGAMP and R848. It was confirmed that R848 induced higher production of TNF and IL-12p70 (the latter only in adult BMDCs), while cGAMP was more effective than R848 at upregulating the expression of surface maturation markers (FIG. 1C). cGAMP also induced dose-dependent IFNβ production in both newborn and adult BMDCs (FIG. 1C). Of note, the response of neonatal and adult BMDCs to cGAMP was comparable (FIG. 11). Using neutralizing antibodies against TNF or type I IFN receptor (IFNAR), it was demonstrated that the expression of maturation markers by neonatal BMDCs mostly relies on type I IFN signaling (FIG. 12).

Figure 2A:
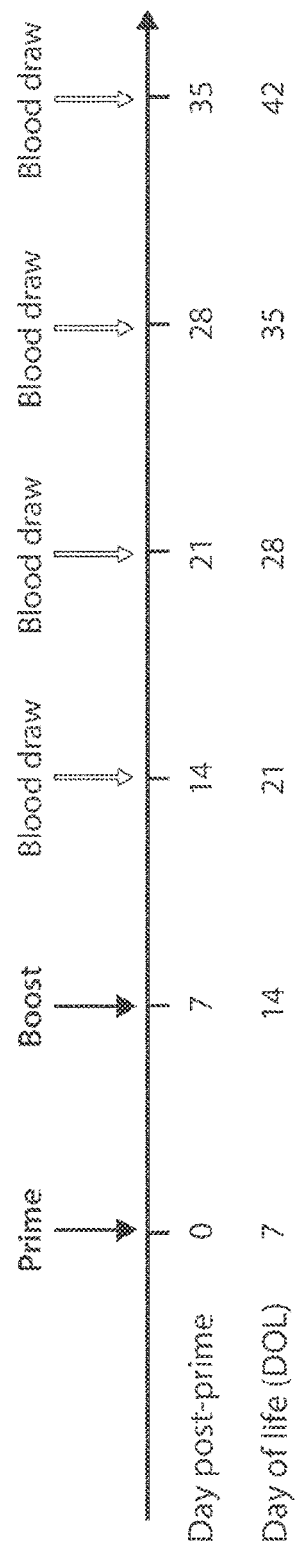
FIG. 2. Immunization with rHA formulated with cGAMP and alum induces distinct antibody profiles in adult and newborn mice. (A) Schematic representation of the immunization schedule for adult (day post-priming is indicated) and newborn (day of life, DOL, is indicated) mice. (B) Adult (top) and newborn (bottom) mice were immunized i.m. with saline, rHA, (rHA+alum), (rHA+cGAMP) or (rHA+cGAMP+alum) and antibody titers for rHA-specific IgG, IgG1 and IgG2c were determined by ELISA in serum samples collected at the reported timepoints. (C) Fold change of median Ab titers over (rHA+alum) group. White bars, newborn mice. Black bars, adult mice. Results are shown as median of 9-10 (adult) or 7-8 (newborn) mice per group. *, +, #p<0.05, **, ++, ##p<0.01 of groups indicated by the corresponding color respectively vs. saline, rHA and (rHA+alum) groups determined by Kruskall-Wallis with Dunn's post hoc test.
Figure 2B:
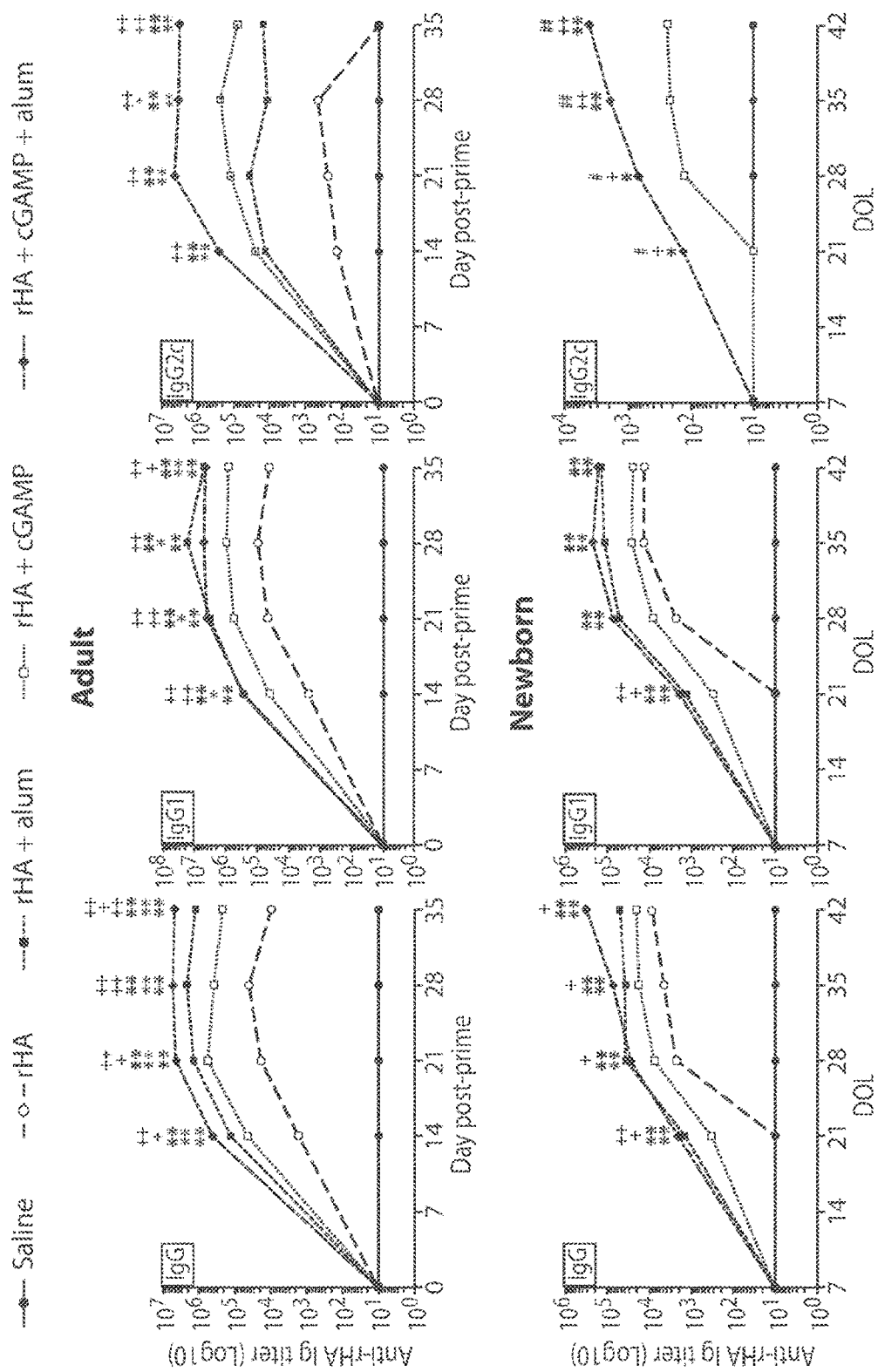
Figure 2C:
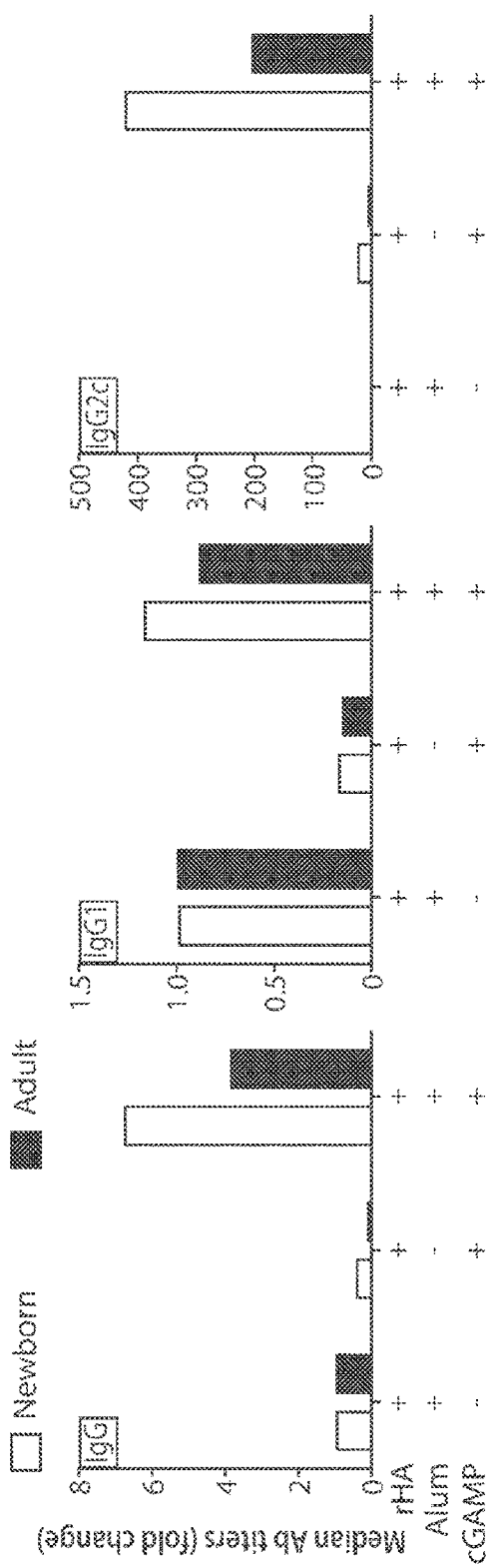
Figure 13:
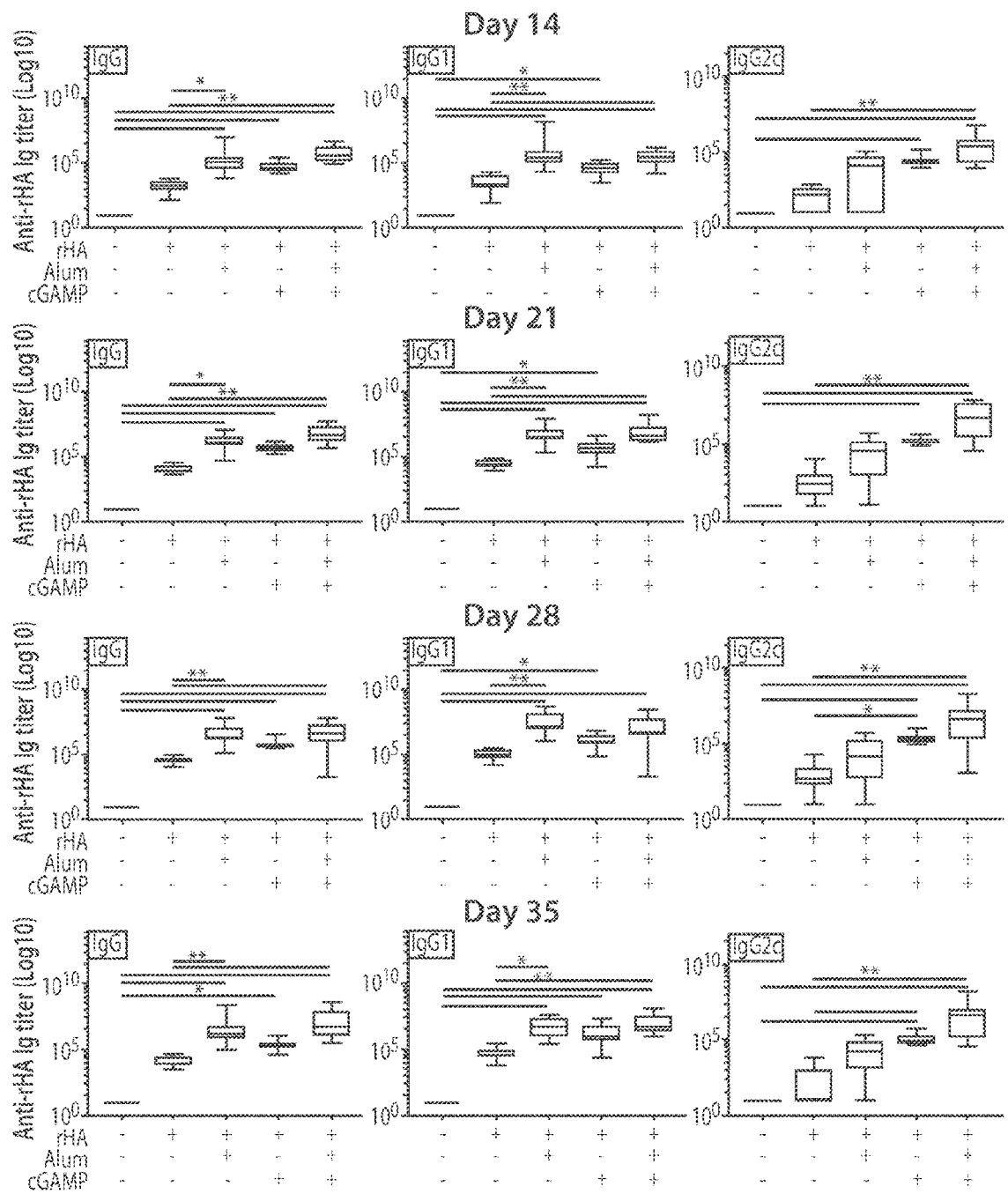
FIG. 13. Antibody titers in adult mice immunized with rHA formulated with cGAMP and alum. Adult mice were immunized and antibody titers were determined as indicated in FIG. 2. Results are shown as the median, the 25th and 75th percentiles (boxes) and the 5th and 95th percentiles (whiskers) of 9-10 mice per group. * $p<0.05$, ** $p<0.01$ determined by Kruskall-Wallis with Dunn's post hoc test.
Figure 14:
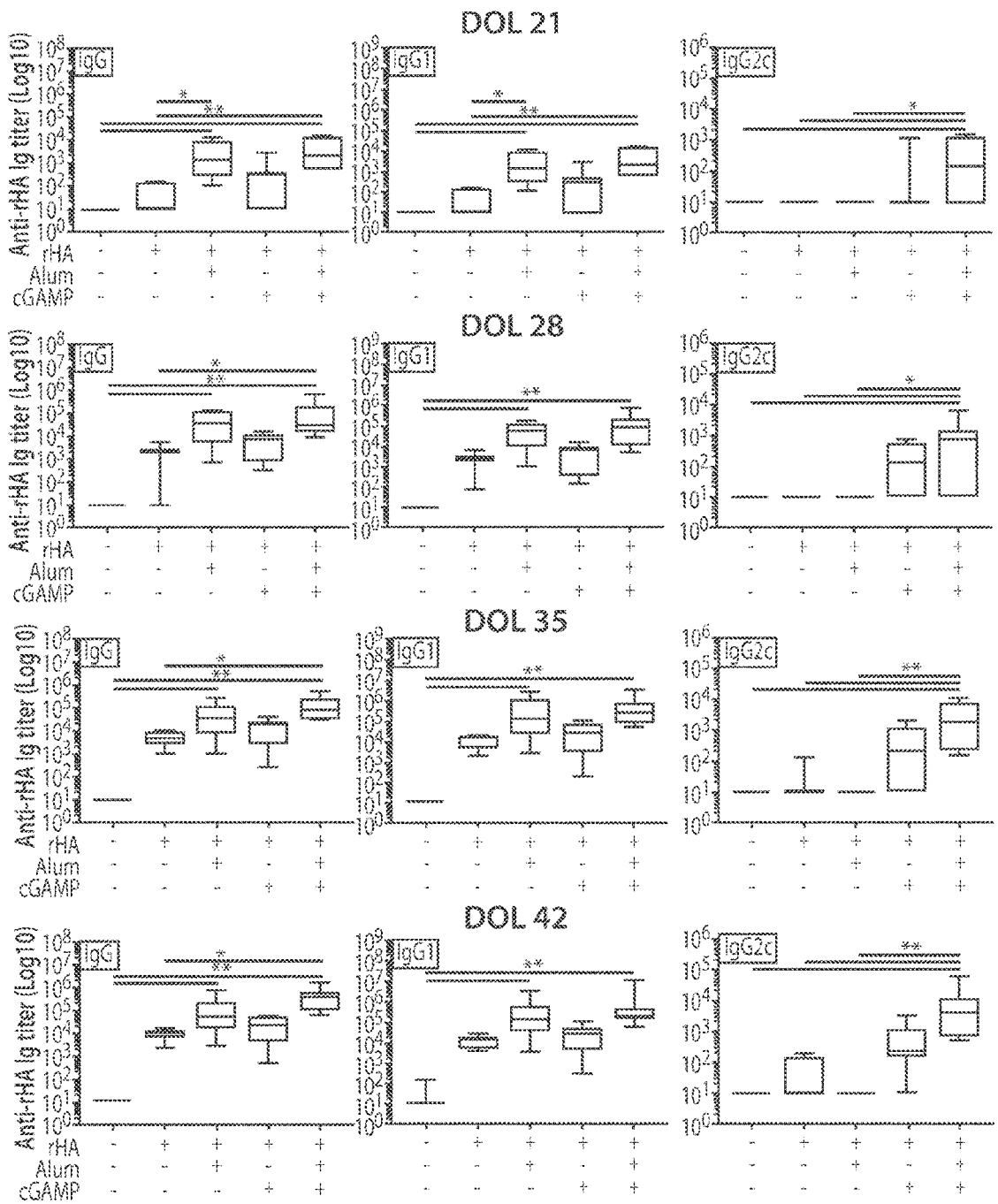
FIG. 14. Antibody titers in newborn mice immunized with rHA formulated with cGAMP and alum. Newborn mice were immunized and antibody titers were determined as indicated in FIG. 2. Results are shown as the median, the 25th and 75th percentiles (boxes) and the 5th and 95th percentiles (whiskers) of 7-8 mice per group. * $p<0.05$, ** $p<0.01$ determined by Kruskall-Wallis with Dunn's post hoc test.
Figure 15:
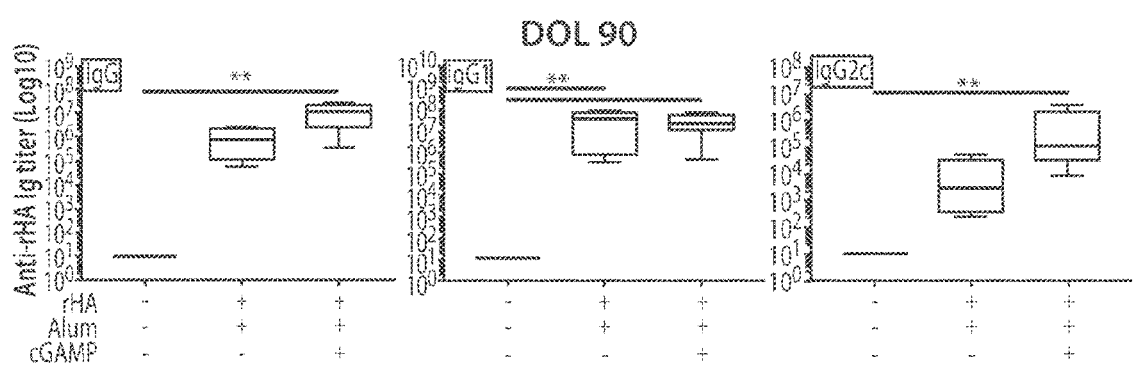
FIG. 15. Immunization with cGAMP+alum induces long-term persistence of rHA-specific IgG2c. Newborn mice were immunized and antibody titers were determined at DOL 90 as indicated in FIG. 2. Results are shown as the median, the 25th and 75th percentiles (boxes) and the 5th and 95th percentiles (whiskers) of 5 mice per group. ** $p<0.01$ determined by Kruskall-Wallis with Dunn's post hoc test.
Figure 16:
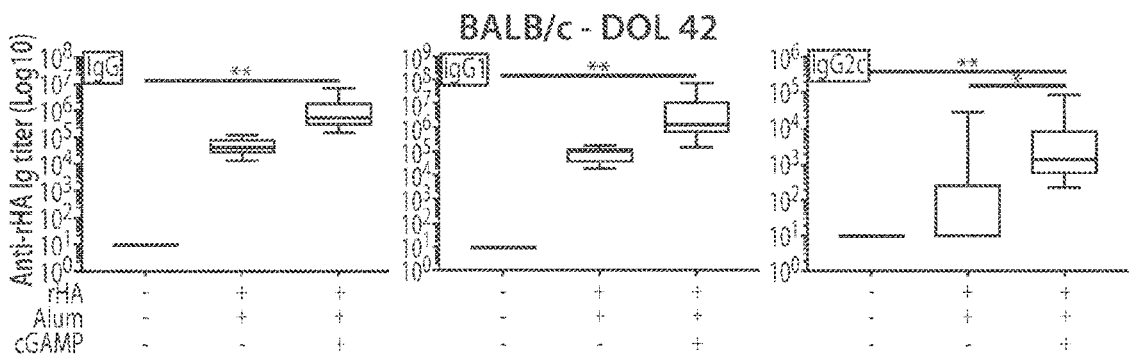
FIG. 16. Immunization of newborn BALB/c mice with rHA formulated with cGAMP and alum enhances rHA-specific antibody titers. Newborn BALB/c mice were immunized and antibody titers were determined at DOL 42 as indicated in FIG. 2. Results are shown as the median, the 25th and 75th percentiles (boxes) and the 5th and 95th percentiles (whiskers) of 7-8 mice per group. ** $p<0.01$ determined by Kruskall-Wallis with Dunn's post hoc test.

3.3 cGAMP Formulated with Alum Enhances Anti-rHA IgG2a/c Antibody Titers in an Early Life Immunization Model The in vitro results obtained so far supported further investigation of cGAMP as adjuvant candidate for early life immunization. Therefore, this hypothesis was tested in vivo. Newborn (7 day old) and adult (8-10 week old) C57BL/6 mice were immunized using a prime-boost schedule (FIG. 2A) and employing trivalent recombinant hemagglutinin (rHA) influenza vaccine Flublok as clinically relevant model antigen that is devoid of adjuvant, alone or formulated with alum (Alhydrogel, Al(OH)3), cGAMP or (cGAMP+alum) (FIG. 2B). Mice were bled 14, 21, 28 and 35 days post-prime (respectively day of life [DOL] 21, 28, 35, and 42 for newborn mice) to assess the magnitude and kinetic of the antibody response. As expected, both alum and cGAMP increased anti-rHA IgG titers in adult mice. The titers of the IgG subclasses IgG1 and IgG2c, respectively associated with type 2 and type 1 (IFNγ-driven) immunity (Bournazos and Ravetch, 2017, Gunn and Alter, 2016) were also investigated. In keeping with previously published data, alum preferentially increased anti-rHA IgG1 titers (median anti-rHA IgG1 titers at Day 35 post-prime: $5.02 \times 10^6$ for alum, $0.77 \times 10^6$ for cGAMP), while cGAMP was more effective than alum at enhancing anti-rHA IgG2c titers (median anti-rHA IgG2c titers at Day 35 post-prime: $0.16 \times 10^6$ for alum, $0.82 \times 10^6$ for cGAMP). (cGAMP+alum) was as effective as alum at increasing anti-rHA IgG and IgG1 titers (median anti-rHA IgG and IgG1 titers at Day 35 post-prime: respectively $4.77 \times 10^6$ and $4.46 \times 10^6$ for [cGAMP+alum]), and even more effective than cGAMP alone at enhancing anti-rHA IgG2c titers (median anti-rHA IgG2c titers at Day 35 post-prime: $3.27 \times 10^6$ for [cGAMP+alum]) (FIG. 2B, upper panels and FIG. 13). In newborn mice it was unexpectedly found that cGAMP was much less effective at increasing anti-rHA IgG, IgG1 and IgG2c titers (median anti-rHA IgG, IgG1 and IgG2c titers at Day 35 post-prime [DOL42]: respectively $20.57 \times 10^3$, $24.51 \times 10^3$ and $0.23 \times 10^3$ for cGAMP). Alum enhanced anti-rHA IgG and IgG1 titers, but in marked contrast from adult mice it did not induce anti-rHA IgG2c titers (median anti-rHA IgG, IgG1 and IgG2c titers at day 35 post-prime [DOL 42]: respectively $48.35 \times 10^3$, $143.23 \times 10^3$ and $0.00 \times 10^3$ for alum). Surprisingly, (cGAMP+alum) adjuvantation matched or exceeded alum at increasing anti-rHA IgG and IgG1 titers (median anti-rHA IgG and IgG1 titers at Day 35 post-prime [DOL 42]: respectively $329.19 \times 10^3$ and $167.83 \times 10^3$ for [cGAMP+alum]), and, remarkably, also induced relatively high titers of anti-rHA IgG2c as early as 14 days post-prime (DOL 21) (median anti-rHA IgG2c titers at Day 14 [DOL 21] and 35 post-prime [DOL 42]: respectively $0.14 \times 10^3$ and $4.23 \times 10^3$ for [cGAMP+alum]) (FIG. 2B, lower panels and FIG. 14). Therefore, the addition of cGAMP to alum markedly enhanced anti-rHA antibody production (in particular IgG2c), with a more prominent effect in newborn than adult mice (~400 as compared to ~150 fold increase, respectively) (FIG. 2C). Interestingly, newborn mice immunized at DOL 7 and 14 (as indicated in FIG. 2B) with (cGAMP+alum) still display the highest anti-rHA IgG and IgG2c titers at DOL 90 compared to saline and alum groups (FIG. 15). Enhancement of anti-rHA IgG and IgG2a titers induced by (cGAMP+alum) was also demonstrable in the Th2-skewed mouse strain BALB/c (FIG. 16).

In light of the robust adjuvanticity of the (cGAMP+alum) formulation, cGAMP adsorption to alum was quantified by RP-HPLC (Table 1). A rapid initial adsorption of cGAMP onto alum was observed (63% of total cGAMP) within 15 minutes from the incubation. The adsorption rate dropped quickly, with the overall adsorption reaching a plateau (75.33% of total cGAMP) after 24 hours of incubation. No significant degradation products were observed over this time window.

Altogether, the in vivo results demonstrate that (cGAMP+alum) is an effective formulation to enhance antigen-specific antibody titers (especially of the IgG2a/c subclass) for early life immunization.

3.4 (cGAMP+Alum) Fosters Th1 Polarization and Germinal Center Reaction

Figure 3A:
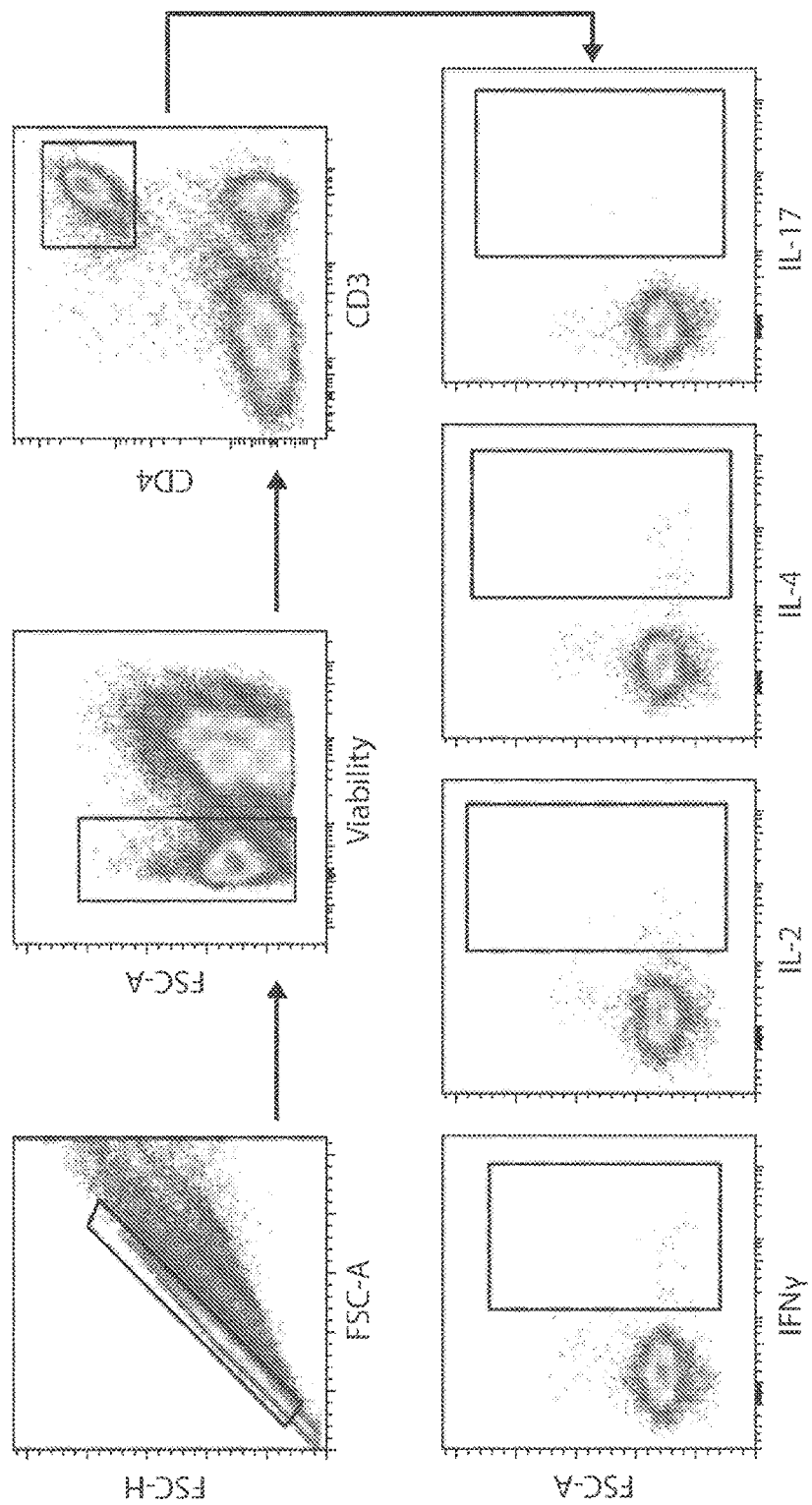
FIG. 3. Immunization with (cGAMP+alum) induces Th1 polarization in early life. Newborn mice were immunized with alum or (cGAMP+alum) as indicated in FIG. 2A. Ten days after boost (DOL 24) splenocytes were harvested, re-stimulated for 18 hours with rHA in the presence or absence of the co-stimulus αCD28, and cytokine production by CD4$^+$ T cells was assessed by intracellular flow cytometry. (A) Representative gating strategy. CD4$^+$ T cells were defined as viable singlet CD3$^+$CD4$^+$ cells. (B) Results are shown as the median, the 25th and 75th percentiles (boxes) and the 5th and 95th percentiles (whiskers) of 9-10 mice per group. **p<0.01 of in vitro CTRL vs. rHA vs. rHA+αCD28, ++p<0.01 of respective in vitro conditions compared to in vivo saline group, #p<0.05 and ##p<0.01 of respective in vitro conditions compared to in vivo alum group, determined by two-way ANOVA with Tukey's post hoc test.
Figure 3B:
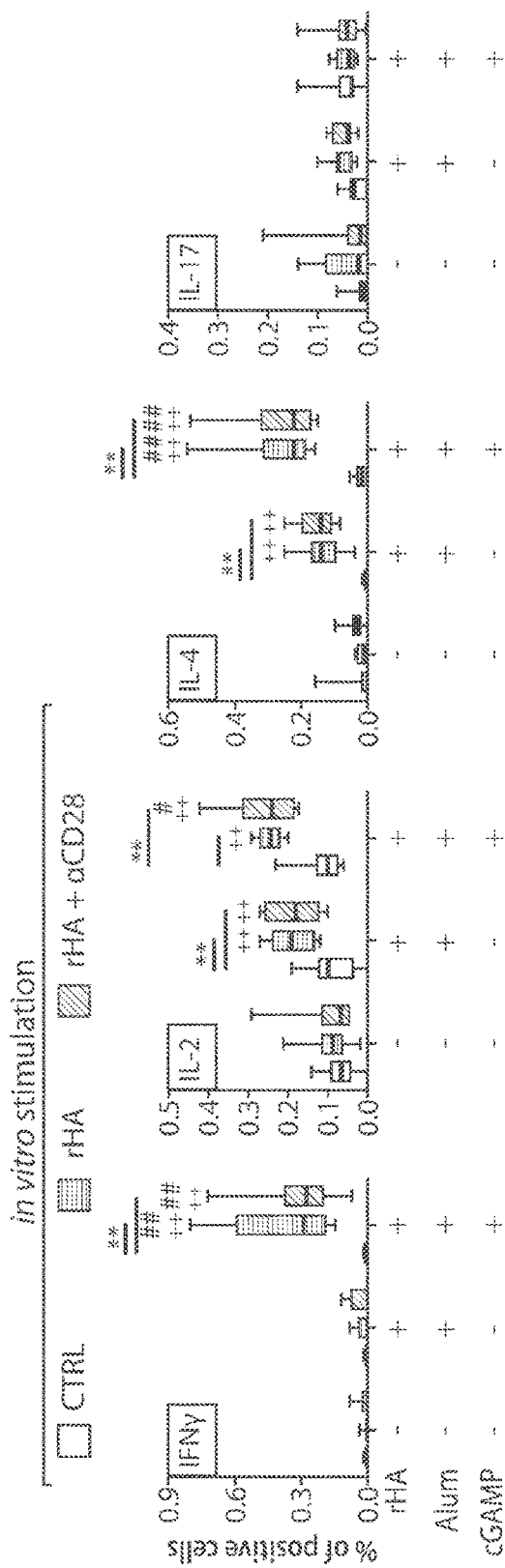
Figure 4:
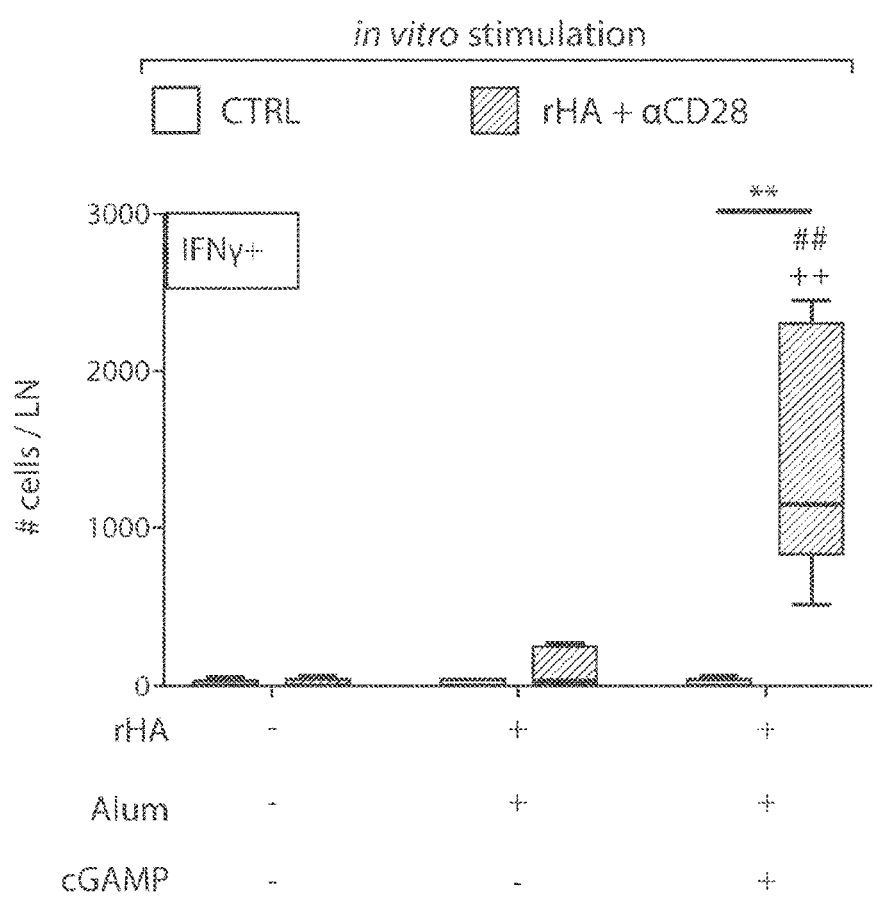
FIG. 4. Immunization with (cGAMP+alum) induces IFNγ-producing cells in dLNs of newborn mice. Newborn mice were immunized with alum or (cGAMP+alum) as indicated in FIG. 2A. 3 days after boost (DOL 17) cells were isolated from dLNs, re-stimulated for 18 hours with rHA+ αCD28, and the number of IFNγ-producing cells per LN was assessed by ELISPOT. Results are shown as the median, the 25th and 75th percentiles (boxes) and the 5th and 95th percentiles (whiskers) of 4-5 mice per group. **p<0.01 of in vitro CTRL vs. rHA+αCD28, ++p<0.01 of respective in vitro conditions compared to in vivo saline group, ##p<0.01 of respective in vitro conditions compared to in vivo alum group, determined by one-way ANOVA with Sidak's post hoc test.

IgG2a/c isotype switching is driven by IFNγ in vivo (Miyauchi et al., 2016), and reduced in early life, since newborns display reduced IFNγ production and Th1 polarization to many stimuli (Dowling and Levy, 2014, Zhang et al., 2017). Therefore, whether (cGAMP+alum) was able to modulate the polarization and cytokine production of antigen-specific T cells was investigated. Accordingly, newborn mice were immunized as indicated in FIG. 2A with alum or (cGAMP+alum). Ten days post-boost, splenocytes were harvested, re-stimulated with rHA in the presence or absence of the co-stimulus αCD28, and cytokine production by CD4+ T cells was measured by flow cytometry (FIG. 3A). While IL-2- and IL-4-producing cells were observed in both groups, IFNγ+ CD4+ T (Th1) cells were only detected among splenocytes isolated from mice immunized with (cGAMP+alum) (median percentages of IFNγ+ CD4+ T cells upon rHA re-stimulation: 0.000 for saline, 0.031 for alum and 0.295 for [cGAMP+alum] groups; upon rHA+αCD28 re-stimulation: 0.009 for saline, 0.021 for alum and 0.280 for [cGAMP+alum] groups). No IL-17 production was observed in any of the tested conditions (FIG. 3B). To corroborate this evidence, upon in vitro re-stimulation with rHA+αCD28, a higher number of IFNγ-producing cells in the draining lymph nodes (dLNs) of mice immunized with (cGAMP+alum) three days post-boost (FIG. 4) was found by ELISPOT.

Figure 5A:
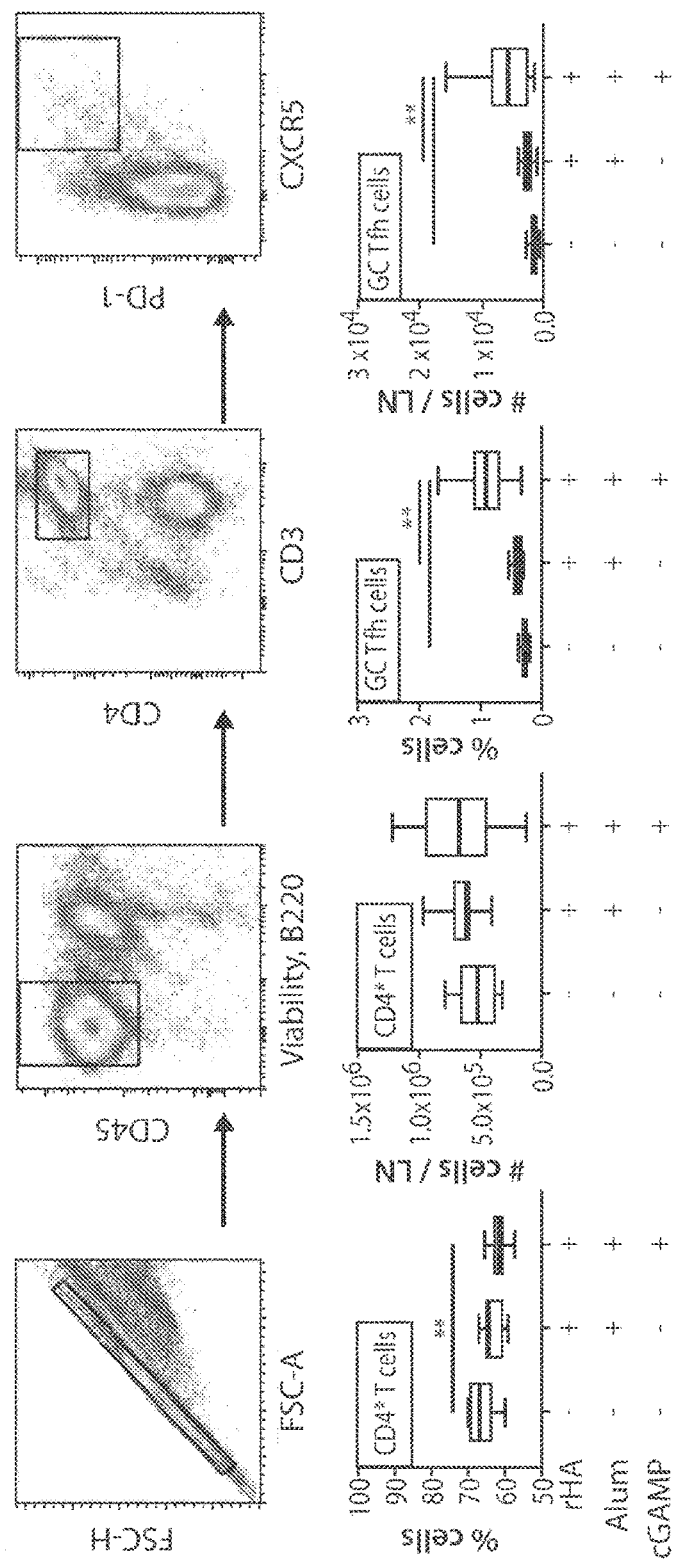
FIG. 5. Immunization with (cGAMP+alum) fosters the GC reaction. Newborn mice were immunized with alum or (cGAMP+alum) as indicated in FIG. 2A. Ten days after boost (DOL 24) cells were isolated from dLNs and the percentages and absolute numbers of CD4$^+$ T cells, B cells, GC Tfh and B cells were assessed by flow cytometry. (A, B top panels) Representative gating strategies. CD4$^+$ T cells were defined as viable singlet CD45$^+$ $^B$220$^-$ CD3$^+$ CD4$^+$ cells. GC Tfh cells were defined as viable singlet CD45$^+$ B220$^-$ CD3$^+$ CD4$^+$ CXCR5$^+$PD-1$^+$ cells. B cells were defined as viable singlet CD45$^+$ B220$^+$ CD3$^-$ cells. GC B cells were defined as viable singlet CD45$^+$ B220$^+$ CD3$^-$ GL-7$^+$ CD138$^-$ cells. (B) Results are shown as the median, the 25th and 75th percentiles (boxes) and the 5th and 95th percentiles (whiskers) of 9-10 mice per group. *p<0.05, **p<0.01 determined by two-way ANOVA with Holm-Sidak's post hoc test.
Figure 5B:
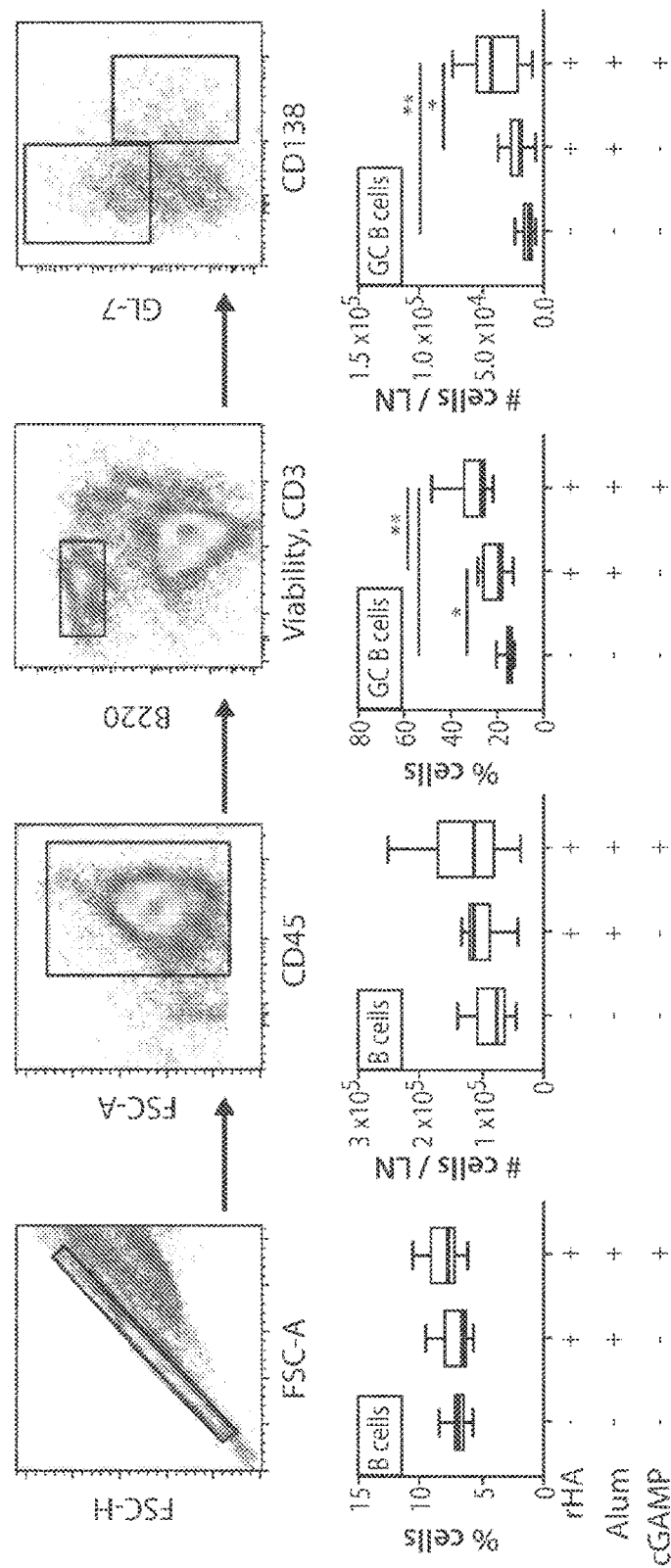

T cell-dependent antibody generation is initiated in GCs and guided by Tfh cells (Crotty, 2014, Victora and Nussenzweig, 2012). Since GCs are major sites for isotype switching, it was reasoned that immunization of newborn mice with (cGAMP+alum) might promote the GC reaction, thereby inducing IgG2a/c switching. To this aim, the percentages and absolute numbers of GC Tfh and B cells (respectively identified as viable singlet CD45+ B220− CD3+ CD4+ CXCR5+ PD-1+ and CD45+ CD3− B220+ GL-7+ CD138− cells) in dLNs ten days post-boost of newborn mice immunized with alum or (cGAMP+alum) were assessed by flow cytometry. Interestingly, a significant increase in the percentage (median: 0.275 for saline, 0.42 for alum and 0.925 for [cGAMP+alum]) and absolute number (median: 1360 for saline, 2558 for alum and 5754 for [cGAMP+alum]) of GC Tfh cells and the percentage (median: 14.4 for saline, 19.7 for alum and 27.35 for [cGAMP+alum]) and absolute number (median: 10975 for saline, 19878 for alum and 42524 for [cGAMP+alum]) of GC B cells only in the (cGAMP+alum) group (FIG. 5A) was found. Immunization with alum induced a small increase in the percentage (but not absolute number) of GC B cells, while only minor modifications of the percentages and absolute numbers of total CD4+ T cells and B cells were observed across different immunization groups (FIG. 5A, B).

Figure 6:
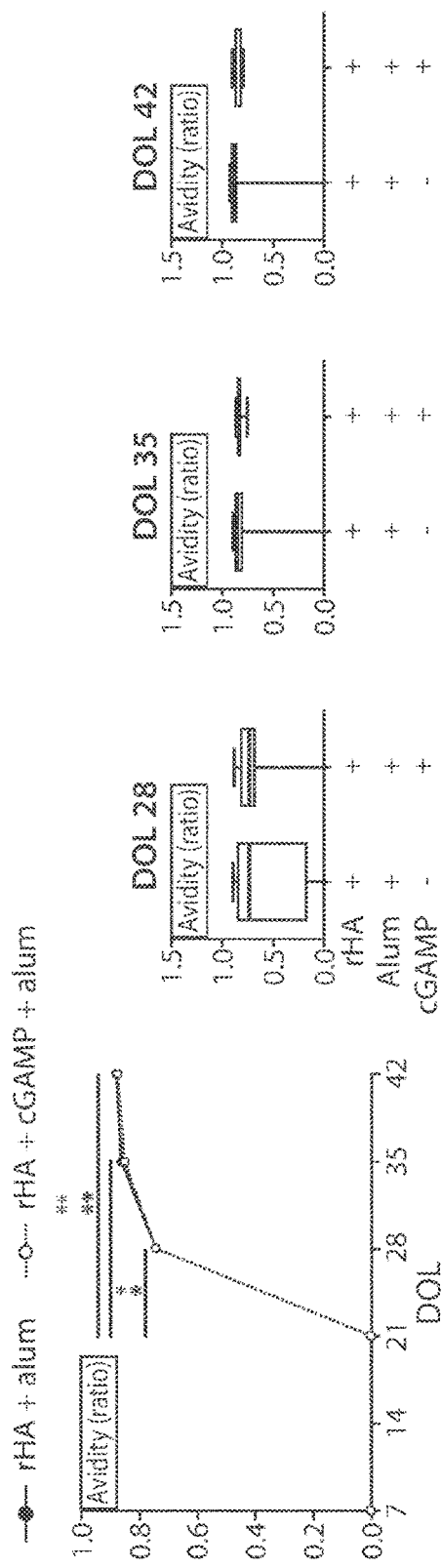
FIG. 6. Immunization with (cGAMP+alum) does not modulate rHA-specific IgG avidity. Newborn mice were immunized with rHA formulated with alum or (cGAMP+alum) and serum samples were collected as indicated in FIG. 2. Avidity of rHA-specific IgG was measured by ELISA and expressed as the ratio between the Log EC50 values obtained with and without ammonium thiocyanate treatment (0.5 M). Results are shown as median (left panel) or as the median, the 25th and 75th percentiles (boxes) and the 5th and 95th percentiles (whiskers) (right panels) of 7-8 newborn mice per group. *p<0.05, **p<0.01 determined by two-way ANOVA with Sidak's post hoc test (left panel) or Mann-Whitney test (right panels) post hoc tests.

The GC is also the site where the processes of somatic hypermutation of antibody variable region genes and generation of high affinity antibodies take place (Victora and Nussenzweig, 2012). To verify whether cGAMP modulates antibody affinity maturation, rHA-specific IgG avidity of newborn mice immunized with alum or (cGAMP+alum) was measured as indicated in FIG. 2A. Although a steep increase in antibody avidity 21 days post prime (DOL 28) was observed, which reached a plateau later on (28 [DOL 35] and 35 [DOL 42] days post-prime), no differences between the two groups were detected at any time point (FIG. 6).

Overall, these results demonstrate that the addition of cGAMP to alum enhanced induction of IFNγ-producing T cells and appeared to foster a GC reaction, which might in turn drive IgG2a/c isotype switching in the early life immunization model.

Figure 7:
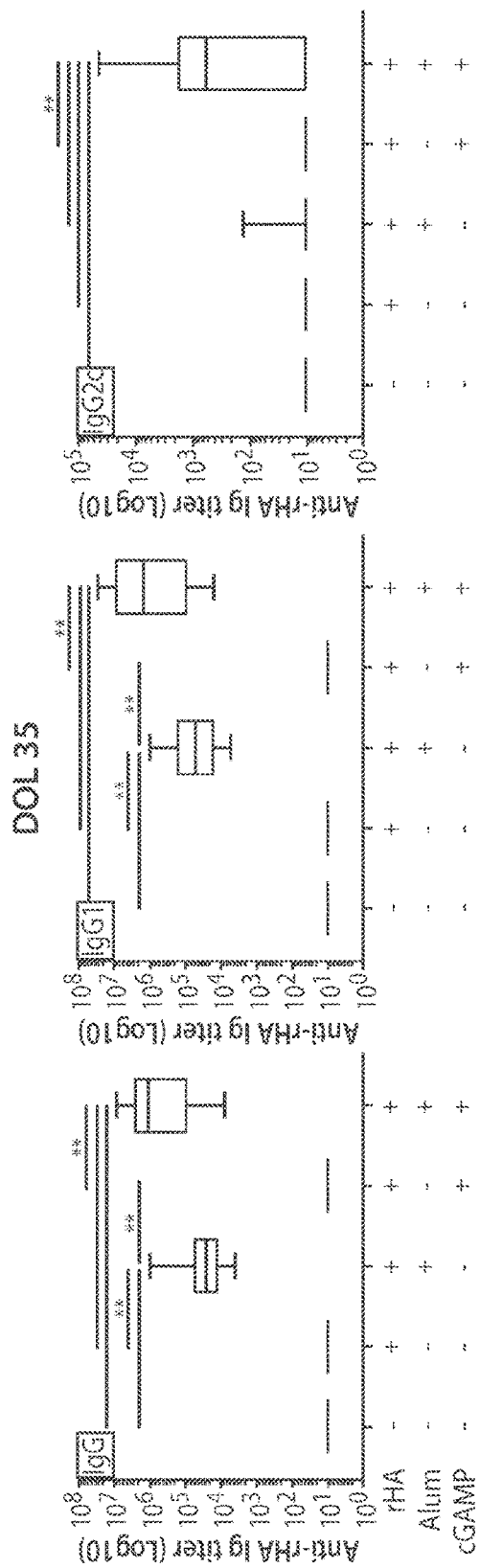
FIG. 7. Single dose immunization of newborn mice with (cGAMP+alum) significantly increases anti-rHA IgG2c titers. Newborn mice were immunized i.m. with saline, rHA alone or formulated with alum, cGAMP or (cGAMP+alum) and antibody titers for rHA-specific IgG, IgG1 and IgG2c were determined by ELISA in serum samples collected 28 days after boost (DOL 35). Results are shown as the median, the 25th and 75th percentiles (boxes) and the 5th and 95th percentiles (whiskers) of 9-13 mice per group. **p<0.01 determined by Kruskall-Wallis with Dunn's post hoc test.

3.5 Single-Dose Immunization with (cGAMP+Alum) Induces rHA-Specific IgG2c Antibodies The results obtained so far supported the efficacy of (cGAMP+alum) as an adjuvantation system in a prime/boost model of neonatal murine immunization. Of note, a single dose immunization strategy capable of enhancing antigen-specific antibody titers would be highly desirable early in life. To this end, newborn mice were immunized with rHA formulated with alum, cGAMP or (cGAMP+alum). Distinct from its effects in prime/boost immunization, cGAMP without alum did not induce detectable anti-rHA IgG, IgG1 and IgG2c titers. Alum and (cGAMP+alum) significantly increased anti-rHA IgG and IgG1 titers (median anti-rHA IgG and IgG1 titers: respectively $26.74\times10^3$ and $52.08\times10^3$ for alum; respectively $1.07\times10^6$ and $1.48\times10^6$ for [cGAMP+alum]). Interestingly, only (cGAMP+alum) induced detectable levels of anti-rHA IgG2c (median: 571.9), albeit at lower levels compared to prime/boost immunization (FIG. 7). Altogether, these results demonstrate that (cGAMP+alum) is an effective adjuvantation system also for single dose early life immunization.

4. Discussion

Over the past decades many PRRs and their agonists have been identified, and the molecular definition of their mechanisms of action and immunostimulatory properties has paved the way for new classes of adjuvants (Coffman et al., 2010, Dowling and Levy, 2015). For example, the TLR4 agonist monophosphoryl lipid A is employed in different FDA-approved vaccine formulations. Despite this wealth of knowledge, the portfolio of adjuvants approved or in clinical development for the newborn and the young infant is much narrower, in part due to the limited knowledge of the immune system early in life (Bergmann-Leitner and Leitner, 2014, Dowling and Levy, 2014, Zhang et al., 2017). Notwithstanding these limitations, in vitro and pre-clinical in vivo studies have shown that targeting some PRRs, in particular TLR7/8 (Dowling et al., 2017, Dowling et al., 2013, Dowling et al., 2017, Ganapathi et al., 2015, Levy et al., 2006, Levy et al., 2004, Philbin et al., 2012), potently activates newborn immune cells and markedly enhances vaccine efficacy early in life. Here, by combining an in vitro analysis of newborn BMDC activation in response to PRR agonists and in vivo immunization models the STING agonist cGAMP was identified as adjuvant candidate for early life immunization. In particular, it was demonstrated that immunization of newborn mice with cGAMP formulated with alum appears to foster the GC reaction as well as features of IFNγ-driven type 1 immunity, namely switching toward IgG2a/c subclass and Th1 polarization.

Although there is no comprehensive consensus on whether and how in vitro models can predict the in vivo effect of candidate adjuvants, the use of DCs has some advantages for assessing their activity in vitro (Dowling and Levy, 2014, Kastenmuller et al., 2014, Kreutz et al., 2013, Merad et al., 2013). First, DCs are the most prominent subset of antigen presenting cells. Second, they express many PRRs. Third, DCs can be employed to recapitulate age-specific differences. Although isolating primary DCs from spleen and lymph nodes of neonatal mice would be ideal, this approach is cumbersome if not impossible due to low cell yield (Dakic et al., 2004, Sun et al., 2003). Therefore, a neonatal BMDC model was developed and characterized, and phenotypic and functional differences between neonatal and adult BMDCs were found. Most importantly, by comparing the activation profiles of neonatal and adult BMDCs, the STING agonist cGAMP was identified to induce their maturation (e.g. upregulation of CD40, CD80 and CD86). Other PRR ligands that did not activate newborn BMDCs in vitro may still act as adjuvants in vivo. Therefore, further studies, especially of combination formulations, are required to define the predictive value of the in vitro newborn BMDC system.

CDNs including cGAMP have been tested as candidate adjuvants in experimental models of parenteral or mucosal adult immunization (Baird et al., 2016, Blaauboer et al., 2014, Carroll et al., 2016, Corrales et al., 2015, Curran et al., 2016, Ebensen et al., 2011, Ebensen et al., 2007, Fu et al., 2015, Hanson et al., 2015, Karaolis et al., 2007, Li et al., 2013, Libanova et al., 2010, Madhun et al., 2011, Martin et al., 2017, Matos et al., 2017, Nakamura et al., 2015, Ogunniyi et al., 2008, Wang et al., 2016). In the present work, mice were immunized by the intramuscular route as it is commonly employed for pediatric vaccines: a new formulation specific for intramuscular injection may fit easily with other vaccines in the pediatric vaccination schedule, while intranasal immunization against influenza virus, for example, is currently not recommended by the CDC (Grohskopf et al., 2017). It was found that free cGAMP, simply injected together with the model antigen, is much less effective in newborn than in adult mice at increasing antigen-specific antibody titers. Remarkably, cGAMP formulated with alum induces relatively high titers of antigen-specific IgG2a/c compared to alum or cGAMP alone, especially in newborn mice immunized with prime/boost or single dose schedules. The explanation for this might be that about 60% of cGAMP adsorbs onto alum in vitro, which also suggests there is still the possibility of further optimizing this formulation and increasing the percentage of adsorbed cGAMP by modification of the adsorption pH, buffer and alum to cGAMP ratio. Interestingly, it has already been reported that CDNs tend to diffuse in the bloodstream after injection, while their nanoparticle formulations deliver CDNs to the dLNs (Hanson et al., 2015). It is tempting to speculate that the same phenomenon might explain the differences in the efficacy between cGAMP and (cGAMP+alum). In addition, it will be interesting to compare the effect of optimized (cGAMP+alum) and nanoparticle-based cGAMP formulations in the early life immunization model.

Newborns and young infants have a distinct immunity with an impairment of IFNγ-driven type 1 immunity, which in turn leads to reduced vaccine efficacy and higher risk of infections (Dowling and Levy, 2014, Zhang et al., 2017). By using (cGAMP+alum) as adjuvantation strategy for early life immunization cardinal features of type 1 immunity were induced: 1) IFNγ production by antigen-specific CD4$^+$ T cells and 2) relatively high titers of antigen-specific IgG2a/c. As IFNγ promotes isotype switching toward IgG2a/c in vivo (Miyauchi et al., 2016), these two events are likely linked. The importance of inducing this antibody subclass relies in its higher affinity toward Fcγ receptors expressed on myeloid cells, which endows this subclass with greater effector functions (e.g. induction of phagocytosis, complement fixation) that may be important for protecting from infections (Bournazos and Ravetch, 2017, Gunn and Alter, 2016). The results suggest that (cGAMP+alum) increases the magnitude of the GC reaction, known to be impaired in early life (Debock et al., 2013, Mastelic et al., 2012), by inducing higher percentages and absolute numbers of GC Tfh and B cells in dLNs. Although it cannot be excluded that the GC reaction induced by alum follows a different kinetics, these results might represent the cellular correlate of the isotype switching and early IgG2a/c production observed in the (cGAMP+alum) group. Altogether, the data point to a relevant effect of the (cGAMP+alum) formulation on the humoral and cellular immune responses elicited upon immunization early in life.

In conclusion, it was demonstrated that cGAMP is a promising and robust adjuvant candidate for early life immunization. It was also shown herein that cGAMP formulated with alum potently enhances humoral and cellular aspects of type 1 immunity in early life. Since the recombinant hemagglutinin influenza vaccine was used throughout this work, the results is applicable to influenza immunization. Use of (cGAMP+alum) may also represent a general strategy to elicit type 1 immunity toward protein antigens for early life immunization.

5. References

Bagnoli, F., Fontana, M. R., Soldaini, E., Mishra, R. P., Fiaschi, L., Cartocci, E., et al. (2015). Vaccine composition formulated with a novel TLR7-dependent adjuvant induces high and broad protection against *Staphylococcus aureus*. Proc Natl Acad Sci USA. 112(12):3680-3685. doi: 10.1073/pnas.1424924112.

Baird, J. R., Friedman, D., Cottam, B., Dubensky, T. W., Jr., Kanne, D. B., Bambina, S., et al. (2016). Radiotherapy Combined with Novel STING-Targeting Oligonucleotides Results in Regression of Established Tumors. *Cancer Res.* 76(1):50-61. doi: 10.1158/0008-5472. CAN-14-3619.

Bergmann-Leitner, E. S., Leitner, W. W. (2014). Adjuvants in the Driver's Seat: How Magnitude, Type, Fine Specificity and Longevity of Immune Responses Are Driven by Distinct Classes of Immune Potentiators. *Vaccines (Basel)*. 2(2):252-296. doi: 10.3390/vaccines2020252.

Bhutta, Z. A., Black, R. E. (2013). Global maternal, newborn, and child health—so near and yet so far. *N Engl J Med.* 369(23):2226-2235. doi: 10.1056/NEJMra1111853.

Blaauboer, S. M., Gabrielle, V. D., Jin, L. (2014). MPYS/STING-mediated TNF-alpha, not type I IFN, is essential for the mucosal adjuvant activity of (3'-5')-cyclic-di-guanosine-monophosphate in vivo. *J Immunol.* 192(1):492-502. doi: 10.4049/jimmunol.1301812.

Bournazos, S., Ravetch, J. V. (2017). Fcgamma Receptor Function and the Design of Vaccination Strategies. *Immunity.* 47(2):224-233. doi: 10.1016/j.immuni.2017.07.009.

Carroll, E. C., Jin, L., Mori, A., Munoz-Wolf, N., Oleszycka, E., Moran, H. B. T., et al. (2016). The Vaccine Adjuvant Chitosan Promotes Cellular Immunity via DNA Sensor cGAS-STING-Dependent Induction of Type I Interferons. *Immunity.* 44(3):597-608. doi: 10.1016/j.immuni.2016.02.004.

Chen, Q., Sun, L., Chen, Z. J. (2016). Regulation and function of the cGAS-STING pathway of cytosolic DNA sensing. *Nat Immunol.* 17(10):1142-1149. doi: 10.1038/ni.3558.

Coffman, R. L., Sher, A., Seder, R. A. (2010). Vaccine adjuvants: putting innate immunity to work. *Immunity.* 33(4):492-503. doi: 10.1016/j.immuni.2010.10.002.

Corrales, L., Glickman, L. H., McWhirter, S. M., Kanne, D. B., Sivick, K. E., Katibah, G. E., et al. (2015). Direct Activation of STING in the Tumor Microenvironment Leads to Potent and Systemic Tumor Regression and Immunity. *Cell Rep.* 11(7):1018-1030. doi: 10.1016/j.celrep.2015.04.031.

Crotty, S. (2014). T follicular helper cell differentiation, function, and roles in disease. *Immunity.* 41(4):529-542. doi: 10.1016/j.immuni.2014.10.004.

Curran, E., Chen, X., Corrales, L., Kline, D. E., Dubensky, T. W., Jr., Duttagupta, P., et al. (2016). STING Pathway Activation Stimulates Potent Immunity against Acute Myeloid Leukemia. *Cell Rep.* 15(11):2357-2366. doi: 10.1016/j.celrep.2016.05.023.

Dakic, A., Shao, Q. X., D'Amico, A., O'Keeffe, M., Chen, W. F., Shortman, K., et al. (2004). Development of the dendritic cell system during mouse ontogeny. *J Immunol.* 172(2):1018-1027.

Debock, I., Jaworski, K., Chadlaoui, H., Delbauve, S., Passon, N., Twyffels, L., et al. (2013). Neonatal follicular Th cell responses are impaired and modulated by IL-4. *J Immunol.* 191(3):1231-1239. doi: 10.4049/jimmunol.1203288.

Dowling, D., Hamilton, C. M., O'Neill, S. M. (2008). A comparative analysis of cytokine responses, cell surface marker expression and MAPKs in DCs matured with LPS compared with a panel of TLR ligands. *Cytokine.* 41(3):254-262. doi: 10.1016/j.cyto.2007.11.020.

Dowling, D. J., Levy, O. (2014). Ontogeny of early life immunity. *Trends Immunol.* 35(7):299-310. doi: 10.1016/j.it.2014.04.007.

Dowling, D. J., Levy, O. (2015). Pediatric Vaccine Adjuvants: Components of the Modern Vaccinologist's Toolbox. *Pediatr Infect Dis J.* 34(12):1395-1398. doi: 10.1097/INF.0000000000000893.

Dowling, D. J., Scott, E. A., Scheid, A., Bergelson, I., Joshi, S., Pietrasanta, C., et al. (2017). Toll-like receptor 8 agonist nanoparticles mimic immunomodulating effects of the live BCG vaccine and enhance neonatal innate and adaptive immune responses. *J Allergy Clin Immunol.* doi: 10.1016/j.jaci.2016.12.985.

Dowling, D. J., Tan, Z., Prokopowicz, Z. M., Palmer, C. D., Matthews, M. A., Dietsch, G. N., et al. (2013). The ultra-potent and selective TLR8 agonist VTX-294 activates human newborn and adult leukocytes. *PLoS One.* 8(3):e58164. doi: 10.1371/journal.pone.0058164.

Dowling, D. J., van Haren, S. D., Scheid, A., Bergelson, I., Kim, D., Mancuso, C. J., et al. (2017). TLR7/8 adjuvant overcomes newborn hyporesponsiveness to pneumococcal conjugate vaccine at birth. *JCI Insight.* 2(6):e91020. doi: 10.1172/jci.insight.91020.

Dubensky, T. W., Jr., Kanne, D. B., Leong, M. L. (2013). Rationale, progress and development of vaccines utilizing STING-activating cyclic dinucleotide adjuvants. *Ther Adv Vaccines.* 1(4):131-143. doi: 10.1177/2051013613501988.

Ebensen, T., Libanova, R., Schulze, K., Yevsa, T., Morr, M., Guzman, C. A. (2011). Bis-(3',5')-cyclic dimeric adenosine monophosphate: strong Th1/Th2/Th17 promoting mucosal adjuvant. *Vaccine.* 29(32):5210-5220. doi: 10.1016/j.vaccine.2011.05.026.

Ebensen, T., Schulze, K., Riese, P., Link, C., Morr, M., Guzman, C. A. (2007). The bacterial second messenger cyclic diGMP exhibits potent adjuvant properties. *Vaccine.* 25(8):1464-1469. doi: 10.1016/j.vaccine.2006.10.033.

Fu, J., Kanne, D. B., Leong, M., Glickman, L. H., McWhirter, S. M., Lemmens, E., et al. (2015). STING agonist formulated cancer vaccines can cure established tumors resistant to PD-1 blockade. *Sci Transl Med.* 7(283):283ra252. doi: 10.1126/scitranslmed.aaa4306.

Ganapathi, L., Van Haren, S., Dowling, D. J., Bergelson, I., Shukla, N. M., Malladi, S. S., et al. (2015). The Imidazoquinoline Toll-Like Receptor-7/8 Agonist Hybrid-2 Potently Induces Cytokine Production by Human Newborn and Adult Leukocytes. *PLoS One.* 10(8):e0134640. doi: 10.1371/journal.pone.0134640.

Grohskopf, L. A., Sokolow, L. Z., Broder, K. R., Walter, E. B., Bresee, J. S., Bresee, A. M., et al. (2017). Prevention and Control of Seasonal Influenza with Vaccines: Recommendations of the Advisory Committee on Immunization Practices—United States, 2017-18 Influenza Season. *MMWR Recomm Rep* 66 (No. RR-2):1-20. doi: http://dx.doi.org/10.15585/mmwr.rr6602a1.

Gunn, B. M., Alter, G. (2016). Modulating Antibody Functionality in Infectious Disease and Vaccination. *Trends Mol Med.* 22(11):969-982. doi: 10.1016/j.molmed.2016.09.002.

Gutjahr, A., Tiraby, G., Perouzel, E., Verrier, B., Paul, S. (2016). Triggering Intracellular Receptors for Vaccine Adjuvantation. *Trends Immunol.* 37(9):573-587. doi: 10.1016/j.it.2016.07.001.

Hanson, M. C., Crespo, M. P., Abraham, W., Moynihan, K. D., Szeto, G. L., Chen, S. H., et al. (2015). Nanoparticulate STING agonists are potent lymph node-targeted vaccine adjuvants. *J Clin Invest.* 125(6):2532-2546. doi: 10.1172/JCI79915.

Helft, J., Bottcher, J., Chakravarty, P., Zelenay, S., Huotari, J., Schraml, B. U., et al. (2015). GM-CSF Mouse Bone Marrow Cultures Comprise a Heterogeneous Population of CD11c(+)MHCII(+) Macrophages and Dendritic Cells. *Immunity.* 42(6):1197-1211. doi: 10.1016/j.immuni.2015.05.018.

Karaolis, D. K., Means, T. K., Yang, D., Takahashi, M., Yoshimura, T., Muraille, E., et al. (2007). Bacterial c-di-GMP is an immunostimulatory molecule. *J Immunol.* 178(4):2171-2181. doi:

Kastenmuller, W., Kastenmuller, K., Kurts, C., Seder, R. A. (2014). Dendritic cell-targeted vaccines—hope or hype? *Nat Rev Immunol.* 14(10):705-711. doi: 10.1038/nri3727.

Kollmann, T. R., Kampmann, B., Mazmanian, S. K., Marchant, A., Levy, 0. (2017). Protecting the Newborn and Young Infant from Infectious Diseases: Lessons from Immune Ontogeny. *Immunity.* 46(3):350-363. doi: 10.1016/j.immuni.2017.03.009.

Kreutz, M., Tacken, P. J., Figdor, C. G. (2013). Targeting dendritic cells—why bother? *Blood.* 121(15):2836-2844. doi: 10.1182/blood-2012-09-452078.

Lemoine, S., Jaron, B., Tabka, S., Ettreiki, C., Deriaud, E., Zhivaki, D., et al. (2015). Dectin-1 activation unlocks IL12A expression and reveals the TH1 potency of neonatal dendritic cells. *J Allergy Clin Immunol.* 136(5):1355-1368 e1351-1315. doi: 10.1016/j.jaci.2015.02.030.

Levy, O., Goriely, S., Kollmann, T. R. (2013). Immune response to vaccine adjuvants during the first year of life. *Vaccine.* 31(21):2500-2505. doi: 10.1016/j.vaccine.2012.10.016.

Levy, O., Suter, E. E., Miller, R. L., Wessels, M. R. (2006). Unique efficacy of Toll-like receptor 8 agonists in activating human neonatal antigen-presenting cells. *Blood.* 108(4):1284-1290. doi: 10.1182/blood-2005-12-4821.

Levy, O., Zarember, K. A., Roy, R. M., Cywes, C., Godowski, P. J., Wessels, M. R. (2004). Selective impairment of TLR-mediated innate immunity in human newborns: neonatal blood plasma reduces monocyte TNF-alpha induction by bacterial lipopeptides, lipopolysaccharide, and imiquimod, but preserves the response to R-848. *J Immunol.* 173(7):4627-4634. doi:

Li, X. D., Wu, J., Gao, D., Wang, H., Sun, L., Chen, Z. J. (2013). Pivotal roles of cGAS-cGAMP signaling in antiviral defense and immune adjuvant effects. *Science.* 341 (6152):1390-1394. doi: 10.1126/science.1244040.

Libanova, R., Ebensen, T., Schulze, K., Bruhn, D., Norder, M., Yevsa, T., et al. (2010). The member of the cyclic di-nucleotide family bis-(3',5')-cyclic dimeric inosine monophosphate exerts potent activity as mucosal adjuvant. *Vaccine.* 28(10):2249-2258. doi: 10.1016/j.vaccine.2009.12.045.

Liu, L., Johnson, H. L., Cousens, S., Perin, J., Scott, S., Lawn, J. E., et al. (2012). Global, regional, and national causes of child mortality: an updated systematic analysis for 2010 with time trends since 2000. *Lancet.* 379(9832): 2151-2161. doi: 10.1016/S0140-6736(12)60560-1.

Lofano, G., Mancini, F., Salvatore, G., Cantisani, R., Monaci, E., Carrisi, C., et al. (2015). Oil-in-Water Emulsion MF59 Increases Germinal Center B Cell Differentiation and Persistence in Response to Vaccination. *J Immunol.* 195(4):1617-1627. doi: 10.4049/jimmunol.1402604.

Lutz, M. B., Kukutsch, N., Ogilvie, A. L., Rossner, S., Koch, F., Romani, N., et al. (1999). An advanced culture method for generating large quantities of highly pure dendritic cells from mouse bone marrow. *J Immunol Methods.* 223(1):77-92. doi:

Madhun, A. S., Haaheim, L. R., Nostbakken, J. K., Ebensen, T., Chichester, J., Yusibov, V., et al. (2011). Intranasal c-di-GMP-adjuvanted plant-derived H5 influenza vaccine induces multifunctional Th1 CD4+ cells and strong mucosal and systemic antibody responses in mice. *Vaccine.* 29(31):4973-4982. doi: 10.1016/j.vaccine.2011.04.094.

Martin, T. L., Jee, J., Kim, E., Steiner, H. E., Cormet-Boyaka, E., Boyaka, P. N. (2017). Sublingual targeting of STING with 3'3'-cGAMP promotes systemic and mucosal immunity against anthrax toxins. *Vaccine.* 35(18):2511-2519. doi: 10.1016/j.vaccine.2017.02.064.

Mastelic, B., Kamath, A. T., Fontannaz, P., Tougne, C., Rochat, A. F., Belnoue, E., et al. (2012). Environmental and T cell-intrinsic factors limit the expansion of neonatal follicular T helper cells but may be circumvented by specific adjuvants. *J Immunol.* 189(12):5764-5772. doi: 10.4049/jimmunol.1201143.

Matos, M. N., Cazorla, S. I., Schulze, K., Ebensen, T., Guzman, C. A., Malchiodi, E. L. (2017). Immunization with Tc52 or its amino terminal domain adjuvanted with c-di-AMP induces Th17+Th1 specific immune responses and confers protection against *Trypanosoma cruzi*. *PLoS Negl Trop Dis.* 11(2):e0005300. doi: 10.1371/journal.pntd.0005300.

Merad, M., Sathe, P., Helft, J., Miller, J., Mortha, A. (2013). The dendritic cell lineage: ontogeny and function of dendritic cells and their subsets in the steady state and the inflamed setting. *Annu Rev Immunol.* 31:563-604. doi: 10.1146/annurev-immunol-020711-074950.

Miyauchi, K., Sugimoto-Ishige, A., Harada, Y., Adachi, Y., Usami, Y., Kaji, T., et al. (2016). Protective neutralizing influenza antibody response in the absence of T follicular helper cells. *Nat Immunol.* 17(12):1447-1458. doi: 10.1038/ni.3563.

Nakamura, T., Miyabe, H., Hyodo, M., Sato, Y., Hayakawa, Y., Harashima, H. (2015). Liposomes loaded with a STING pathway ligand, cyclic di-GMP, enhance cancer immunotherapy against metastatic melanoma. *J Control Release.* 216:149-157. doi: 10.1016/j jconrel.2015.08.026.

Nakaya, H. I., Clutterbuck, E., Kazmin, D., Wang, L., Cortese, M., Bosinger, S. E., et al. (2016). Systems biology of immunity to MF59-adjuvanted versus nonadjuvanted trivalent seasonal influenza vaccines in early childhood. *Proc Natl Acad Sci USA.* 113(7):1853-1858. doi: 10.1073/pnas.1519690113.

Ogunniyi, A. D., Paton, J. C., Kirby, A. C., McCullers, J. A., Cook, J., Hyodo, M., et al. (2008). c-di-GMP is an effective immunomodulator and vaccine adjuvant against pneumococcal infection. *Vaccine*. 26(36):4676-4685. doi: 10.1016/j.vaccine.2008.06.099.

Pan, X., Ji, Z., Xue, J. (2016). Percentage of Peripheral CD19+CD24hiCD38hi Regulatory B Cells in Neonatal Sepsis Patients and Its Functional Implication. *Med Sci Monit*. 22:2374-2378.

Pettengill, M. A., Levy, 0. (2016). Circulating Human Neonatal Naive B Cells are Deficient in CD73 Impairing Purine Salvage. Front Immunol. 7:121. doi: 10.3389/fimmu.2016.00121.

Pettengill, M. A., van Haren, S. D., Li, N., Dowling, D. J., Bergelson, I., Jans, J., et al. (2016). Distinct TLR-mediated cytokine production and immunoglobulin secretion in human newborn naive B cells. *Innate Immun*. 22(6): 433-443. doi: 10.1177/1753425916651985.

Philbin, V. J., Dowling, D. J., Gallington, L. C., Cortes, G., Tan, Z., Suter, E. E., et al. (2012). Imidazoquinoline Toll-like receptor 8 agonists activate human newborn monocytes and dendritic cells through adenosine-refractory and caspase-1-dependent pathways. *J Allergy Clin Immunol*. 130(1):195-204 e199. doi: 10.1016/j.jaci.2012.02.042.

Siegrist, C. A., Aspinall, R. (2009). B-cell responses to vaccination at the extremes of age. *Nat Rev Immunol*. 9(3):185-194. doi: 10.1038/nri2508.

Sun, C. M., Deriaud, E., Leclerc, C., Lo-Man, R. (2005). Upon TLR9 signaling, CD5+ B cells control the IL-12-dependent Th1-priming capacity of neonatal DCs. *Immunity*. 22(4):467-477. doi: 10.1016/j.immuni.2005.02.008.

Sun, C. M., Fiette, L., Tanguy, M., Leclerc, C., Lo-Man, R. (2003). Ontogeny and innate properties of neonatal dendritic cells. *Blood*. 102(2):585-591. doi: 10.1182/blood-2002-09-2966.

Thompson, W. W., Shay, D. K., Weintraub, E., Brammer, L., Bridges, C. B., Cox, N.J., et al. (2004). Influenza-associated hospitalizations in the United States. *JAMA*. 292(11):1333-1340. doi: 10.1001/jama.292.11.1333.

van Haren, S. D., Dowling, D. J., Foppen, W., Christensen, D., Andersen, P., Reed, S. G., et al. (2016). Age-Specific Adjuvant Synergy: Dual TLR7/8 and Mincle Activation of Human Newborn Dendritic Cells Enables Th1 Polarization. *J Immunol*. 197(11):4413-4424. doi: 10.4049/jimmunol.1600282.

Victora, G. D., Nussenzweig, M. C. (2012). Germinal centers. *Annu Rev Immunol*. 30:429-457. doi: 10.1146/annurev-immunol-020711-075032.

Wang, J., Li, P., Wu, M. X. (2016). Natural STING Agonist as an "Ideal" Adjuvant for Cutaneous Vaccination. *J Invest Dermatol*. 136(11):2183-2191. doi: 10.1016/j.jid.2016.05.105.

Zanoni, I., Bodio, C., Broggi, A., Ostuni, R., Caccia, M., Collini, M., et al. (2012). Similarities and differences of innate immune responses elicited by smooth and rough LPS. *Immunol Lett*. 142(1-2):41-47. doi: 10.1016/j.imlet.2011.12.002.

Zhang, X., Deriaud, E., Jiao, X., Braun, D., Leclerc, C., Lo-Man, R. (2007). Type I interferons protect neonates from acute inflammation through interleukin 10-producing B cells. *J Exp Med*. 204(5):1107-1118. doi: 10.1084/jem.20062013.

Zhang, X., Zhivaki, D., Lo-Man, R. (2017). Unique aspects of the perinatal immune system. *Nat Rev Immunol*. 17(8): 495-507. doi: 10.1038/nri.2017.54.

Zhivaki, D., Lemoine, S., Lim, A., Morva, A., Vidalain, P. O., Schandene, L., et al. (2017). Respiratory Syncytial Virus Infects Regulatory B Cells in Human Neonates via Chemokine Receptor CX3CR1 and Promotes Lung Disease Severity. *Immunity*. 46(2):301-314. doi: 10.1016/j.immuni.2017.01.010.

TABLE 1 cGAMP adsorption onto alum as function of time as assessed by RP-HPLC
cGAMP adsorbed onto alum - incubated at 37° C.

| Time point | Peak Area (mAU) | % Adsorbed to Alum |
|---|---|---|
| 15 min | 22.53 | 63.00 |
| 30 min | 22.93 | 62.34 |
| 1 hour | 22.22 | 63.51 |
| 2 hours | 20.83 | 65.79 |
| 4 hours | 21.02 | 65.48 |
| 24 hours | 15.02 | 75.33 |
| Alum control (no cGAMP) | 0.53 | ND |
| Saline | 0.55 | ND |

RP-HPLC, reverse-phase high performance liquid chromatography

TABLE 2

List of fluorochromes and antibodies used in the study for flow cytometry stainings

| Target | Clone | Fluorochrome | Dilution | Company |
|---|---|---|---|---|
| CD11c | HL3 | BV421 | 1:200 | BD Biosciences |
| CD11c | N418 | Alexa-700 | 1:400 | Biolegend |
| MHCII | M5/114 | APC | 1:200 | Biolegend |
| CD40 | 3/23 | PE-Dazzle 594 | 1:50 | Biolegend |
| CD80 | 16-10A1 | Alexa Fluor 488 | 1:50 | Biolegend |
| CD86 | GL-1 | PE | 1:150 | BD Biosciences |
| CD11b | M1/70 | Alexa Fluor 488 | 1:400 | Biolegend |
| CD115 | AFS98 | Alexa Fluor 488 | 1:100 | Biolegend |
| CD117 | 2B8 | BV421 | 1:40 | Biolegend |
| CD135 | A2F10 | PE | 1:40 | Biolegend |
| CD64 | X54-5/7.1 | PerCP-Cy5.5 | 1:200 | Biolegend |
| F4/80 | BM8 | APC | 1:200 | eBioscience |
| CD45 | 30-F11 | PerCP-Cy5.5 | 1:80 | Biolegend |
| IFNγ | XMG1.2 | APC | 1:40 | Biolegend |
| IL-2 | JES6-5H4 | BV421 | 1:40 | Biolegend |
| IL-4 | 11B11 | PE | 1:40 | Biolegend |
| IL-17A | TCH18-H10 | PE-CF594 | 1:40 | BD Biosciences |
| CD3 | 17A2 | FITC | 1:40 | BD Biosciences |
| CD3 | 17A2 | APC-Fire750 | 1:40 | Biolegend |
| CD4 | GK1.5 | PerCP-Cy5.5 | 1:40 | Biolegend |
| CXCR5 | L138D7 | BV421 | 1:40 | Biolegend |
| PD-1 | 29F.1A12 | PE | 1:40 | Biolegend |
| B220 | RA3-6B2 | Alexa Fluor 488 | 1:40 | Biolegend |
| B220 | RA3-6B2 | APC-eFluor780 | 1:40 | eBioscience |
| CD138 | 281-2 | BV421 | 1:40 | Biolegend |
| GL-7 | GL7 | PE | 1:80 | Biolegend |
| Viability | | eFluor 780 | 1:1000 | eBioscience |
| Mouse BD Fc Block | 2.4G2 | | 1:80 | BD Biosciences |

TABLE 3

List of PRRs agonists used to stimulate BMDCs from newborn and adult mice

| Receptor | Agonist Name | Concentration Range |
|---|---|---|
| Toll Like Receptors (TLR) agonists | | |
| TLR1 | PAM3CSK4 | 1, 10, 100 ng/ml |
| TLR2 | PAM2CSK4 | 1, 10, 100 ng/ml |
| TLR3 | Poly (I:C) HMW | 1, 10, 100 ng/ml |
| TLR4 | Synthetic monophosphoryl Lipid A (MPLA) | 1, 10, 100, 1000 ng/ml |

TABLE 3-continued

List of PRRs agonists used to stimulate BMDCs from newborn and adult mice

| Receptor | Agonist Name | Concentration Range |
|---|---|---|
| TLR5 | Flagellin S.t. ultrapure | 1, 10, 100 ng/ml |
| TLR2/6 | FSL-1 | 1, 10, 100 ng/ml |
| TLR7 | CL264 | 0.01, 0.1, 1, 10 µM |
| TLR7/8 | R848 | 0.01, 0.1, 1, 10 µM |
| TLR8/7 | CL075 | 0.01, 0.1, 1, 10 µM |
| TLR8 | TL8-506 | 0.01, 0.1, 1, 10 µM |
| TLR9 | CpG class C - ODN 2395 | 0.01, 0.1, 1, 10 µM |
| NOD-like receptor (NLR) agonist | | |
| NOD1 | C12-iE-DAP | 1, 10, 100 ng/ml |
| NOD2 | L18-MDP | 1, 10, 100 ng/ml |
| C-type Lectin Receptor agonists | | |
| Dectin-1 | Curdlan (β-glucan) | 0.1, 1, 10 µg/ml |
| Dectin-2 | Furfurman | 0.1, 1, 10 µg/ml |
| MINCLE | TDB | 0.1, 1, 10 µg/ml |
| Retinoic acid-inducible gene (RIG)-I-like receptor (RLRs) agonists | | |
| RIG-I | 5'ppp-dsRNA | 10, 100, 1000 ng/ml |
| RIG-I | Poly (dA:dT) | 10, 100, 1000 ng/ml |
| Inflammasome inducers | | |
| NLRP3 | Alum phosphate (Adju-Phos) | 0.5, 5, 50 µg/mL |
| NLRP3 | Alum hydroxide (Alhydrogel) | 0.5, 5, 50 µg/mL |
| STING agonists | | |
| STING | 2'3'-cGAMP | 1, 10, 100 µg/ml |
| STING/NLRP3 | Chitosan | 1, 10, 100 µg/ml |

All publications, patents, patent applications, publication, and database entries (e.g., sequence database entries) mentioned herein, e.g., in the Background, Summary, Detailed Description, Examples, and/or References sections, are hereby incorporated by reference in their entirety as if each individual publication, patent, patent application, publication, and database entry was specifically and individually incorporated herein by reference. In case of conflict, the present application, including any definitions herein, will control.

EQUIVALENTS AND SCOPE

Those skilled in the art will recognize, or be able to ascertain using no more than routine experimentation, many equivalents of the embodiments described herein. The scope of the present disclosure is not intended to be limited to the above description, but rather is as set forth in the appended claims.

Articles such as "a," "an," and "the" may mean one or more than one unless indicated to the contrary or otherwise evident from the context. Claims or descriptions that include "or" between two or more members of a group are considered satisfied if one, more than one, or all of the group members are present, unless indicated to the contrary or otherwise evident from the context. The disclosure of a group that includes "or" between two or more group members provides embodiments in which exactly one member of the group is present, embodiments in which more than one members of the group are present, and embodiments in which all of the group members are present. For purposes of brevity those embodiments have not been individually spelled out herein, but it will be understood that each of these embodiments is provided herein and may be specifically claimed or disclaimed.

It is to be understood that the disclosure encompasses all variations, combinations, and permutations in which one or more limitation, element, clause, or descriptive term, from one or more of the claims or from one or more relevant portion of the description, is introduced into another claim. For example, a claim that is dependent on another claim can be modified to include one or more of the limitations found in any other claim that is dependent on the same base claim. Furthermore, where the claims recite a composition, it is to be understood that methods of making or using the composition according to any of the methods of making or using disclosed herein or according to methods known in the art, if any, are included, unless otherwise indicated or unless it would be evident to one of ordinary skill in the art that a contradiction or inconsistency would arise.

Where elements are presented as lists, e.g., in Markush group format, it is to be understood that every possible subgroup of the elements is also disclosed, and that any element or subgroup of elements can be removed from the group. It is also noted that the term "comprising" is intended to be open and permits the inclusion of additional elements or steps. It should be understood that, in general, where an embodiment, product, or method is referred to as comprising particular elements, features, or steps, embodiments, products, or methods that consist, or consist essentially of, such elements, features, or steps, are provided as well. For purposes of brevity those embodiments have not been individually spelled out herein, but it will be understood that each of these embodiments is provided herein and may be specifically claimed or disclaimed.

Where ranges are given, endpoints are included. Furthermore, it is to be understood that unless otherwise indicated or otherwise evident from the context and/or the understanding of one of ordinary skill in the art, values that are expressed as ranges can assume any specific value within the stated ranges in some embodiments, to the tenth of the unit of the lower limit of the range, unless the context clearly dictates otherwise. For purposes of brevity, the values in each range have not been individually spelled out herein, but it will be understood that each of these values is provided herein and may be specifically claimed or disclaimed. It is also to be understood that unless otherwise indicated or otherwise evident from the context and/or the understanding of one of ordinary skill in the art, values expressed as ranges can assume any subrange within the given range, wherein the endpoints of the subrange are expressed to the same degree of accuracy as the tenth of the unit of the lower limit of the range.

Where websites are provided, URL addresses are provided as non-browser-executable codes, with periods of the respective web address in parentheses. The actual web addresses do not contain the parentheses.

In addition, it is to be understood that any particular embodiment of the present disclosure may be explicitly excluded from any one or more of the claims. Where ranges are given, any value within the range may explicitly be excluded from any one or more of the claims. Any embodiment, element, feature, application, or aspect of the compositions and/or methods of the disclosure, can be excluded from any one or more claims. For purposes of brevity, all of the embodiments in which one or more elements, features, purposes, or aspects is excluded are not set forth explicitly herein.

What is claimed is:

1. A method of inducing an immune response to an antigen in a subject in need thereof, the method comprising administering to the subject an effective amount of an antigen and an effective amount of an adjuvantation system comprising a Stimulator of Interferon Genes (STING) ligand, wherein the subject is a newborn.

2. The method of claim 1, wherein the STING ligand comprises 2'3'-cGAMP.

3. The method of claim 1, wherein the adjuvantation system further comprises alum.

4. The method of claim 3, wherein the STING ligand is adsorbed into the alum.

5. The method of claim 3, wherein the subject is less than 28 days of age at the time of administration.

6. The method of claim 5, wherein a second administration occurs when the subject is no more than 6 months of age.

7. The method of claim 5, wherein the subject is born prematurely, has low birth weight or is immune-compromised.

8. The method of claim 1, wherein the antigen comprises a protein or polypeptide or a nucleic acid encoding a protein or a polypeptide.

9. The method of claim 1, wherein the antigen is from a microbial pathogen.

10. The method of claim 1, wherein the antigen is a cancer-specific antigen.

11. The method of claim 1, wherein the adjuvantation system enhances the production of antigen-specific antibodies, compared to when the antigen is administered alone.

12. The method of claim 1, wherein the adjuvantation system enhances the cytokine production of antigen-specific T cells, compared to when the antigen is administered alone.

13. The method of claim 1, wherein the adjuvantation system polarizes the innate immune response toward T follicular helper (Tfh) cell immunity.

14. The method of claim 1, wherein the adjuvantation system polarizes the innate immune response toward T helper 1 (Th1) cell immunity.

15. The method of claim 1, wherein the adjuvantation system prolongs a protective effect in the subject against the antigen, compared to when the antigen is administered alone.

16. The method of claim 1, wherein the adjuvantation system increases rate of an immune response, compared to when the antigen is administered alone.

17. The method of claim 1, wherein the antigen produces a same level of immune response against the antigen at a lower dose in the presence of the adjuvantation system, compared to when the antigen is administered alone.

* * * * *